United States Patent
Swanson et al.

(10) Patent No.: US 7,052,492 B2
(45) Date of Patent: May 30, 2006

(54) SURGICAL METHOD AND APPARATUS FOR POSITIONING A DIAGNOSTIC OR THERAPEUTIC ELEMENT WITHIN THE BODY

(75) Inventors: David K. Swanson, Mountain View, CA (US); Sidney D. Fleischman, Menlo Park, CA (US); Josef V. Koblish, Sunnyvale, CA (US); Russell B. Thompson, Los Altos, CA (US); James G. Whayne, Saratoga, CA (US); Thomas R. Jenkins, Oakland, CA (US); Edward J. Snyder, San Jose, CA (US)

(73) Assignee: EP Technologies, Inc., San Jose, CA (US)

( * ) Notice: Subject to any disclaimer, the term of this patent is extended or adjusted under 35 U.S.C. 154(b) by 0 days.

(21) Appl. No.: 10/930,082

(22) Filed: Aug. 30, 2004

(65) Prior Publication Data

US 2005/0033285 A1    Feb. 10, 2005

Related U.S. Application Data

(63) Continuation of application No. 10/160,960, filed on May 30, 2002, now Pat. No. 6,786,905, which is a continuation of application No. 09/644,847, filed on Aug. 22, 2000, now Pat. No. 6,425,895, which is a continuation of application No. 09/072,872, filed on May 5, 1998, now Pat. No. 6,142,994, which is a continuation-in-part of application No. 08/321,424, filed on Oct. 11, 1994, now Pat. No. 5,885,278, which is a continuation-in-part of application No. 08/320,198, filed on Oct. 7, 1994, now abandoned, said application No. 09/072,872 is a continuation-in-part of application No. 08/321,092, filed on Oct. 11, 1994, now Pat. No. 5,836,947, and a continuation-in-part of application No. 08/949,117, filed on Oct. 10, 1997, now Pat. No. 6,152,920, and a continuation-in-part of application No. 08/949,083, filed on Oct. 10, 1997, now abandoned, and a continuation-in-part of application No. 08/948,729, filed on Oct. 10, 1997, now abandoned, and a continuation-in-part of application No. 08/949,084, filed on Oct. 10, 1997, now abandoned.

(51) Int. Cl.
    *A61B 18/14*    (2006.01)
(52) U.S. Cl. .......................................... 606/32; 606/41
(58) Field of Classification Search .................. 606/32, 606/41
    See application file for complete search history.

(56) References Cited

U.S. PATENT DOCUMENTS

| | | |
|---|---|---|
| 463,785 A | 11/1891 | Connable |
| 3,316,913 A | 5/1967 | Swenson |
| 3,999,555 A | 12/1976 | Person |

(Continued)

FOREIGN PATENT DOCUMENTS

DE    8621578.7 U1    2/1991

(Continued)

OTHER PUBLICATIONS

US 5,688,268, 11/1997, Billings (withdrawn)

*Primary Examiner*—Lee S. Cohen
(74) *Attorney, Agent, or Firm*—Henricks, Slavin & Holmes LLP

(57) ABSTRACT

A surgical method and apparatus for positioning a diagnostic or therapeutic element within the body. The apparatus may be catheter-based or a probe including a relatively short shaft.

16 Claims, 55 Drawing Sheets

U.S. PATENT DOCUMENTS

| | | |
|---|---|---|
| 4,011,872 A | 3/1977 | Komiya |
| 4,181,131 A | 1/1980 | Ogiu |
| 4,306,561 A | 12/1981 | de Medinaceli |
| 4,493,320 A | 1/1985 | Treat |
| 4,517,975 A | 5/1985 | Garito et al. |
| 4,523,679 A | 6/1985 | Paikoff et al. |
| 4,532,924 A | 8/1985 | Auth et al. |
| 4,565,200 A | 1/1986 | Cosman |
| 4,567,890 A | 2/1986 | Ohta |
| 4,651,734 A | 3/1987 | Doss et al. |
| 4,681,122 A | 7/1987 | Winters et al. |
| 4,765,331 A | 8/1988 | Petruzzi et al. |
| 4,800,899 A | 1/1989 | Elliott |
| 4,920,978 A | 5/1990 | Colvin |
| 5,002,561 A | 3/1991 | Fisher |
| 5,013,312 A | 5/1991 | Parins et al. |
| 5,078,716 A | 1/1992 | Doll |
| 5,088,997 A | 2/1992 | Delahuerga et al. |
| 5,092,314 A | 3/1992 | Zeitels |
| 5,108,391 A | 4/1992 | Flachenecker et al. |
| 5,122,137 A | 6/1992 | Lennox |
| 5,131,379 A | 7/1992 | Sewell, Jr. |
| 5,147,357 A | 9/1992 | Rose et al. |
| 5,244,462 A | 9/1993 | Delahuerga et al. |
| 5,249,121 A | 9/1993 | Baum et al. |
| 5,263,493 A | 11/1993 | Avitall |
| 5,277,201 A | 1/1994 | Stern |
| 5,290,286 A | 3/1994 | Parins |
| 5,306,234 A | 4/1994 | Johnson |
| 5,318,564 A | 6/1994 | Eggers |
| 5,324,288 A | 6/1994 | Billings et al. |
| 5,342,356 A | 8/1994 | Ellman et al. |
| 5,370,650 A | 12/1994 | Tovey et al. |
| 5,381,896 A | 1/1995 | Simons |
| 5,383,876 A | 1/1995 | Nardella |
| 5,401,274 A | 3/1995 | Kusunoki |
| 5,403,342 A | 4/1995 | Tovey et al. |
| 5,415,656 A | 5/1995 | Tihon et al. |
| 5,423,810 A | 6/1995 | Goble et al. |
| 5,437,664 A | 8/1995 | Cohen et al. |
| 5,437,665 A | 8/1995 | Munro |
| 5,443,463 A | 8/1995 | Stern et al. |
| 5,445,638 A | 8/1995 | Rydell et al. |
| 5,451,224 A | 9/1995 | Goble et al. |
| 5,456,699 A | 10/1995 | Armstrong |
| 5,486,173 A | 1/1996 | Vancaillie |
| 5,505,730 A | 4/1996 | Edwards |
| 5,562,720 A | 10/1996 | Stern et al. |
| 5,569,242 A | 10/1996 | Lax et al. |
| 5,571,098 A | 11/1996 | Domankevitz et al. |
| 5,571,215 A | 11/1996 | Sterman |
| 5,624,454 A | 4/1997 | Palti |
| 5,626,607 A | 5/1997 | Malecki et al. |
| 5,630,426 A | 5/1997 | Eggers et al. |
| 5,658,280 A | 8/1997 | Issa |
| 5,676,678 A | 10/1997 | Schad |
| 5,681,282 A | 10/1997 | Eggers et al. |
| 5,683,366 A | 11/1997 | Eggers et al. |
| 5,687,723 A | 11/1997 | Avitall |
| 5,688,266 A | 11/1997 | Edwards et al. |
| 5,697,536 A | 12/1997 | Eggers et al. |
| 5,697,882 A | 12/1997 | Eggers et al. |
| 5,697,909 A | 12/1997 | Eggers et al. |
| 5,702,371 A | 12/1997 | Bierman |
| 5,702,438 A | 12/1997 | Avitall |
| 5,720,745 A | 2/1998 | Farin et al. |
| 5,730,704 A | 3/1998 | Avitall |
| 5,733,280 A | 3/1998 | Avitall |
| 5,738,683 A | 4/1998 | Osypka |
| 5,746,748 A | 5/1998 | Steinberg |
| 5,779,722 A | 7/1998 | Shturman et al. |
| 5,788,688 A | 8/1998 | Bauer et al. |
| 5,823,956 A * | 10/1998 | Roth et al. ............... 606/41 |
| 5,830,183 A | 11/1998 | Krieger |
| 5,833,690 A | 11/1998 | Yates et al. |
| 5,836,947 A | 11/1998 | Fleischman et al. |
| 5,865,791 A * | 2/1999 | Whayne et al. ............ 604/500 |
| 5,868,742 A | 2/1999 | Manes et al. |
| 5,871,523 A | 2/1999 | Fleischman et al. |
| 5,895,386 A | 4/1999 | Odell et al. |
| 5,908,420 A | 6/1999 | Parins et al. |
| 5,947,964 A | 9/1999 | Eggers et al. |
| 5,957,968 A | 9/1999 | Belden et al. |
| 5,984,917 A | 11/1999 | Fleischman et al. |
| 6,012,457 A | 1/2000 | Lesh |
| 6,064,902 A | 5/2000 | Haissaguerre et al. |
| 6,071,281 A | 6/2000 | Burnside |
| 6,120,496 A | 9/2000 | Whayne |
| 6,132,438 A | 10/2000 | Fleischman et al. |
| 6,139,538 A | 10/2000 | Houghton |
| 6,142,994 A | 11/2000 | Swanson et al. |
| 6,152,920 A | 11/2000 | Thompson et al. |
| 6,161,543 A * | 12/2000 | Cox et al. ................. 606/41 |
| 6,237,605 B1 | 5/2001 | Vaska et al. |
| 6,267,760 B1 | 7/2001 | Swanson |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,379,366 B1 | 4/2002 | Fleischman et al. |
| 6,416,505 B1 | 7/2002 | Fleischman et al. |
| 6,425,895 B1 | 7/2002 | Swanson et al. |
| 6,468,272 B1 | 10/2002 | Koblish et al. |
| 6,645,200 B1 | 11/2003 | Koblish et al. |
| 6,679,269 B1 | 1/2004 | Swanson |
| 6,830,576 B1 | 12/2004 | Fleischman et al. |

FOREIGN PATENT DOCUMENTS

| | | |
|---|---|---|
| DE | 4425195 C1 | 11/1995 |
| DE | 19503702 A1 | 8/1996 |
| EP | 0453071 A1 | 10/1991 |
| EP | 0484671 A2 | 5/1992 |
| EP | 0530400 A1 | 3/1993 |
| EP | 0584787 A1 | 3/1994 |
| EP | 0628288 A2 | 12/1994 |
| WO | WO 93/08755 A1 | 5/1993 |
| WO | WO 95/10236 A1 | 4/1995 |
| WO | WO 96/37156 A1 | 11/1996 |
| WO | WO 97/17027 A1 | 5/1997 |
| WO | WO 97/30644 A1 | 8/1997 |
| WO | WO 97/41793 A1 | 11/1997 |
| WO | WO 98/17187 A1 | 4/1998 |
| WO | WO 99/04696 A1 | 2/1999 |

\* cited by examiner

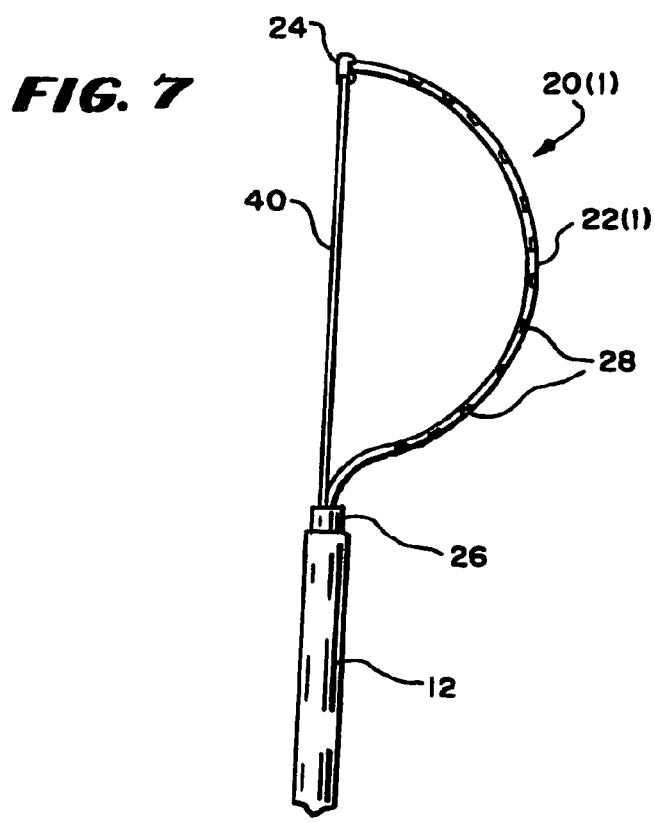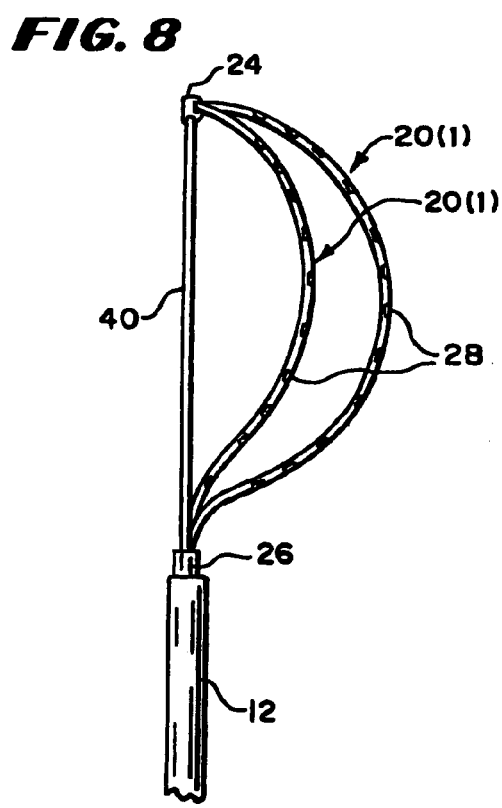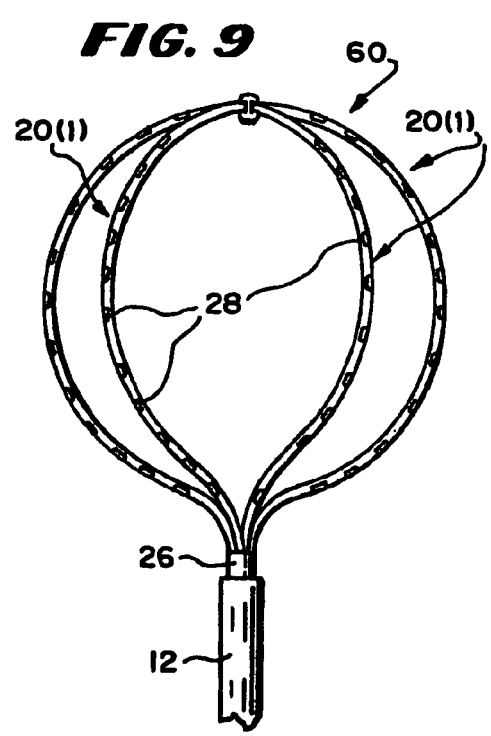

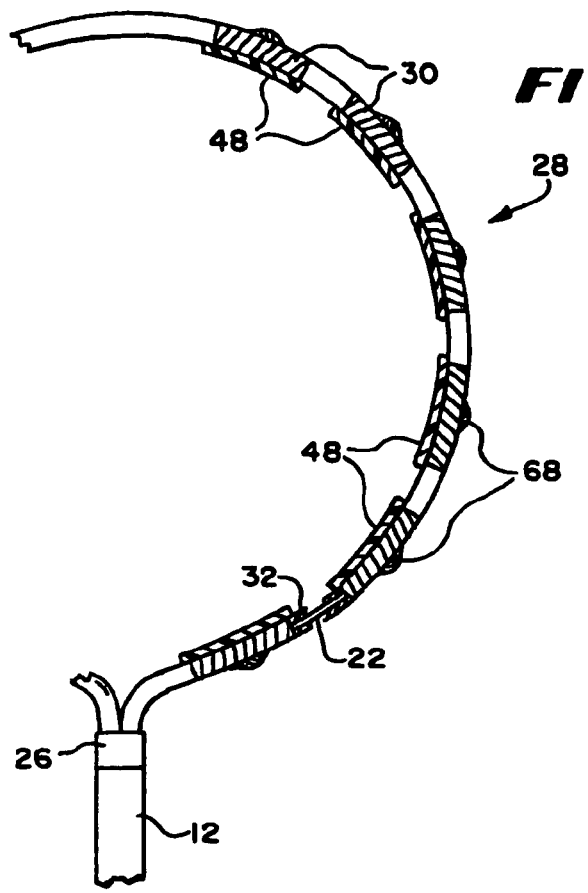
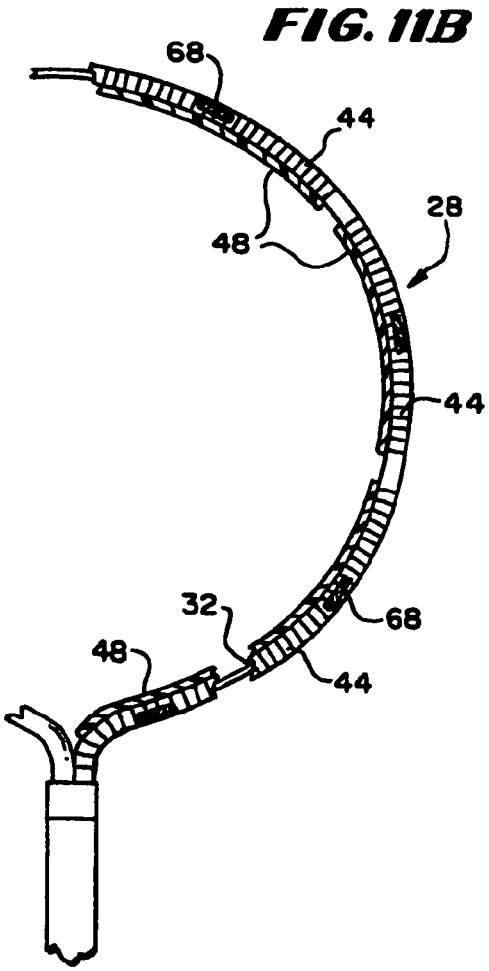
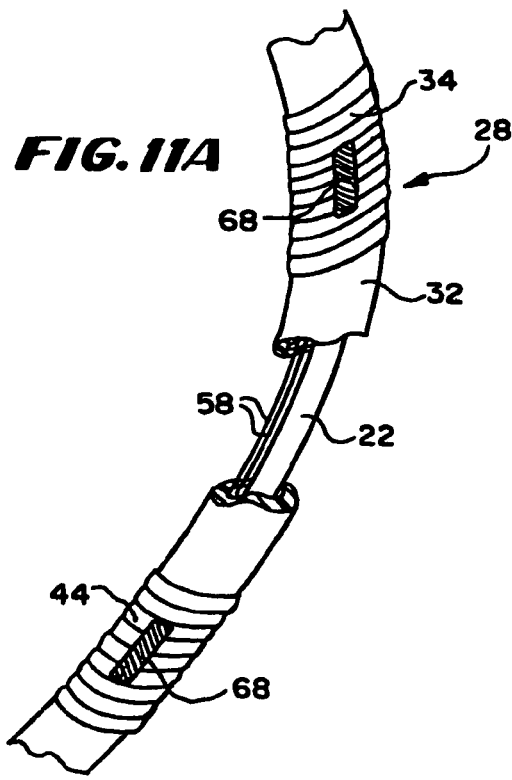

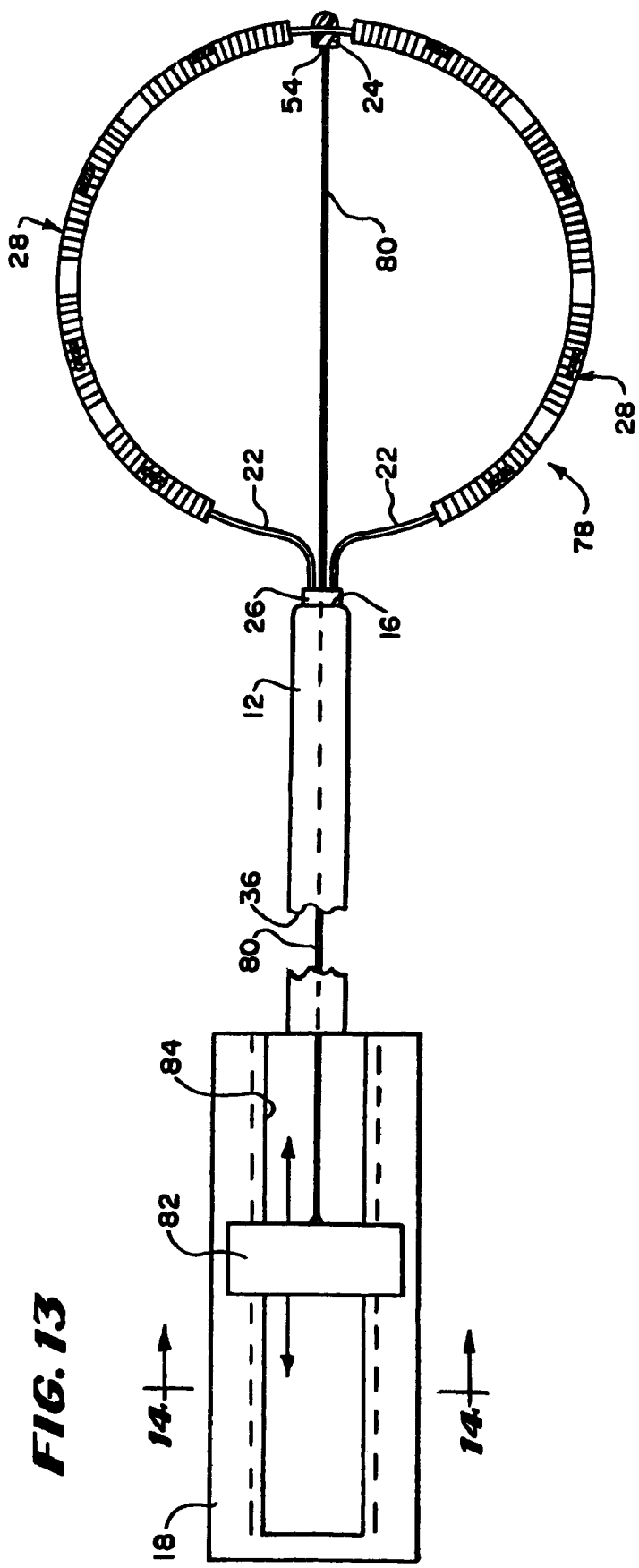
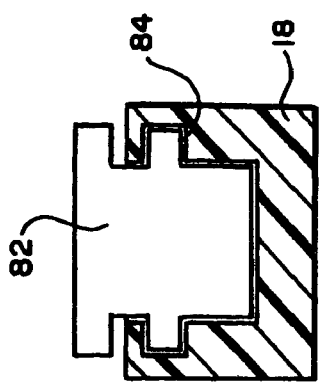
FIG. 13
FIG. 14

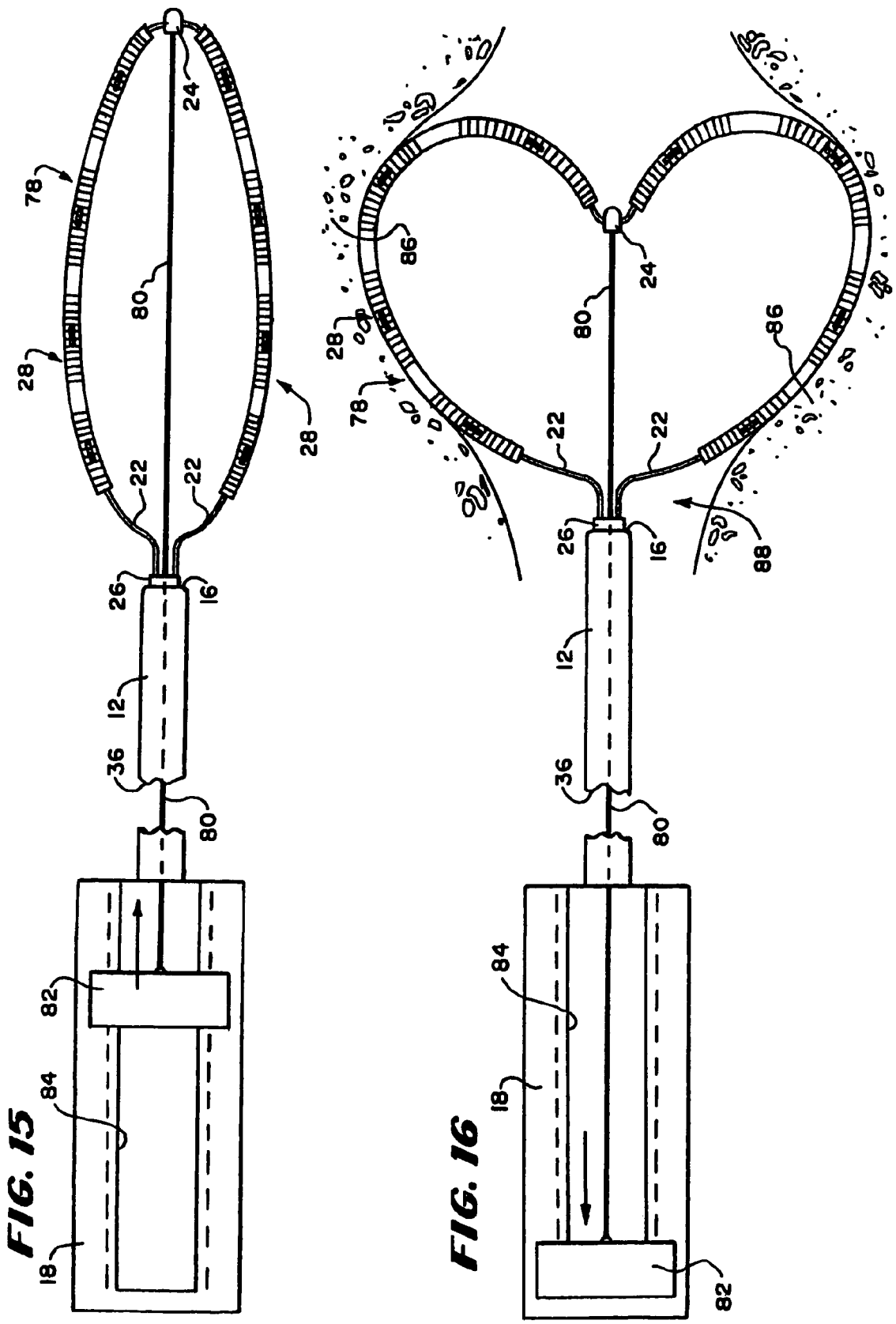

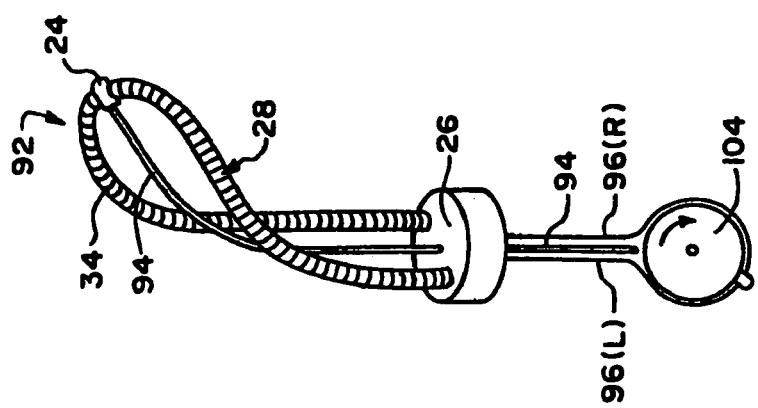
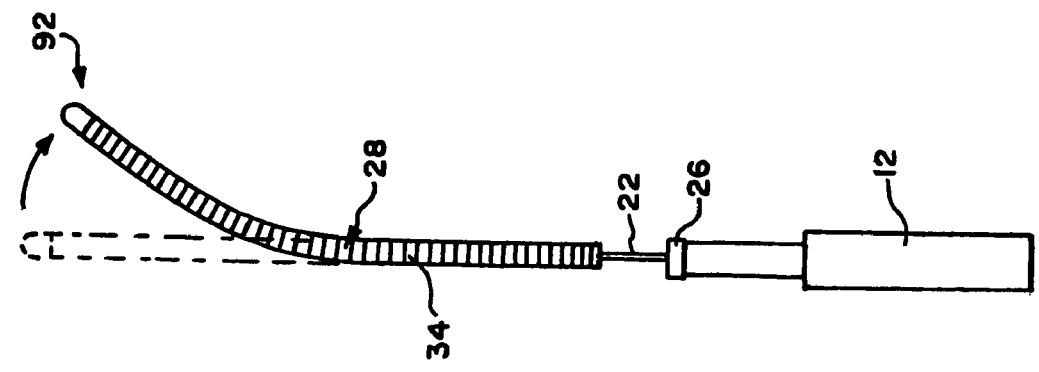
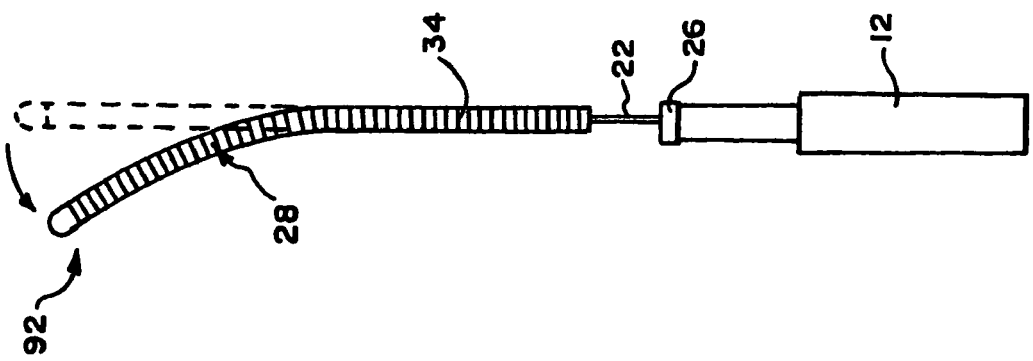

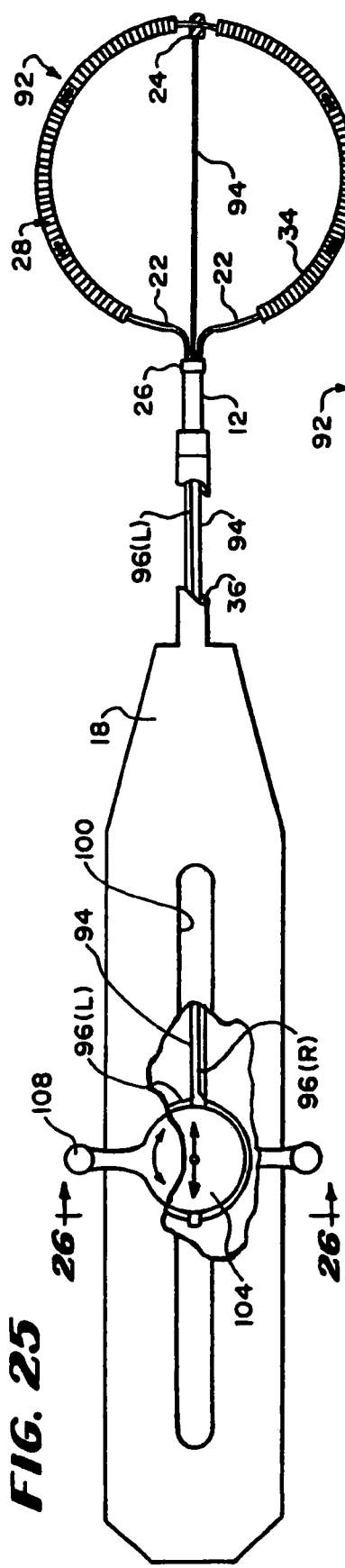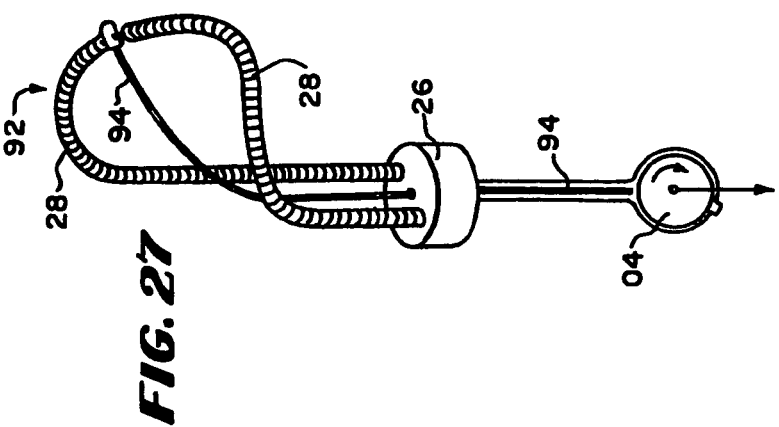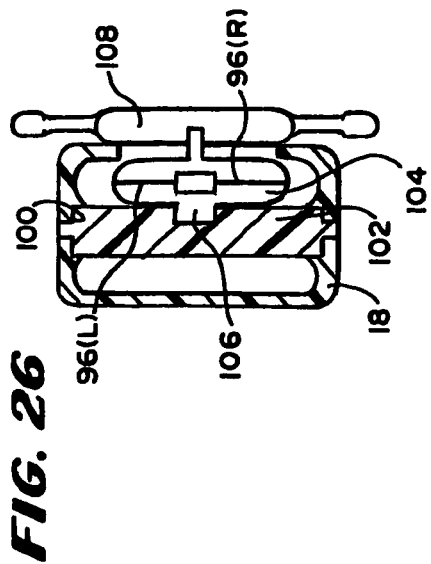

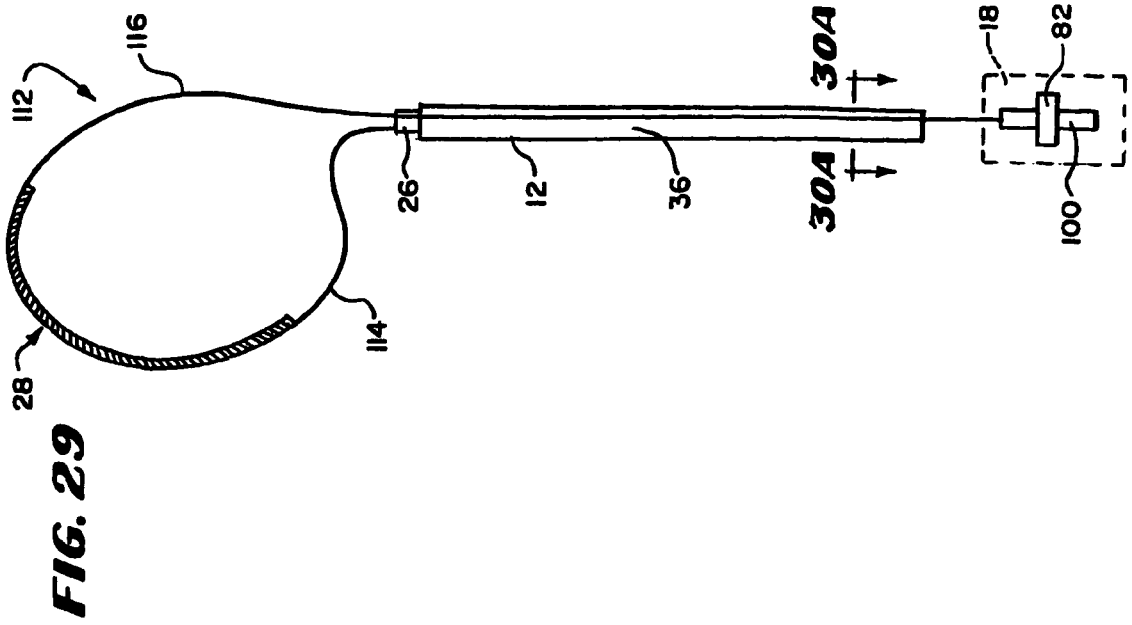
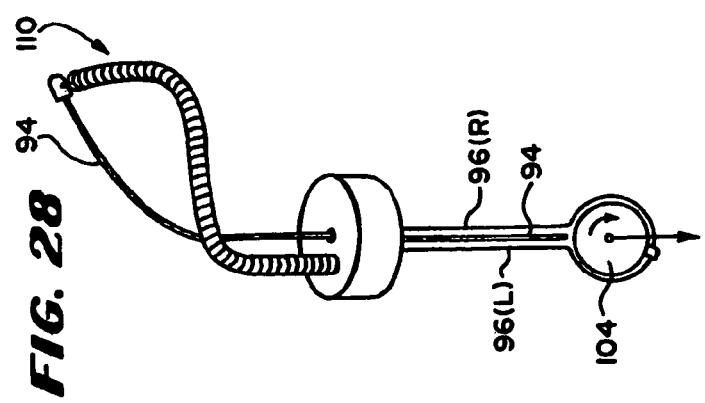

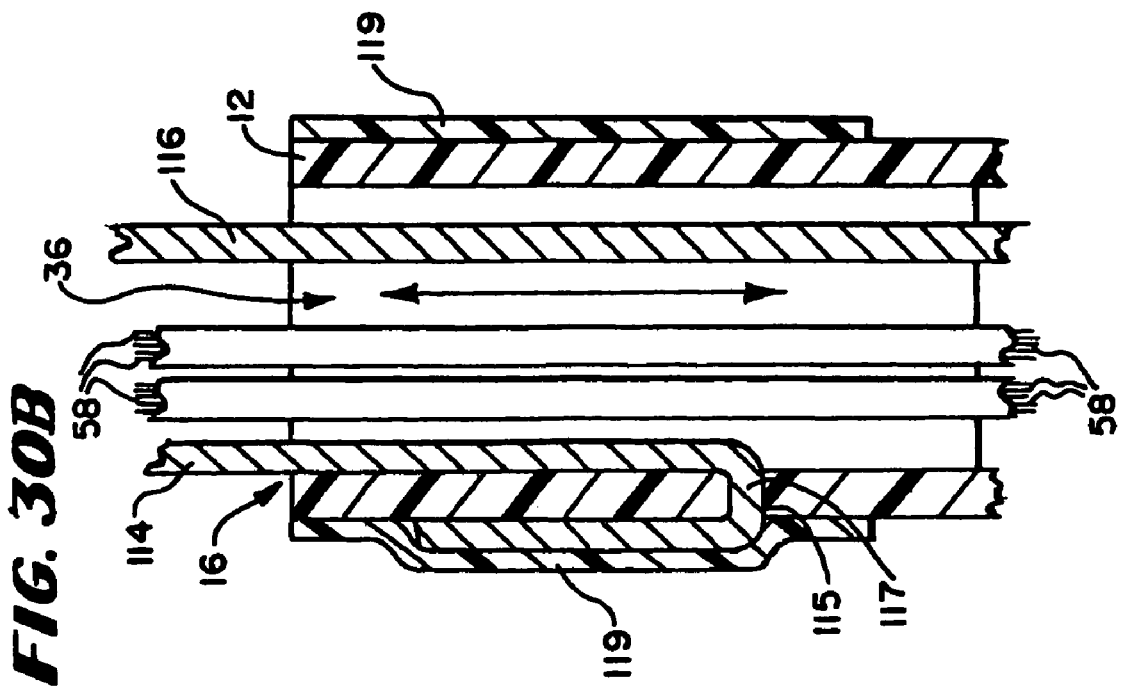
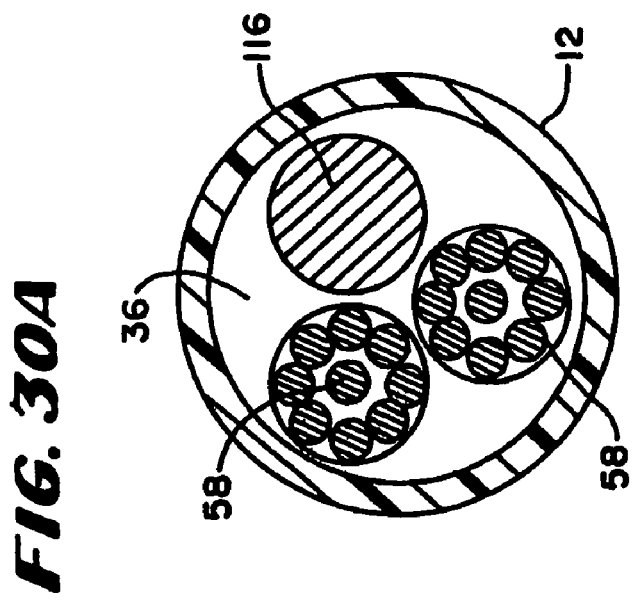

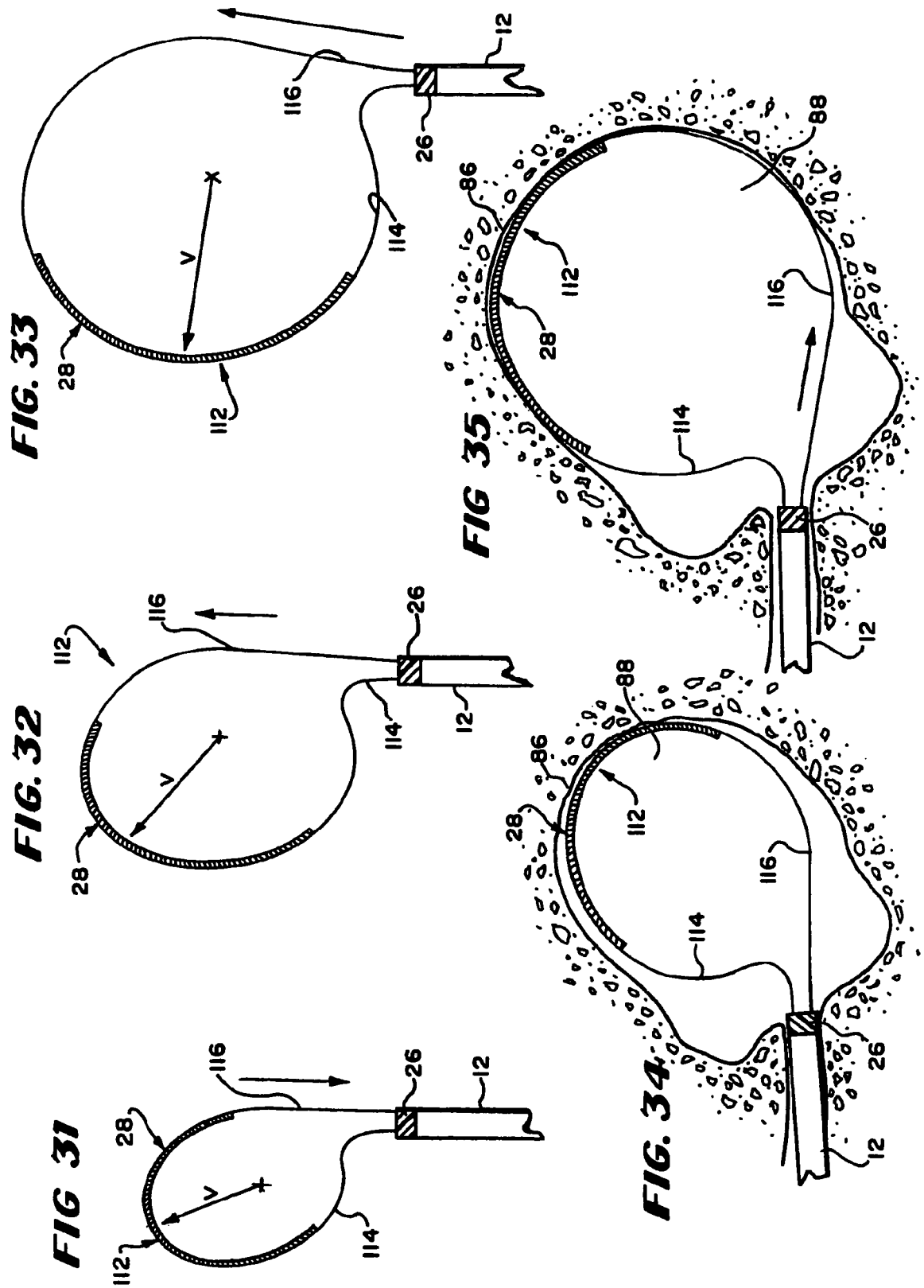

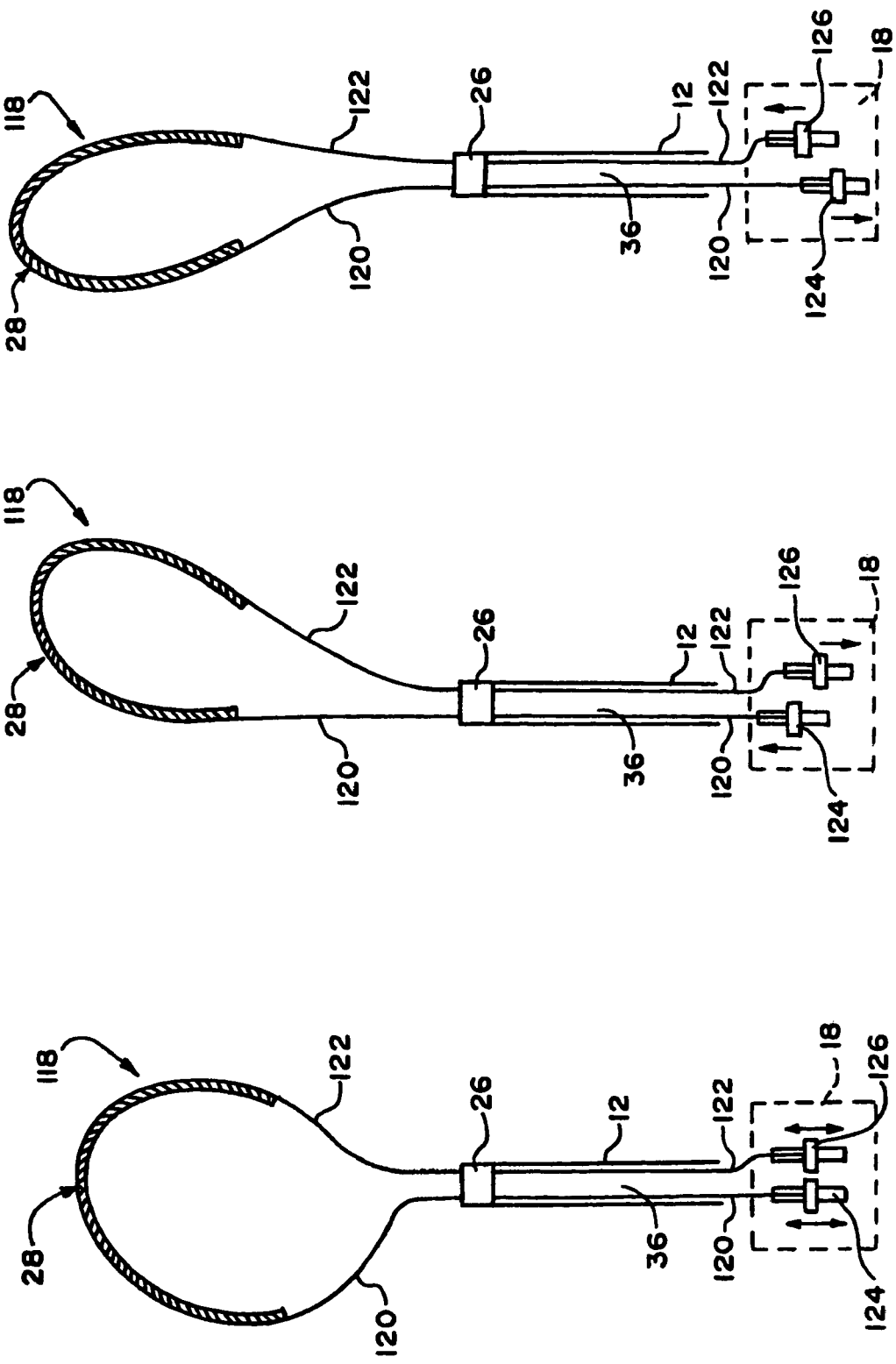

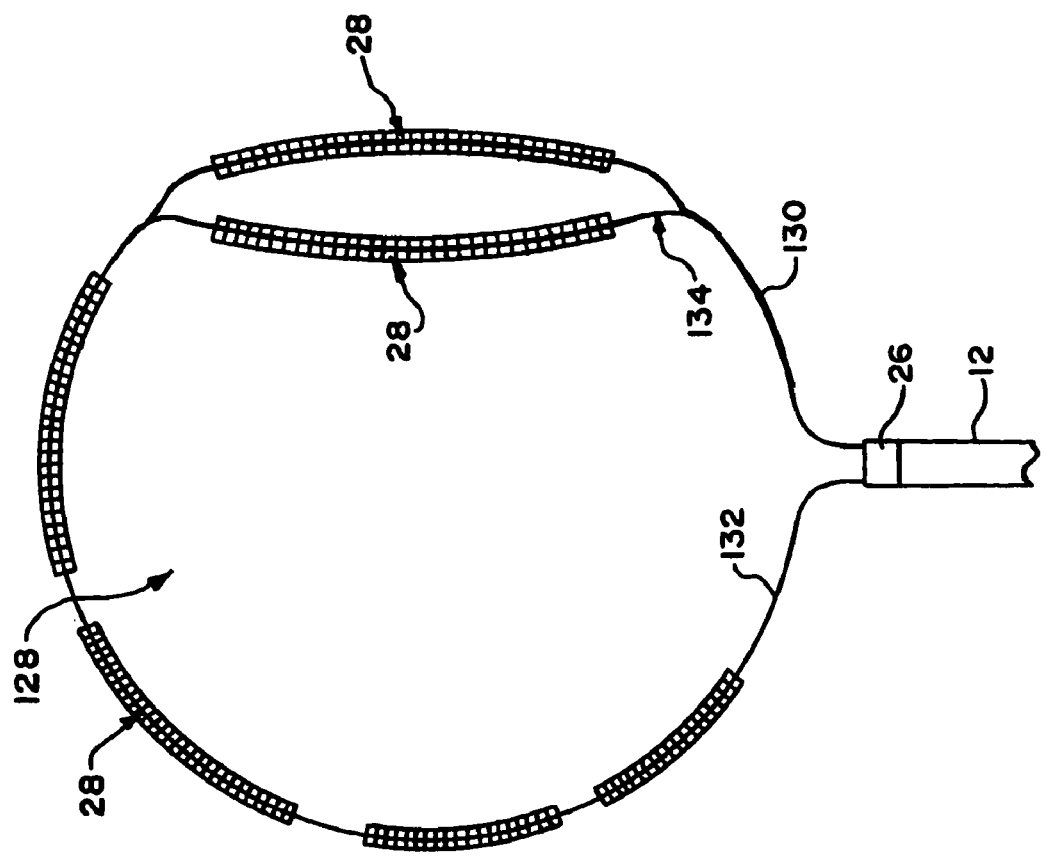
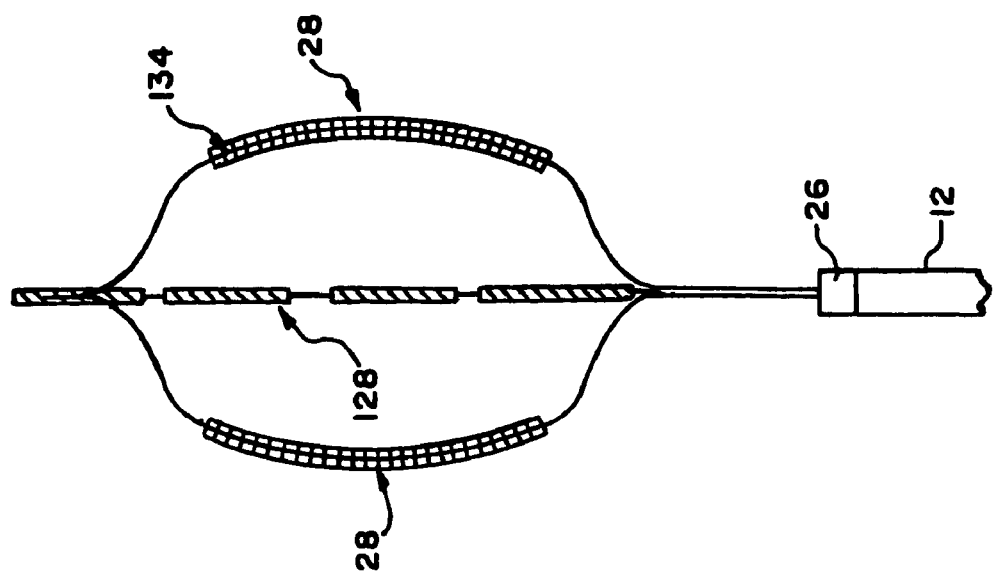

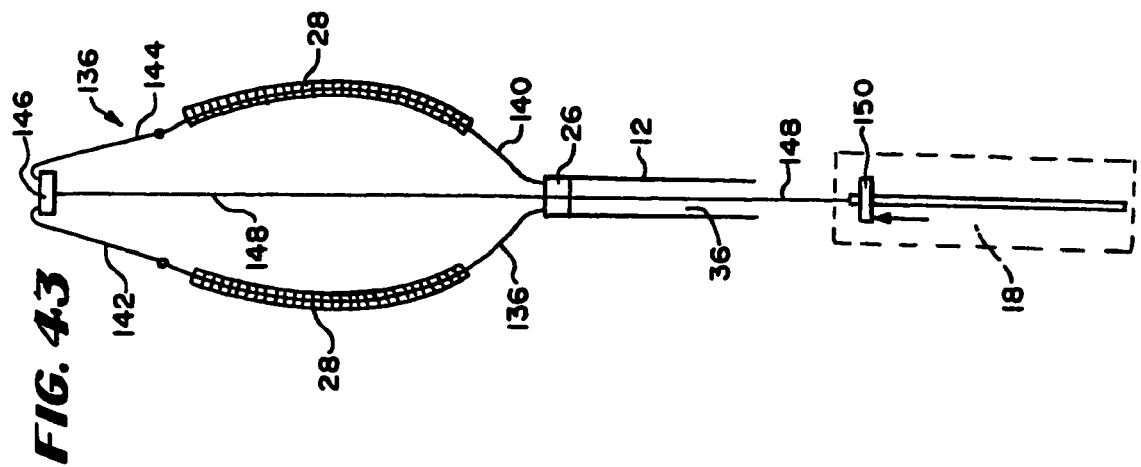
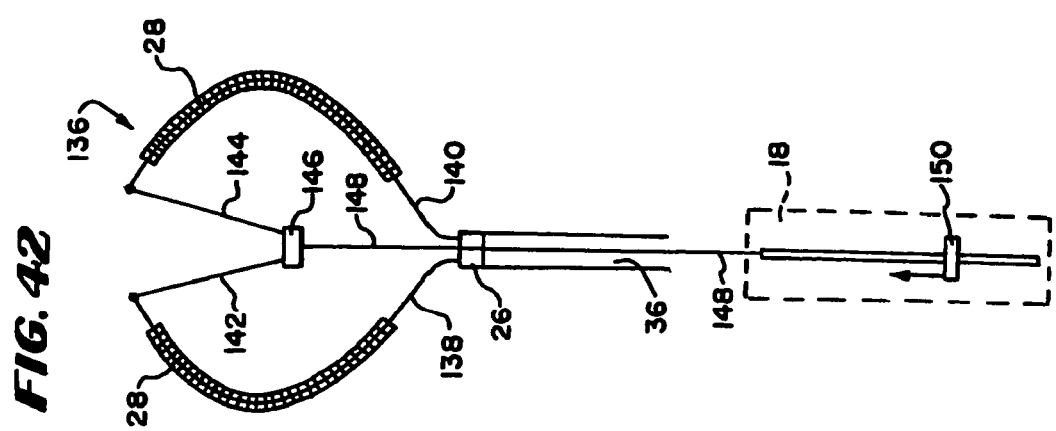
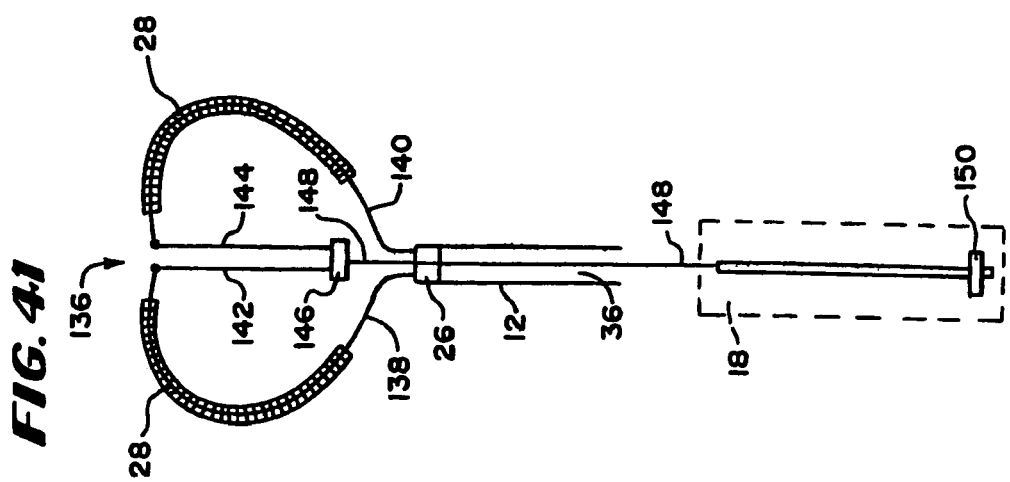

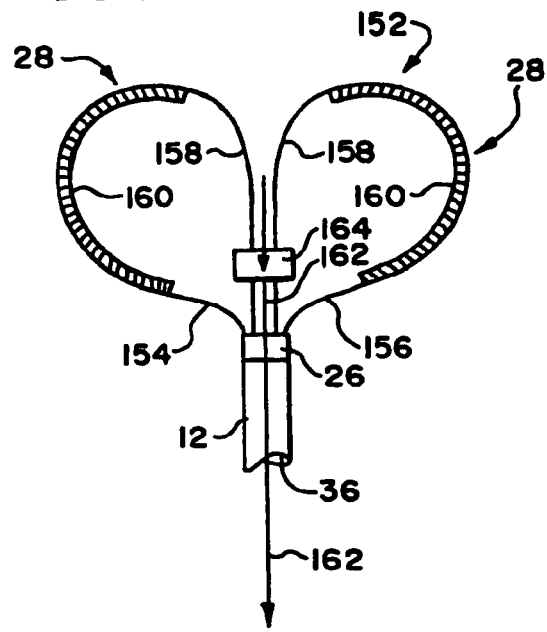
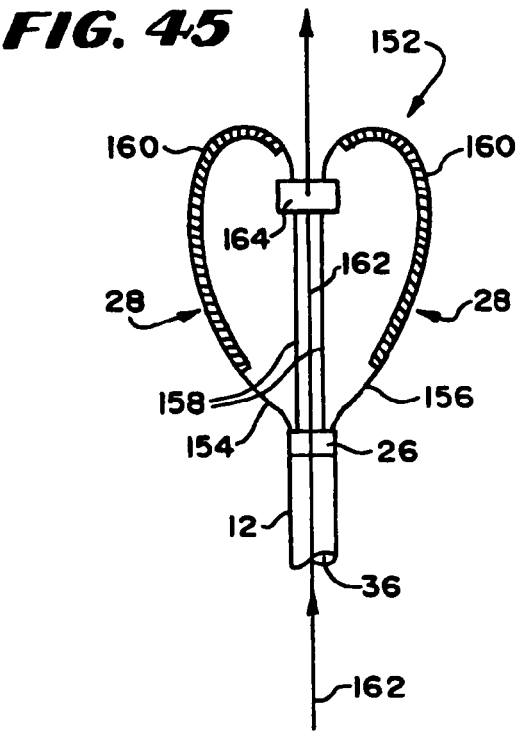
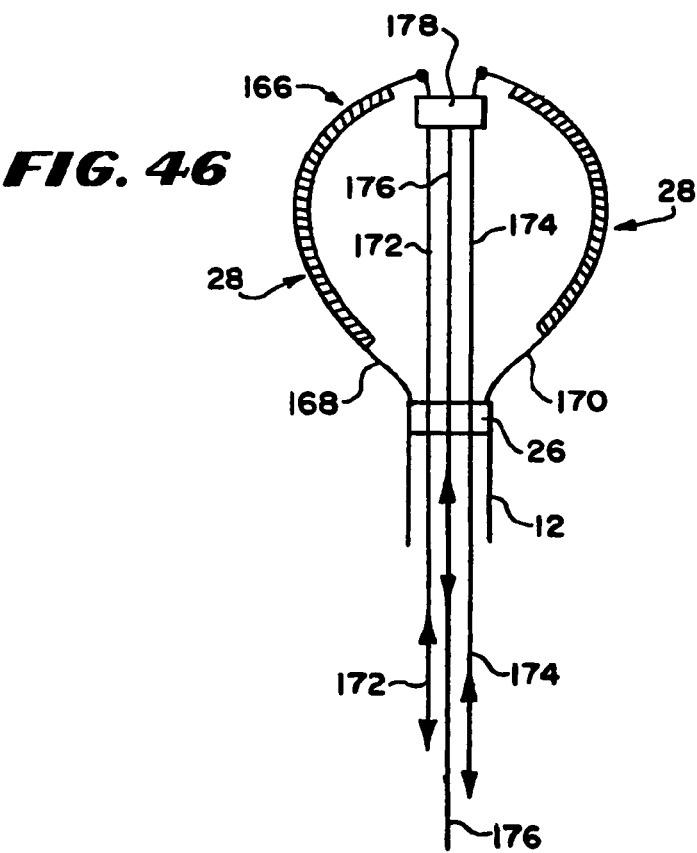

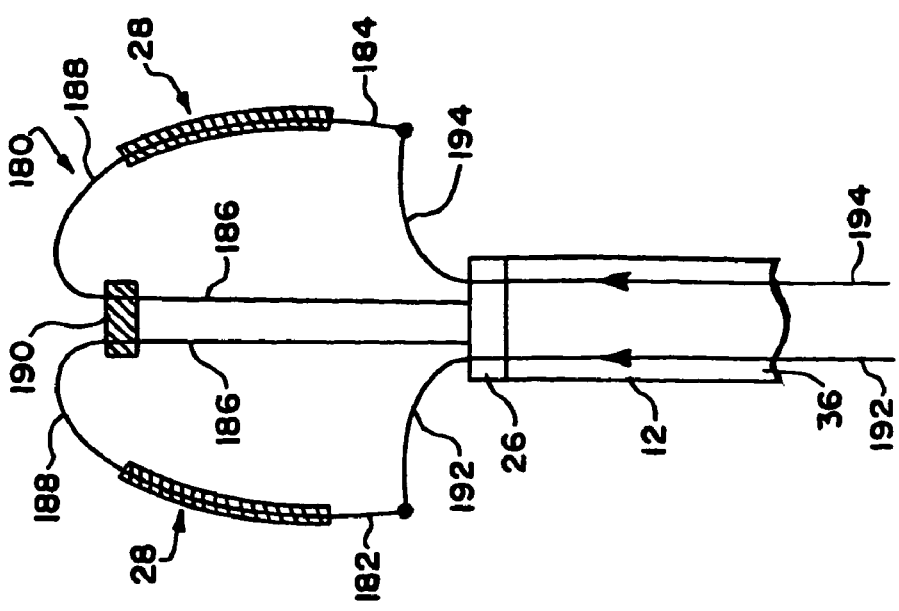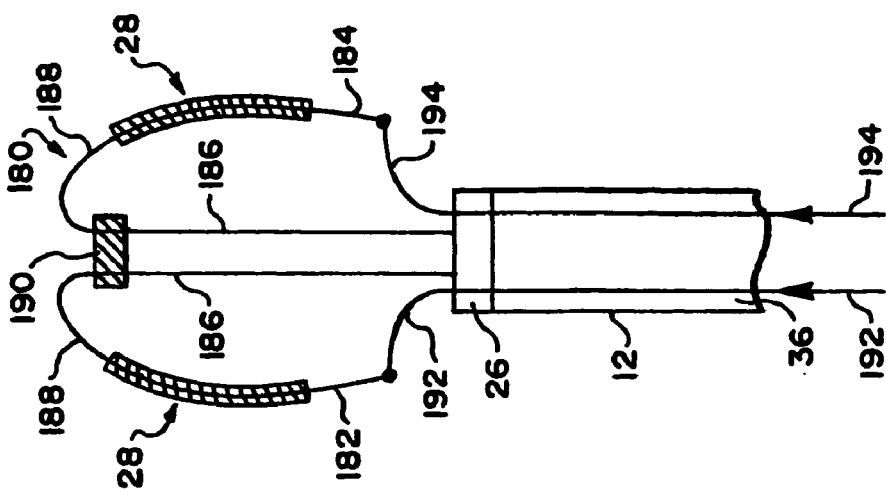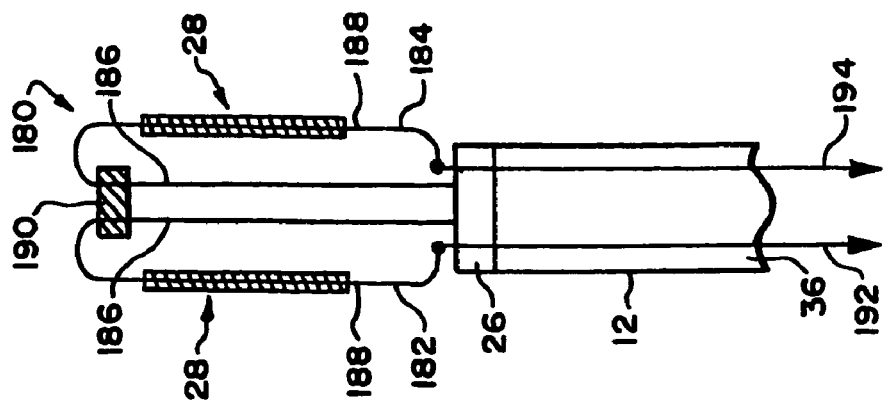

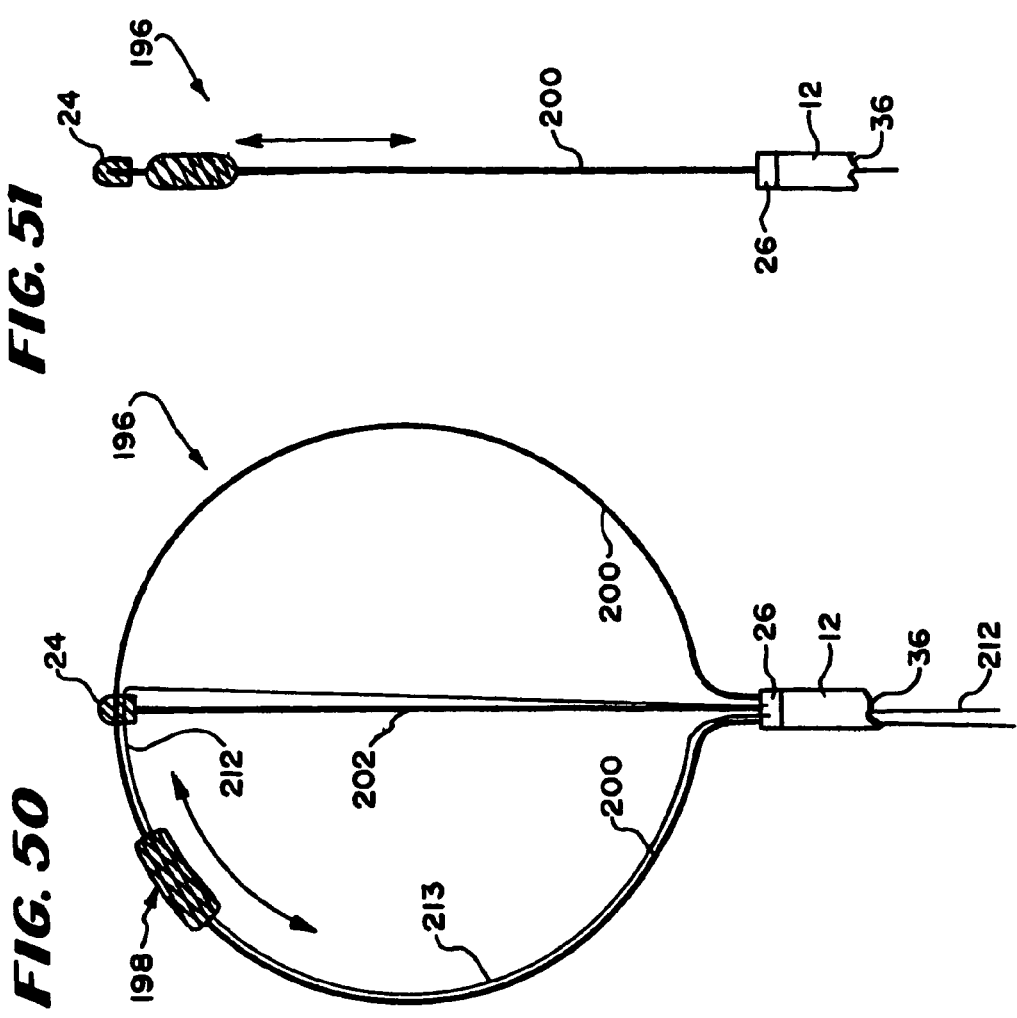

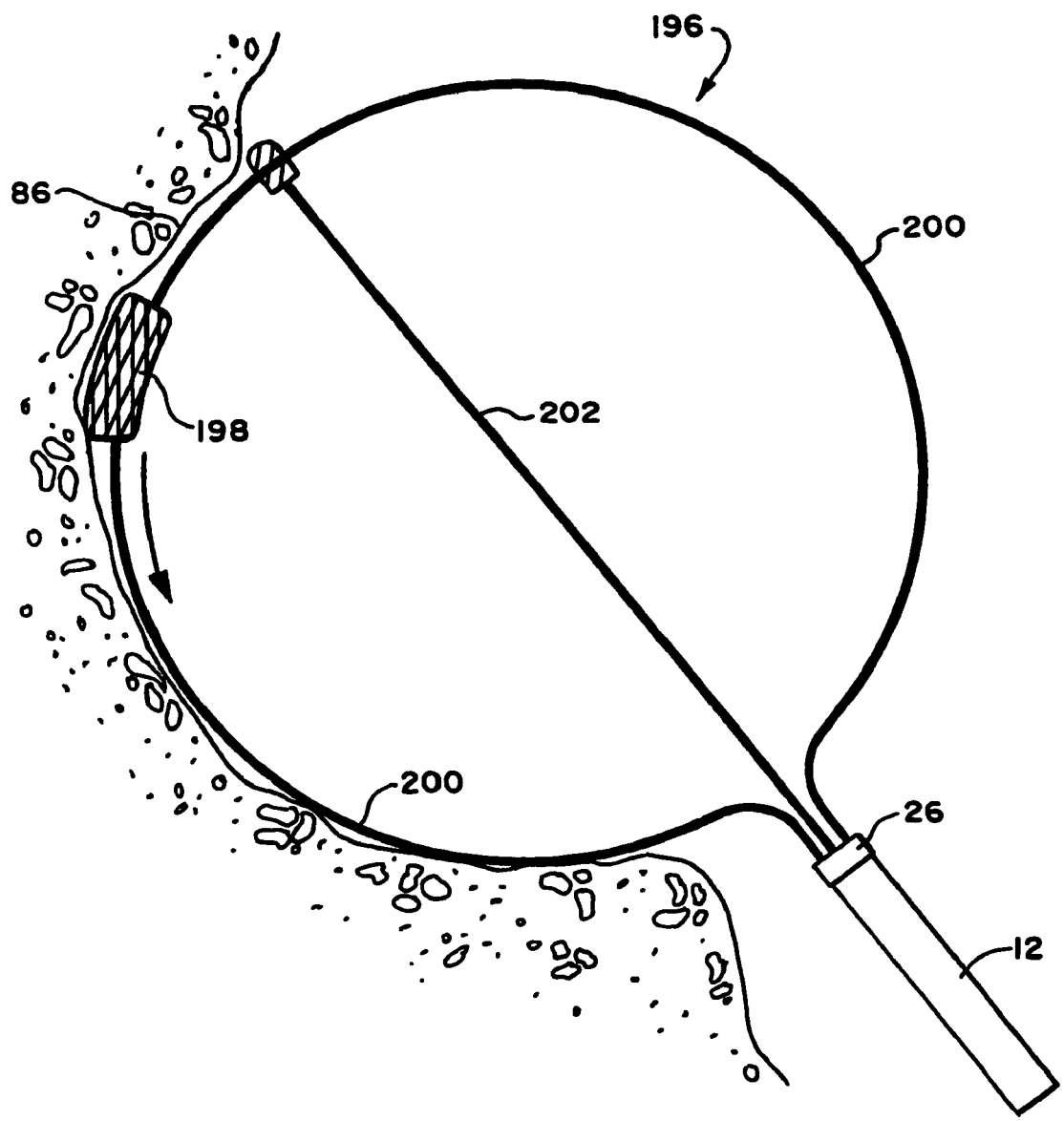

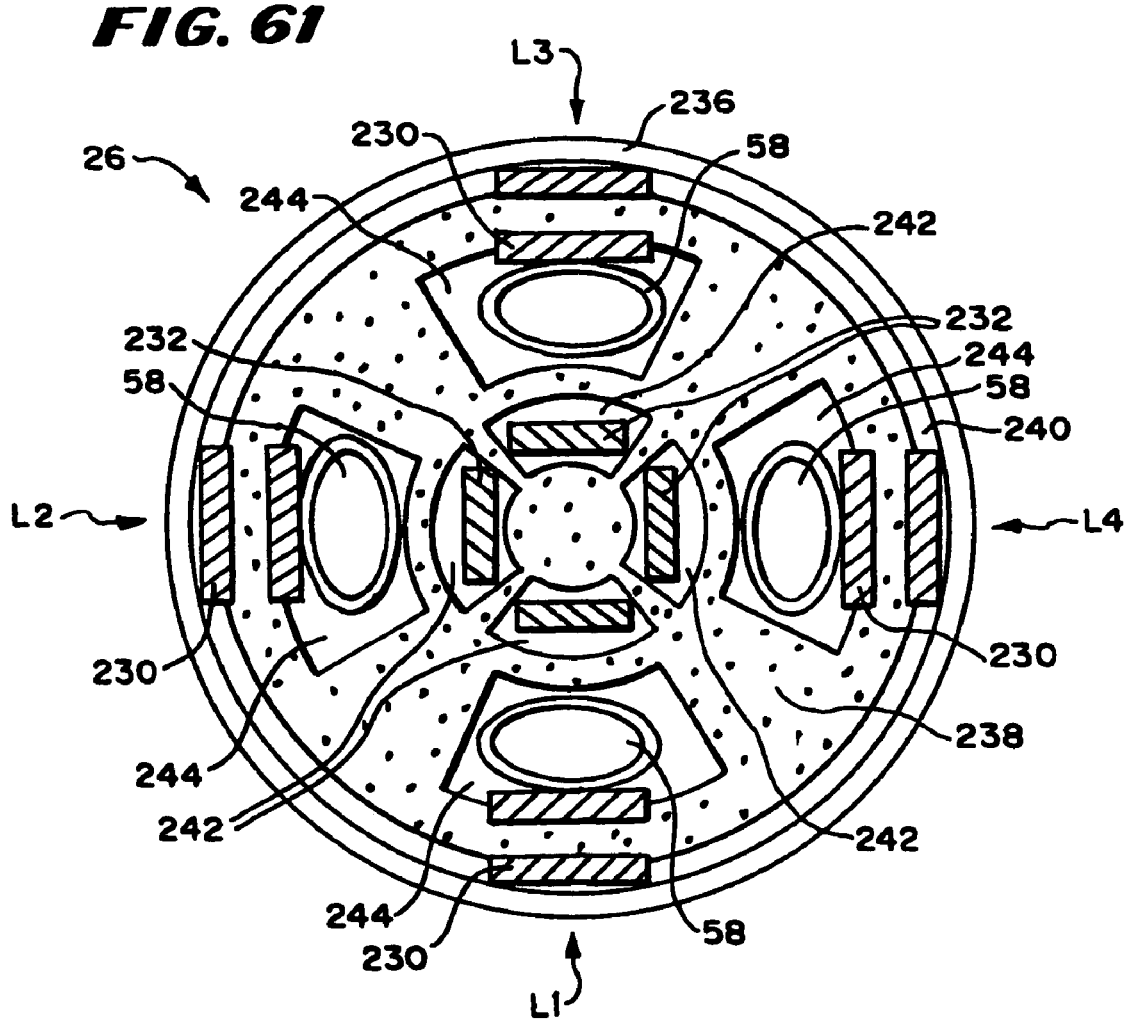

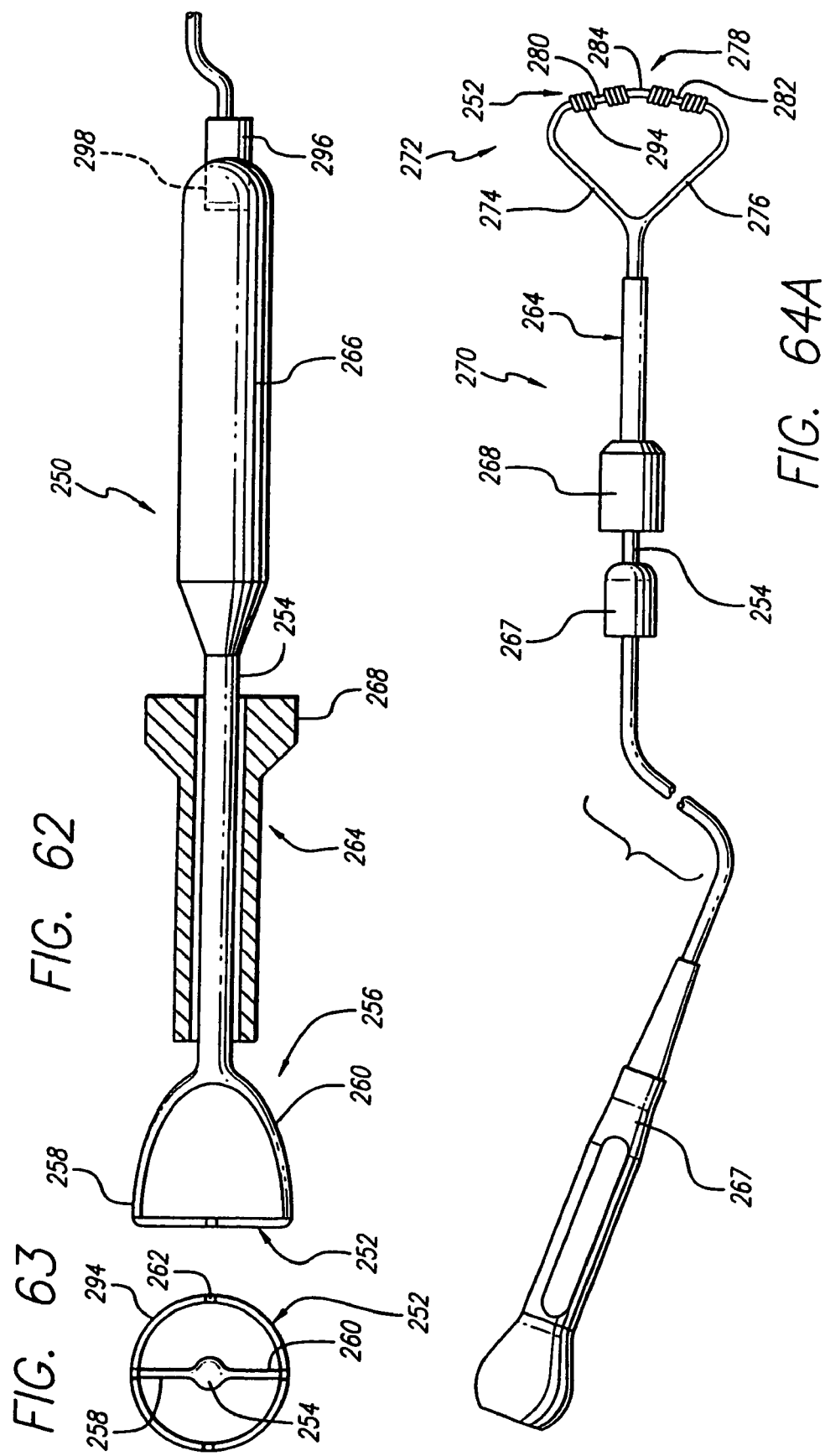

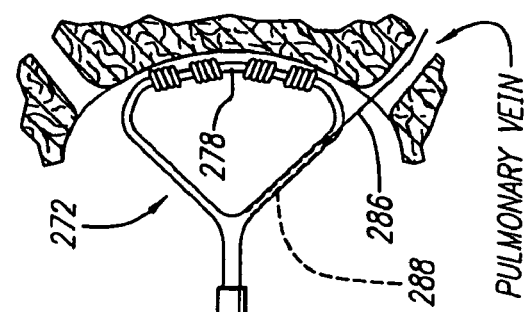
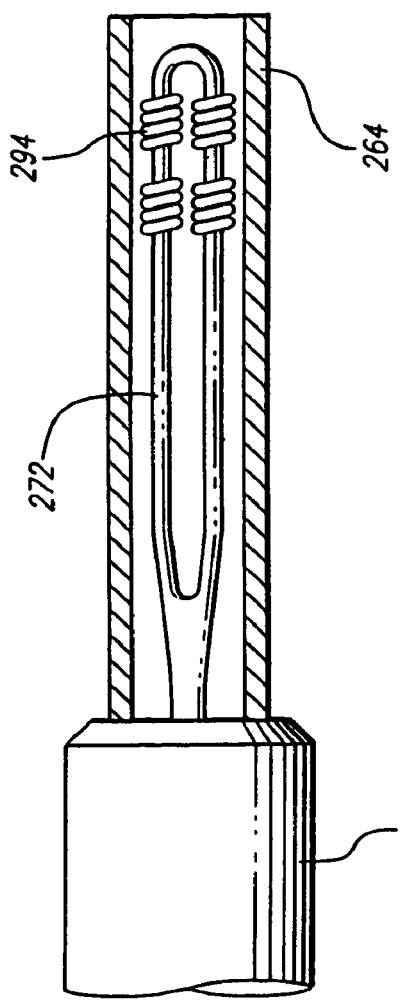
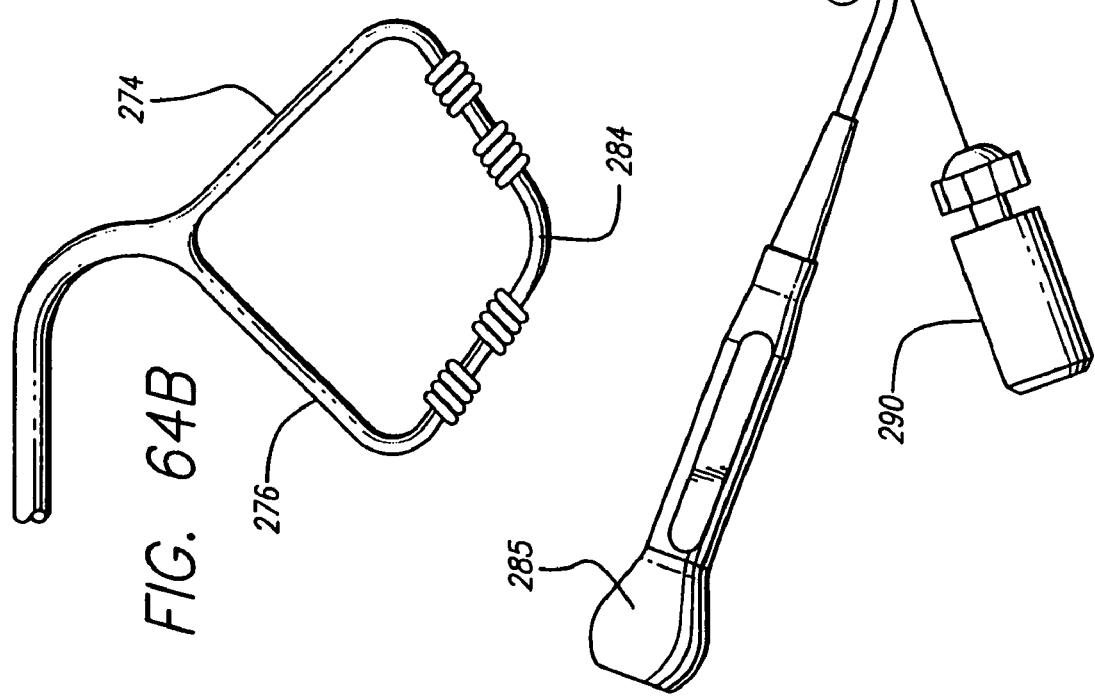
FIG. 64B
FIG. 65
FIG. 66

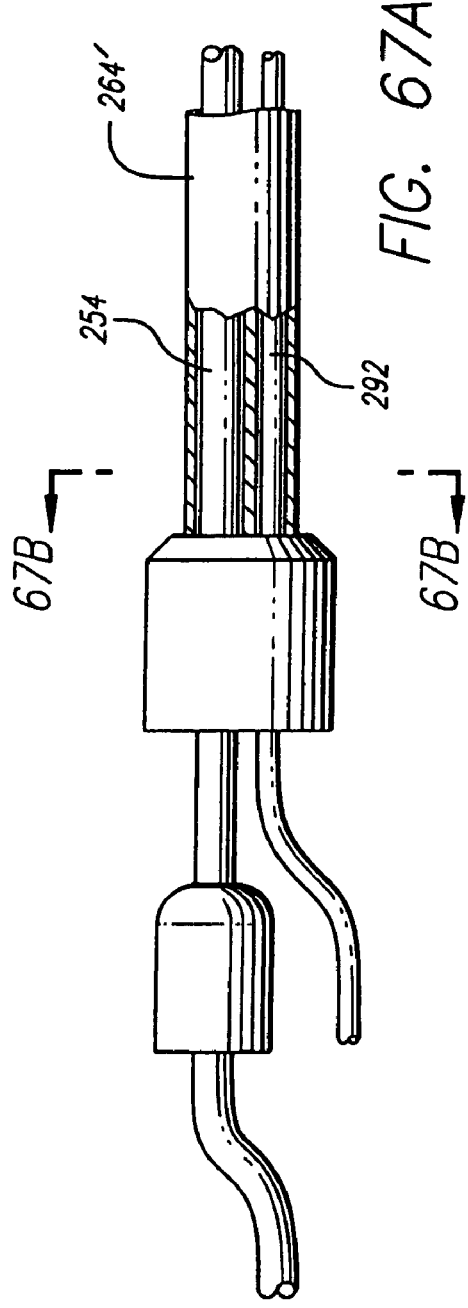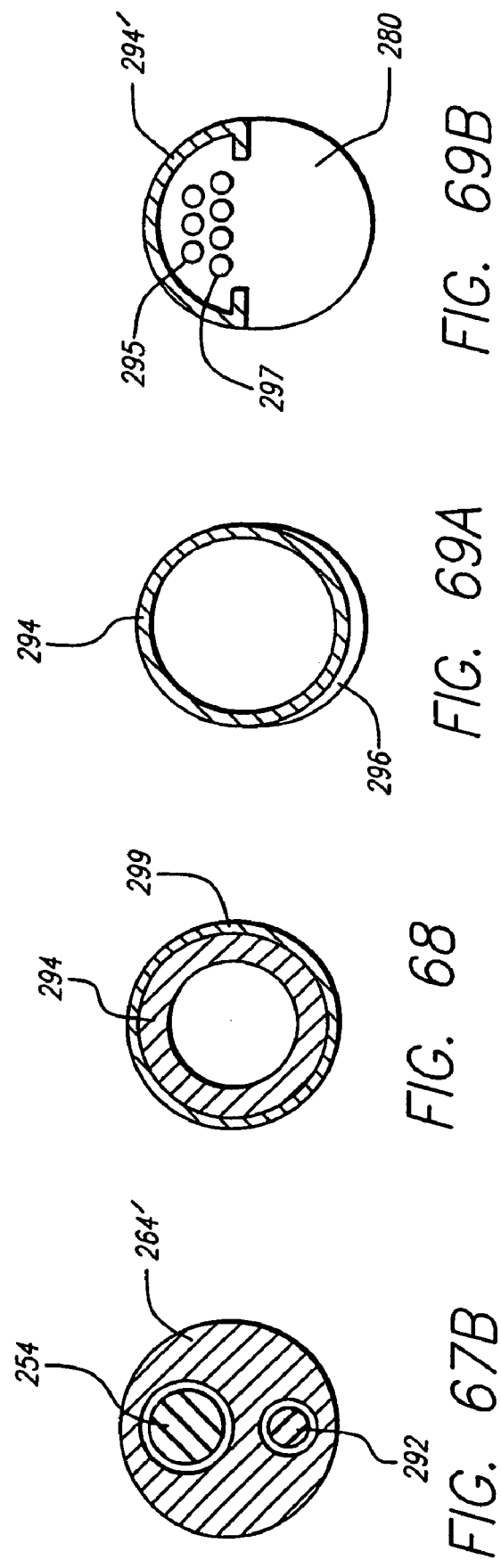

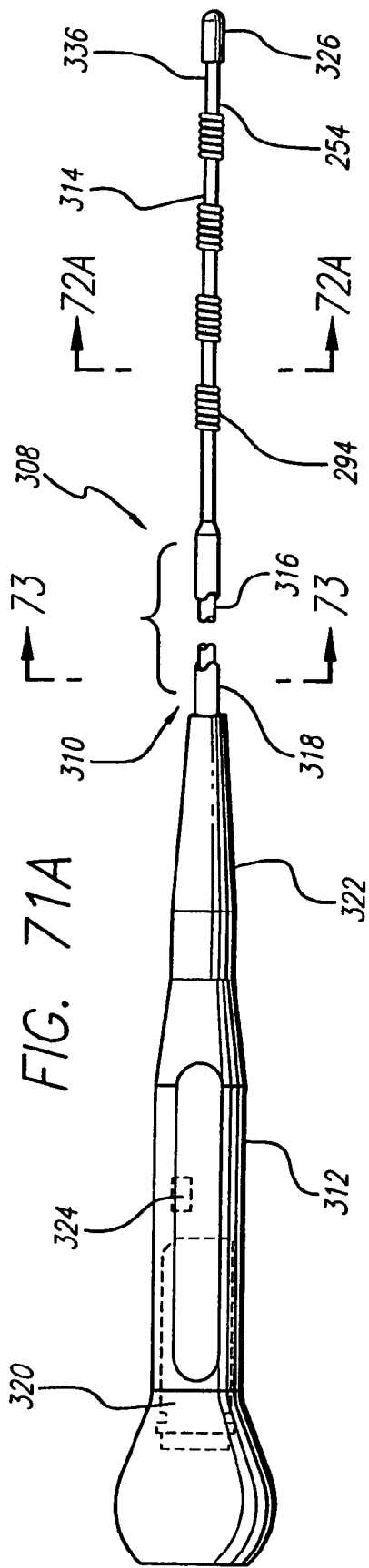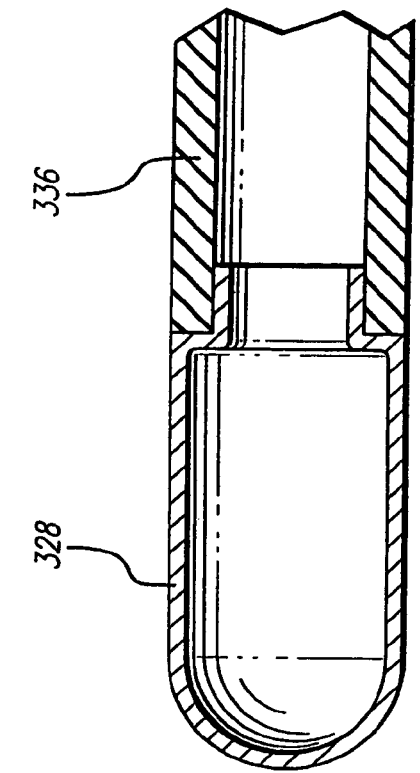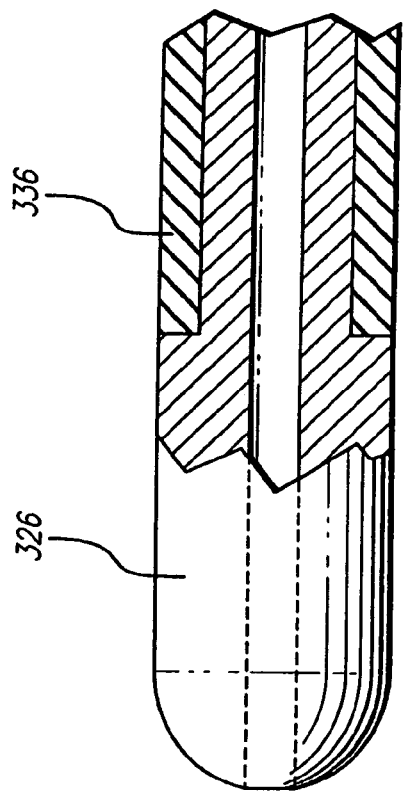
FIG. 71A
FIG. 71C
FIG. 71B

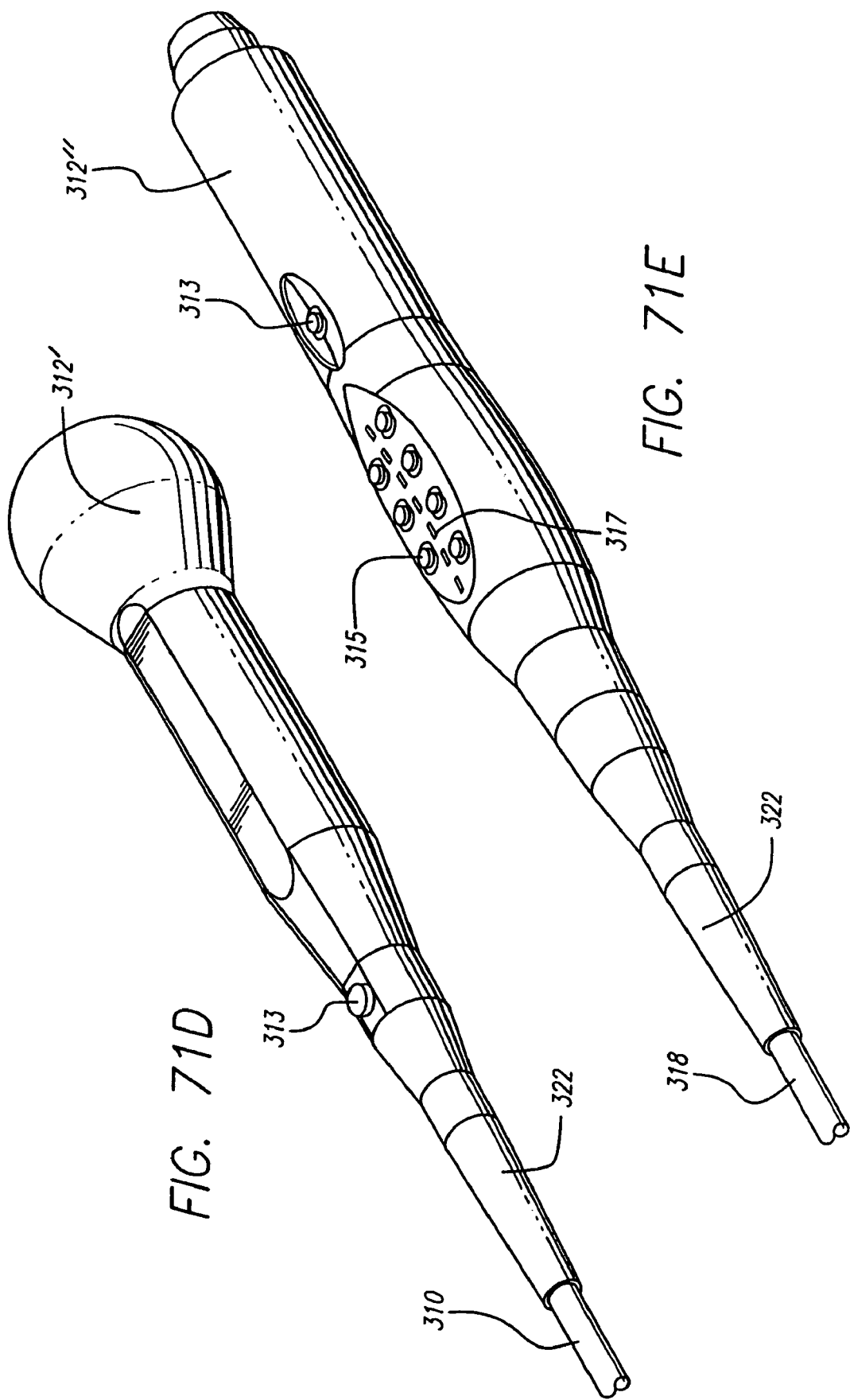

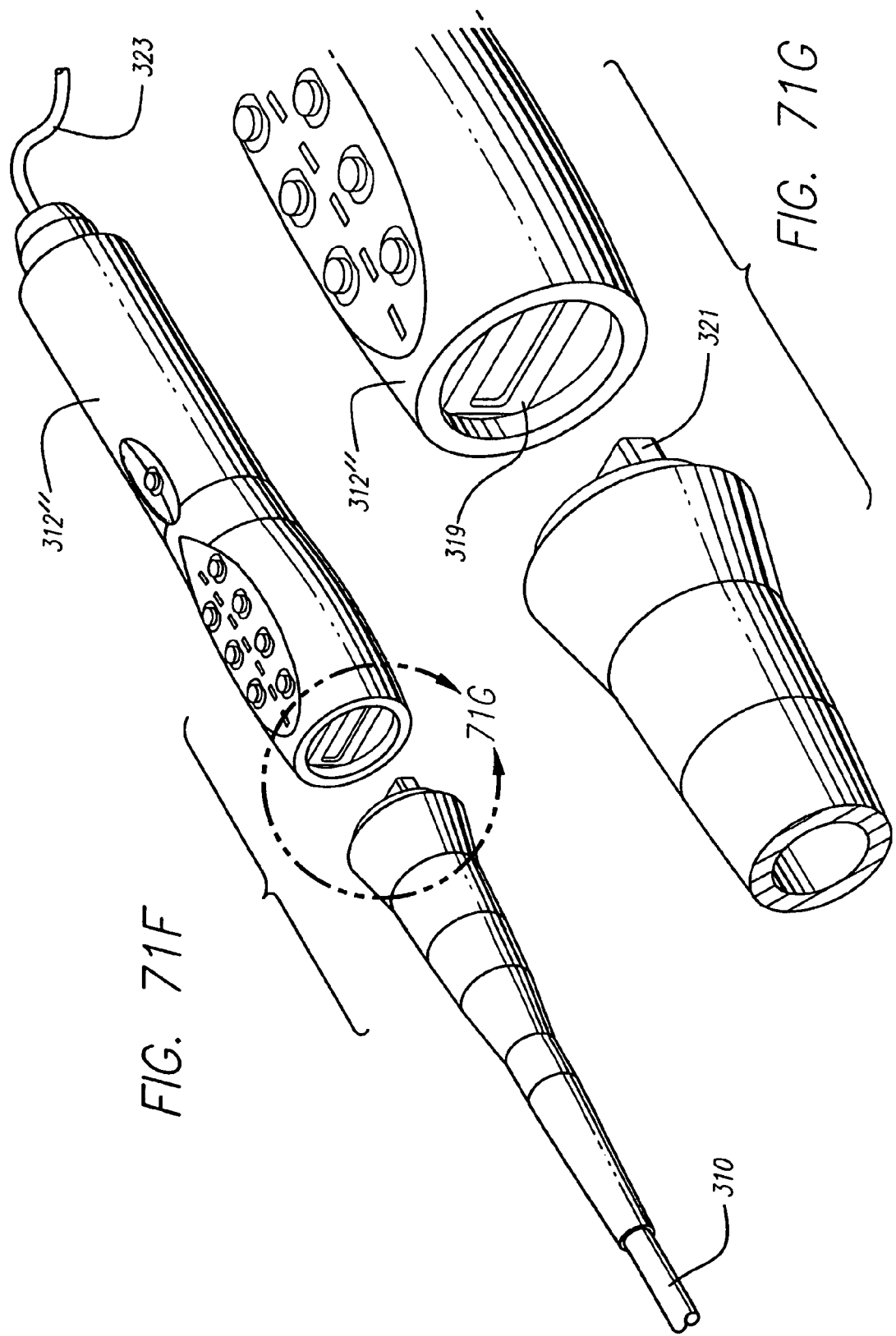

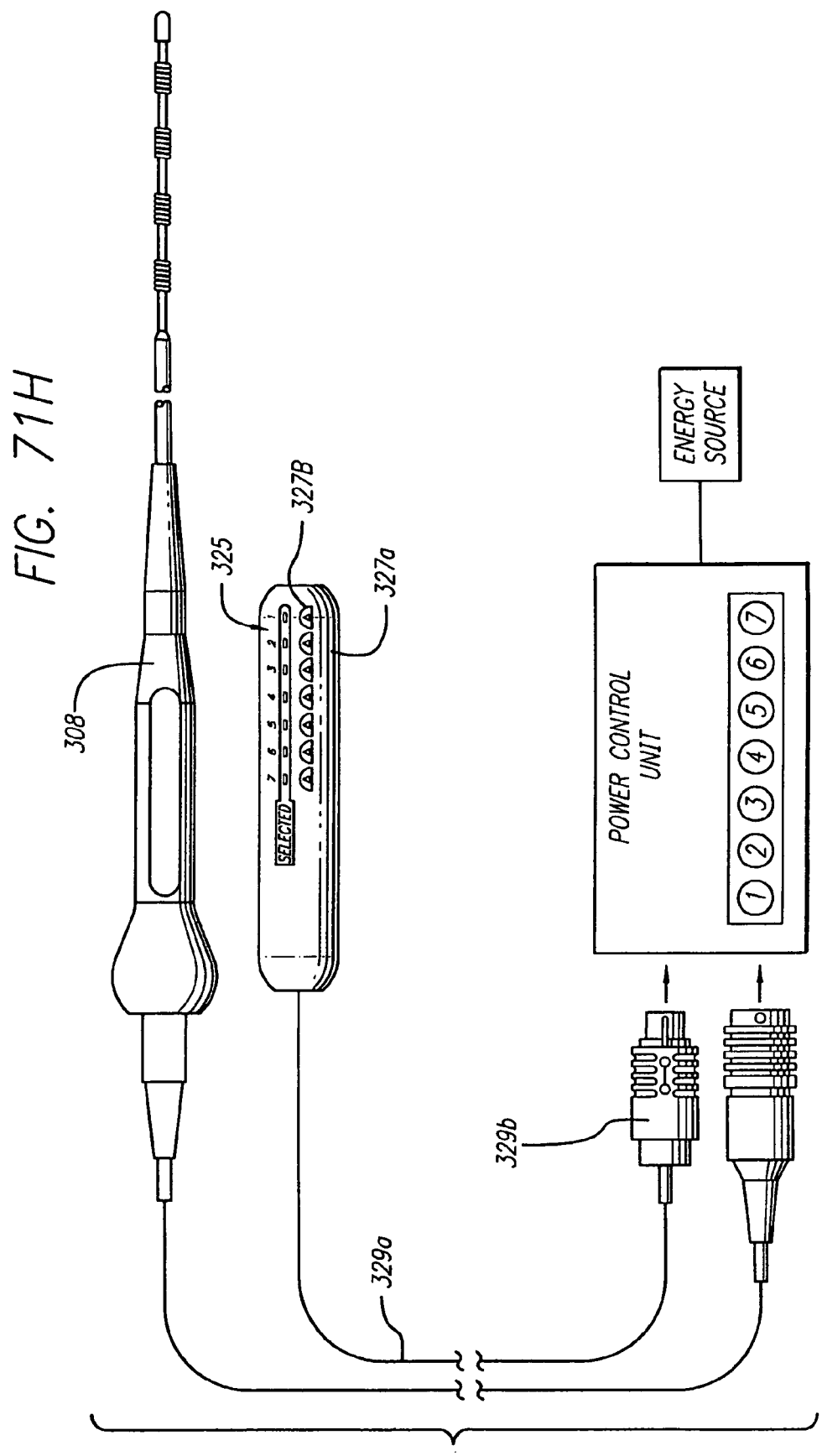

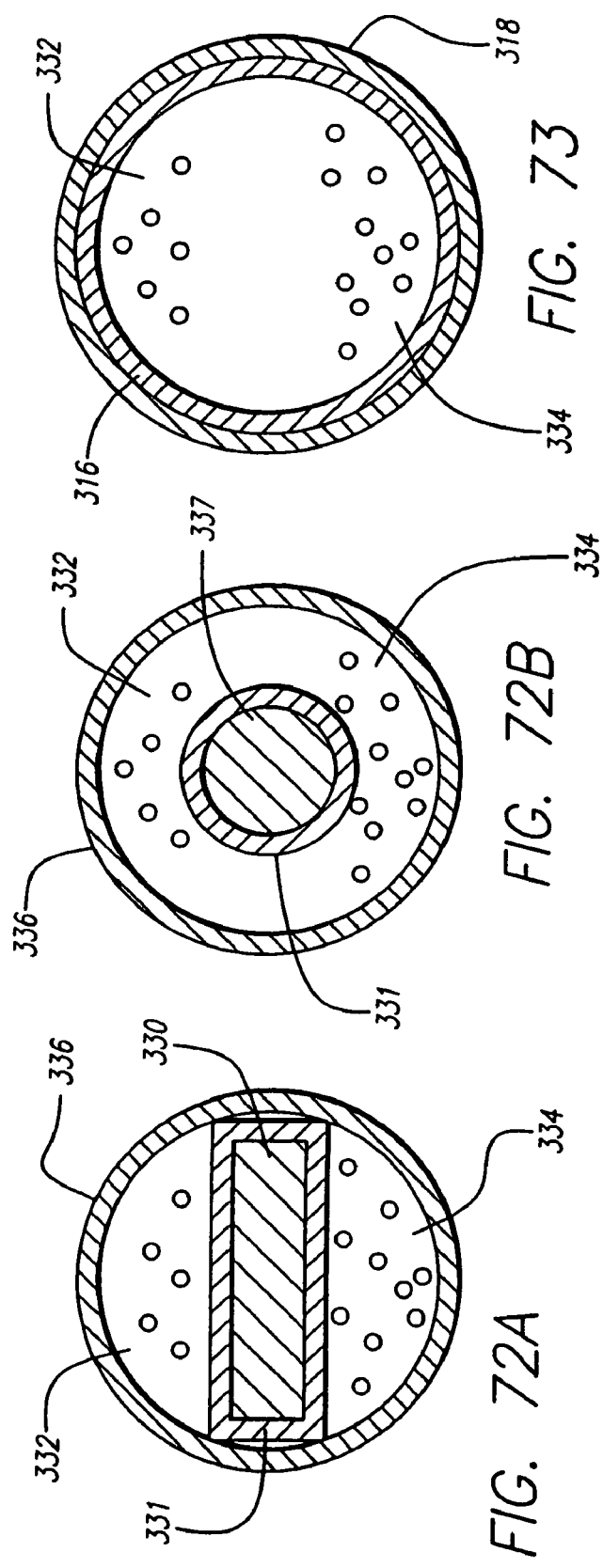
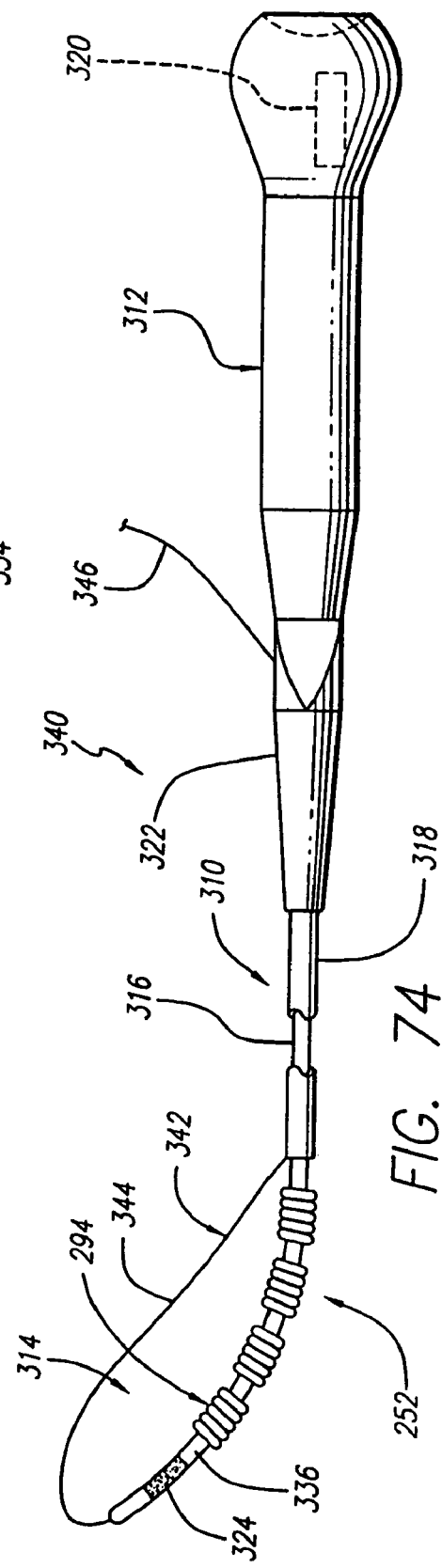
FIG. 73
FIG. 72B
FIG. 72A
FIG. 74

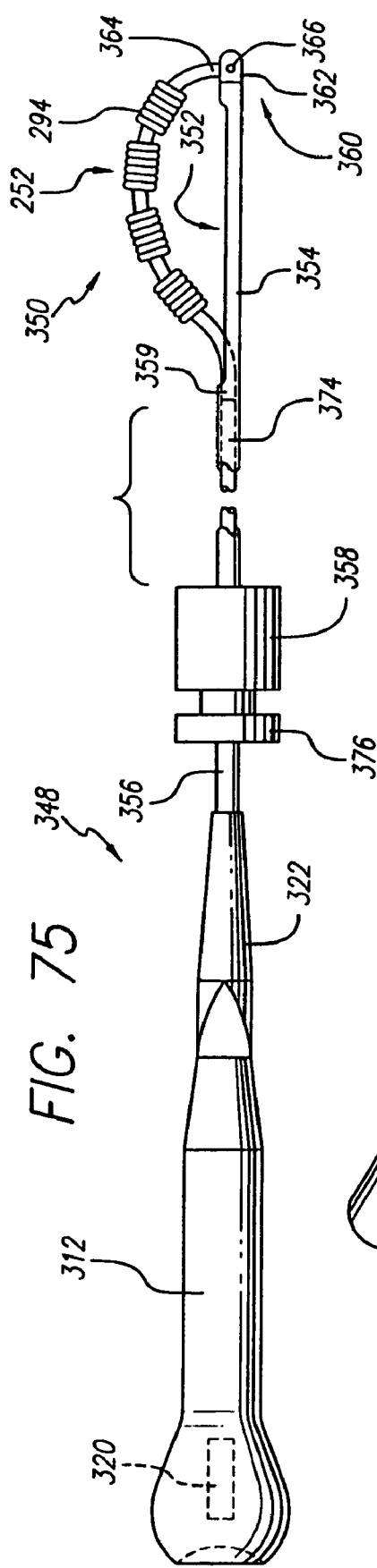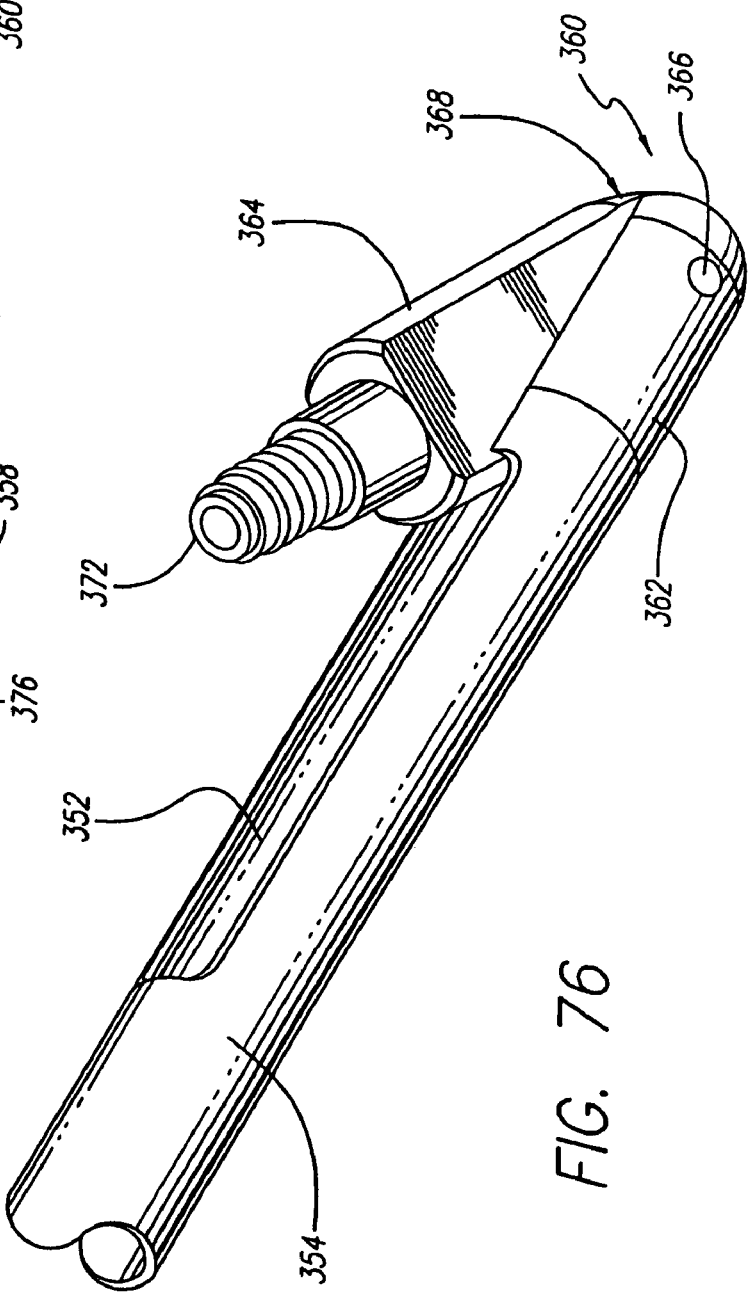

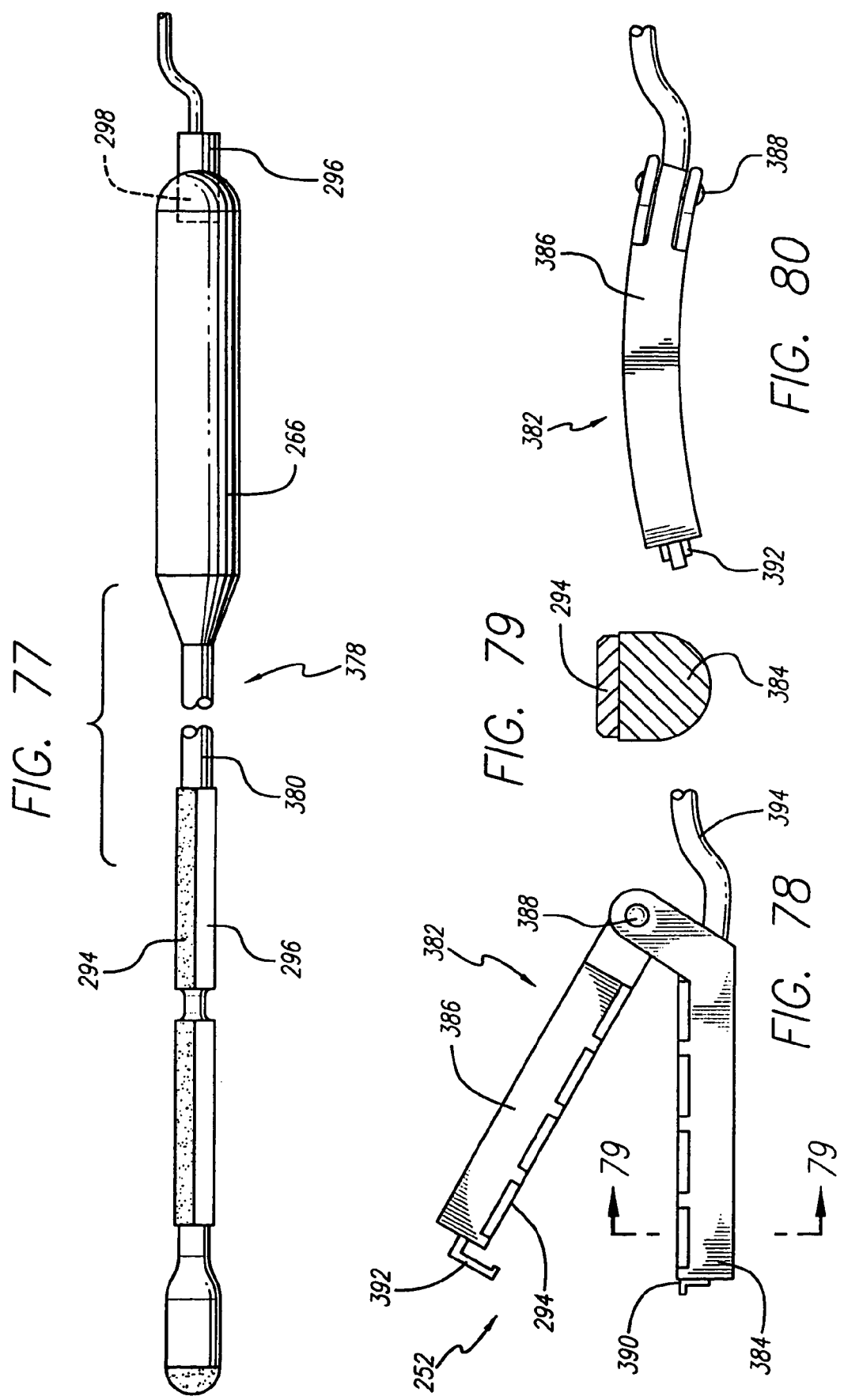

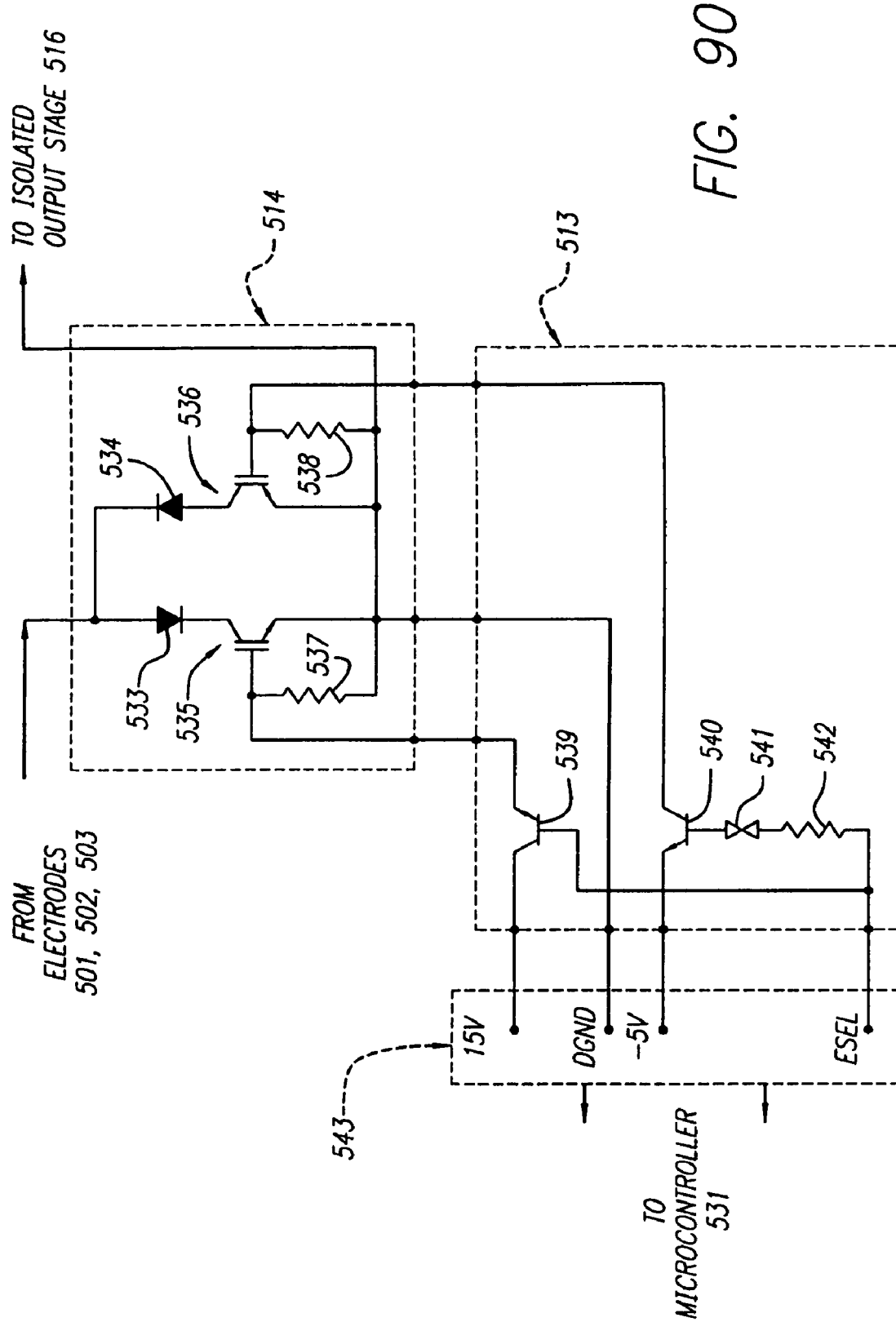

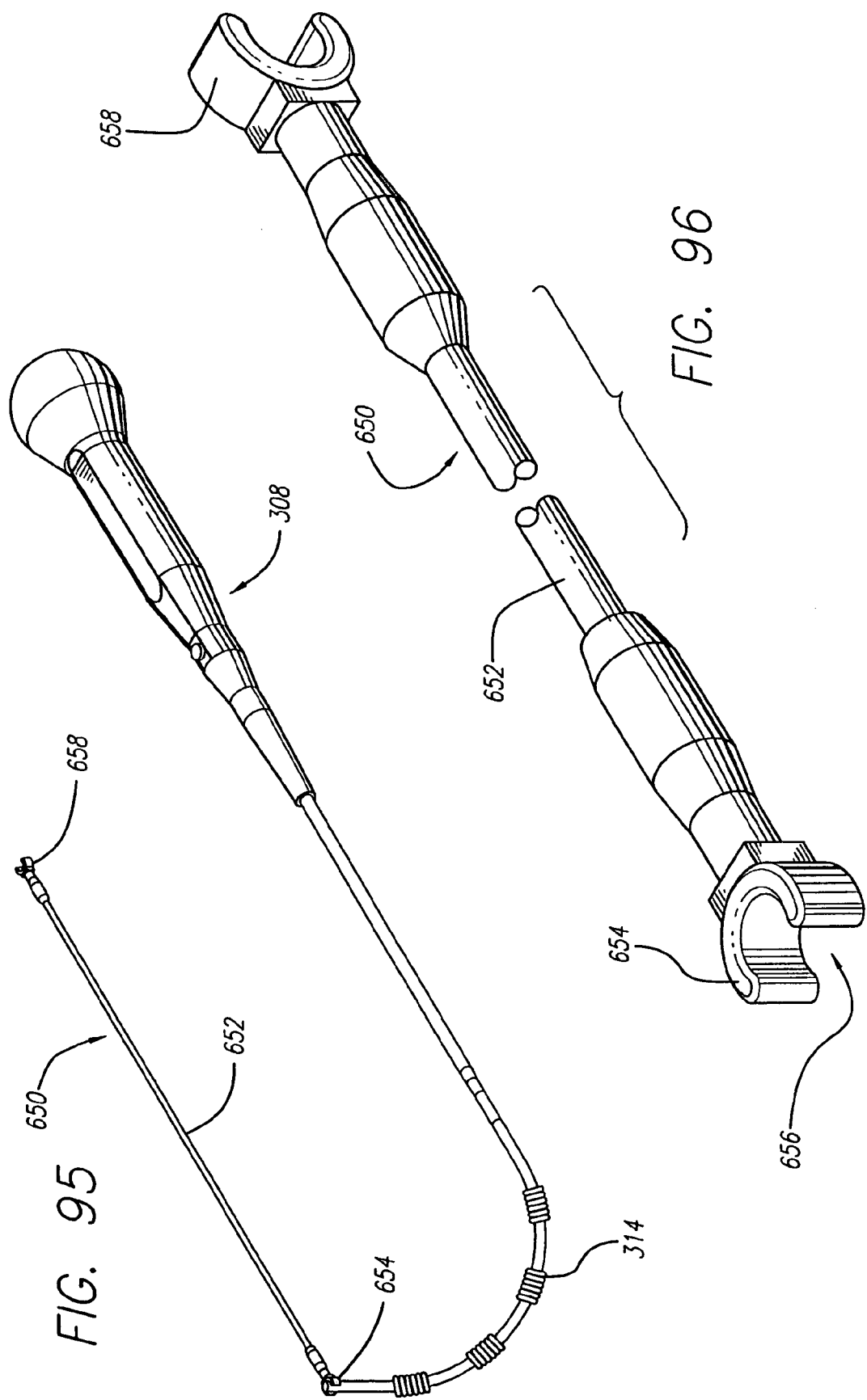

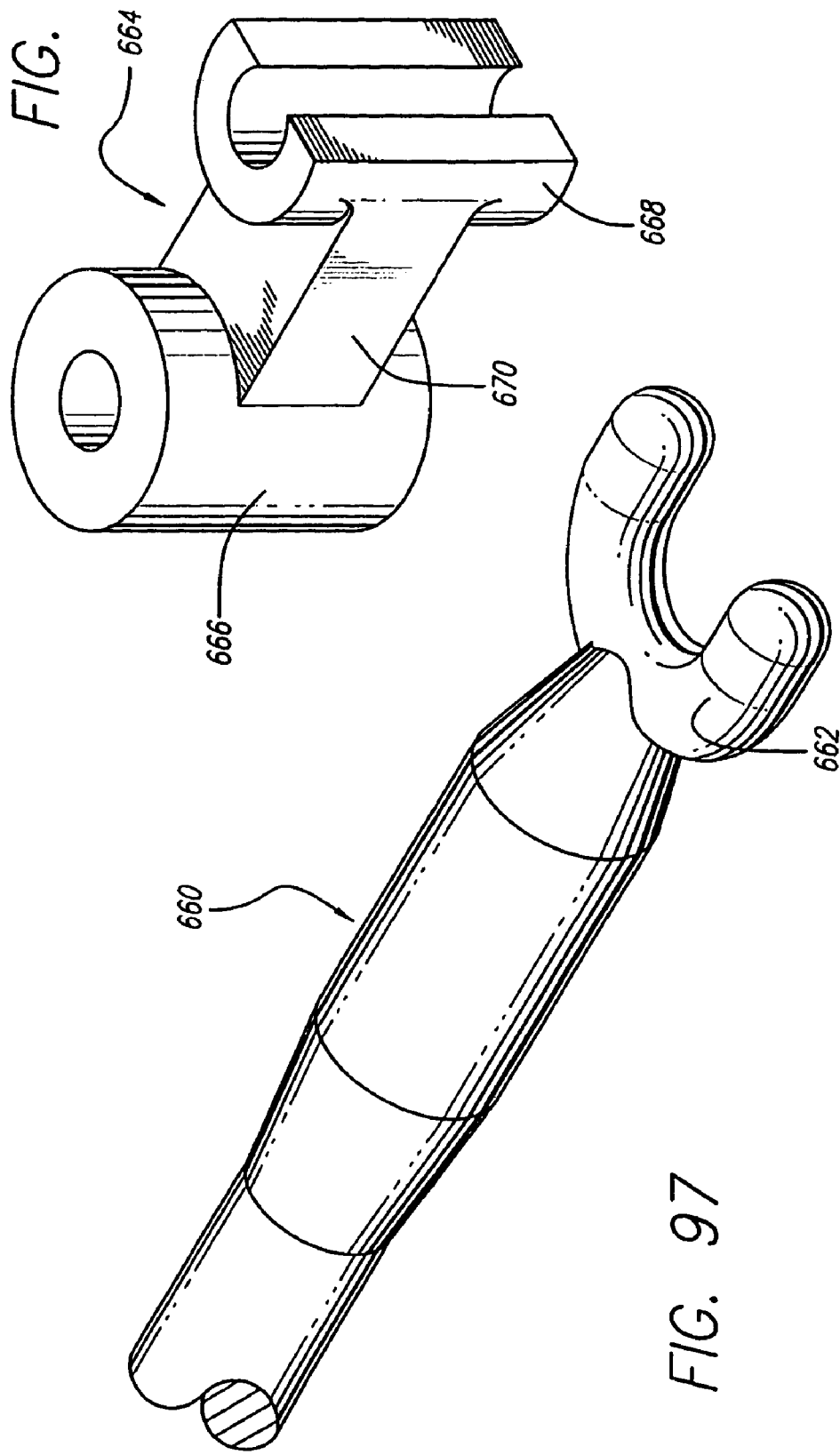

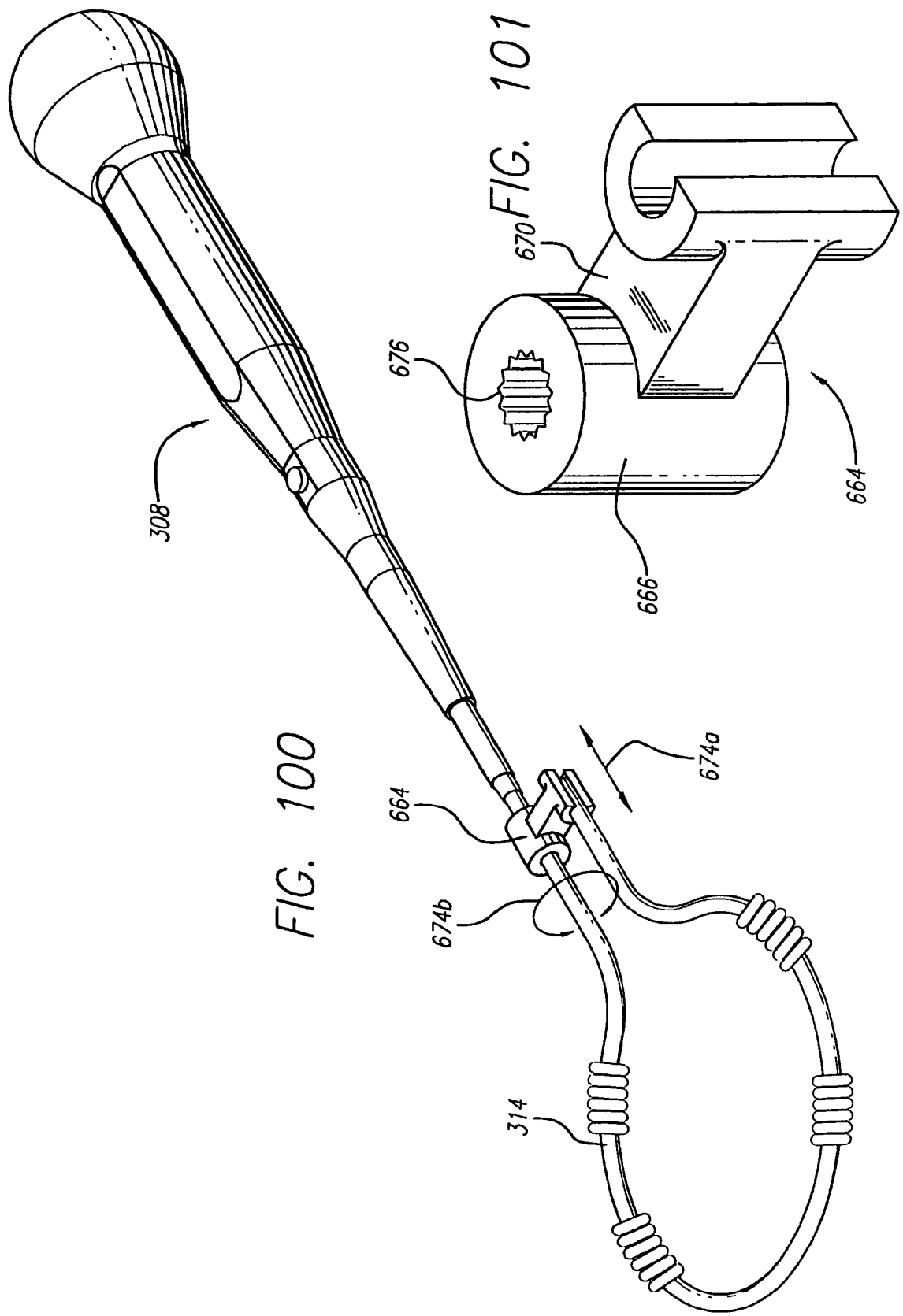

SURGICAL METHOD AND APPARATUS FOR POSITIONING A DIAGNOSTIC OR THERAPEUTIC ELEMENT WITHIN THE BODY

CROSS-REFERENCE TO RELATED APPLICATIONS

This application is a continuation of U.S. application Ser. No. 10/160,960, filed May 30, 2002, now U.S. Pat. No. 6,786,905, which is a continuation of U.S. application Ser. No. 09/644,847, filed Aug. 22, 2000, now U.S. Pat. No. 6,425,895, which is a continuation of U.S. application Ser. No. 09/072,872, filed May 5, 1998, now U.S. Pat. No. 6,142,994, which is a continuation-in-part of U.S. application Ser. No. 08/321,424, filed Oct. 11, 1994, now U.S. Pat. No. 5,885,278, which is a continuation-in-part of U.S. application Ser. No. 08/320,198, filed Oct. 7,1994, now abandoned. U.S. application Ser. No. 09/072,872 is also continuation-in-part of U.S. application Ser. No. 08/321,092, filed Oct. 11, 1994, now U.S. Pat. No. 5,836,947; and U.S. application Ser. No. 08/949,117, now U.S. Pat. No. 6,152,920, U.S. application Ser. No. 08/949,083, now abandoned, U.S. application Ser. No. 08/948,729, now abandoned, and U.S. application Ser. No. 08/949,084, now abandoned, each filed Oct. 10, 1997. The specification and claims of each of these applications are incorporated herein by reference.

BACKGROUND OF THE INVENTIONS

1. Field of Invention

The present inventions relate generally to structures for positioning one or more diagnostic or therapeutic elements within the body and, more particularly, to devices which are particularly well suited for treatment of cardiac conditions.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

Although pharmacological treatment is available for atrial fibrillation and flutter, the treatment is far from perfect. For example, certain antiarrhythmic drugs, like quinidine and procainamide, can reduce both the incidence and the duration of atrial fibrillation episodes. Yet, these drugs often fail to maintain sinus rhythm in the patient. Cardioactive drugs, like digitalis, Beta blockers, and calcium channel blockers, can also be given to control the ventricular response. However, many people are intolerant to such drugs. Anticoagulant therapy also combats thromboembolic complications, but does not eliminate them. Unfortunately, pharmacological remedies often do not remedy the subjective symptoms associated with an irregular heartbeat. They also do not restore cardiac hemodynamics to normal and remove the risk of thromboembolism.

Many believe that the only way to really treat all three detrimental results of atrial fibrillation and flutter is to actively interrupt all of the potential pathways for atrial reentry circuits.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive. Thus, despite its considerable clinical success, only a few maze procedures are done each year.

More recently, maze-like procedures have been developed utilizing catheters which can form lesions on the endocardium to effectively create a maze for electrical conduction in a predetermined path. Exemplary catheters are disclosed in commonly assigned U.S. Pat. No. 5,582,609. Typically, the lesions are formed by ablating tissue with an electrode carried by the catheter. Electromagnetic radio frequency ("RF") energy applied by the electrode heats, and eventually kills (i.e. "ablates"), the tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue.

Catheters used to create lesions (the lesions being 3 to 15 cm in length) typically include a relatively long and relatively flexible body portion that has an ablation electrode on its distal end. The portion of the catheter body portion that is inserted into the patient is typically from 23 to 55 inches in length and there may be another 8 to 15 inches, including a handle, outside the patient. The proximal end of the catheter body is connected to the handle which includes steering controls. The length and flexibility of the catheter body allow the catheter to be inserted into a main vein or artery (typically the femoral artery), directed into the interior of the heart, and then manipulated such that the ablation electrode contacts the tissue that is to be ablated. Fluoroscopic imaging is used to provide the physician with a visual indication of the location of the catheter.

Atrial appendages are primary potential sources of thrombus formation. The atrial appendages are especially important in the transport of blood because they have a sack-like geometry with a neck potentially more narrow than the pouch. In this case, contraction of the appendage is essential to maintain an average absolute blood velocity high enough to eliminate potential stasis regions which may lead to thrombus formation.

In the maze procedure performed through open heart surgery, the typical access points into the interior of the atria are the atrial appendages. Therefore, at the conclusion of the surgical procedure, the region occupied by the atrial appendages is eliminated by surgically removing the appendages. This mitigates subsequent problems resulting from blood stasis in the atrial appendages as well as from electrical isolation of the appendages from the rest of the atria. However, as noted above, open heart surgery is very expensive and the incision based maze procedure is difficult to perform. Although catheter-based procedures do not admit themselves to surgical removal of the appendages, catheter-based procedures and apparatus have been recently developed which reposition the atrial appendages, affix them in an altered position and/or fuse the walls of the appendages to one another to isolate the appendages, reduce stasis regions and ultimately thrombus formation. Such procedures and apparatus are disclosed in commonly assigned U.S. application Ser. No. 08/880,711, filed Jun. 23, 1997, which is a File Wrapper Continuation of U.S. application Ser. No. 08/480,200, filed Jun. 7, 1995, entitled "Atrial Appendage Stasis Reduction Procedures and Devices" and incorporated herein by reference. One of these procedures involves the use of a catheter having a lasso which is tightened around the appendage. RF energy is then transmitted to the appendage by way of the lasso to thermally fuse the walls of the appendage to one another, thereby isolating the appendage.

It is believed the treatment of atrial fibrillation and flutter requires the formation of long, thin lesions of different lengths and curvilinear shapes in heart tissue. Such long, curvilinear lesion patterns require the deployment within the heart of flexible ablating elements having multiple ablating regions. The formation of these lesions by ablation can provide the same therapeutic benefits that the complex incision patterns that the surgical maze procedure presently provides, but without invasive, open heart surgery.

With larger and/or longer multiple electrode elements comes the demand for more precise control of the ablating process. The delivery of ablating energy must be governed to avoid incidences of tissue damage and coagulum formation. The delivery of ablating energy must also be carefully controlled to assure the formation of uniform and continuous lesions, without hot spots and gaps forming in the ablated tissue.

The task is made more difficult because heart chambers vary in size from individual to individual. They also vary according to the condition of the patient. One common effect of heart disease is the enlargement of the heart chambers. For example, in a heart experiencing atrial fibrillation, the size of the atrium can be up to three times that of a normal atrium.

Catheter-based ablation and atrial appendage isolation have proven to be a significant advance over the conventional open heart surgery based approaches. Nevertheless, the inventors herein have determined that further improvements are possible.

For example, and with respect to ablation procedures in particular, the inventors herein have determined that it can be quite difficult to accurately position an ablation electrode on the endocardium surface by manipulating the distal end of a relatively long catheter body from a remote handle. This is especially true with respect to left atrial sites. The present inventors have also determined that fluoroscopy is a somewhat inaccurate method of visualizing the ablation electrodes during positioning and when determining whether the electrodes are in proper contact with tissue.

Additionally, a primary goal of any ablation procedure is to create contiguous lesions (often long, curvilinear lesions) without over-heating tissue and causing coagulum and charring. Tissue ablation occurs at 50° C., while over-heating occurs at 100° C. The present inventors have further determined that it can be difficult to produce tissue contact that will accomplish this result with an electrode mounted on the distal end of a relatively long catheter. This is especially true in those procedures where an electrode on the distal tip of the catheter is dragged along the tissue. Such dragging also makes accurate placement of the electrode very difficult. Other shortcomings identified by the present inventors concern the convective cooling effects of the blood pool on the electrodes. For example, the system power requirements must be high enough to compensate for the heat losses due to convective cooling.

One proposed method of solving the over-heating problems associated with conventional ablation catheters is the so-called "cooled tip" approach. Here, the tissue surface is cooled with a saline solution. Although the saline is somewhat useful in keeping the surface temperature below the over-heating temperature, the sub-surface tissue temperature can still rise well above 100° C. Such temperatures will cause gas within the sub-surface tissue to expand. Ultimately, the tissue will tear or pop, which will result in perforations of the epicardial surface and/or the dislodging of chunks of tissue that can cause strokes.

Turning to atrial appendage isolation, the present inventors have determined that catheter-based procedures suffer from many of the same disadvantages discussed above, such as those concerning positioning and visualization. Additionally, the inventors herein have determined that the lasso can bunch up the tissue when the lasso is tightened and that tissue fusion would be improved if this bunching could be avoided.

With respect to energy control, conventional ablation devices include controls that are located either on the RF energy source, or on a foot pedal. The inventors herein have determined that such arrangements are inconvenient and can make it difficult to control power during a surgical procedure.

Turning to surgical procedures in general, one problem associated with many surgical procedures is excessive bleeding. For example, a high level of bleeding is often associated with the removal of liver lobes and certain cancerous tumors. The inventors herein have determined that present surgical methods could be improved in the area of blood loss.

SUMMARY OF THE INVENTIONS

Accordingly, the general object of the present inventions is to provide an apparatus for positioning an operative element (such as an ablation electrode) within the body which avoids, for practical purposes, the aforementioned problems. In particular, one object of the inventions is to provide tissue ablation systems and methods providing beneficial therapeutic results without requiring highly invasive surgical procedures. Another objective of the inventions is to provide systems and methods that simplify the creation of complex lesions patterns in soft tissue, such as myocardial tissue in the heart.

In order to accomplish these and other objectives, certain embodiments of one of the present inventions include an electrode support structure carried at the distal end of a guide body. The support structure includes a bendable stylet extending along an axis outside the distal end of the guide body. The structure also includes at least one flexible spline leg having a near end attached to the distal end of the guide body and a far end extending beyond the distal end of the guide body and attached to the bendable stylet. The spline leg is normally flexed between the distal guide body end and the bendable stylet in a first direction that extends along and radially outward of the axis of the stylet. At least one electrode element is on the flexible spline. The structure further includes a control element to apply tension to the stylet. The tension bends the stylet, thereby flexing the spline leg in a second direction.

The flexure of the spline leg in the first direction facilitates intimate contact between the electrode element and tissue. The additional flexure by the stylet of the spline leg in the second direction makes possible the creation of a diverse number of additional shapes and tissue contact forces.

In accordance with another embodiment of one of this invention, an electrode support structure is provided that, in addition to bending the stylet, includes another control element that moves the stylet along its axis to increase or decrease flexure of the spline leg in the first direction. This additional control over the flexure of the spline leg further enhances intimate contact against tissue, regardless of variations in the dimensions of the surrounding tissue region.

In accordance with another embodiment of this invention, an electrode support structure is provided that includes a malleable stylet. The physician imparts a desired flexure to the spline leg in the second direction by bending the malleable stylet. Alternatively, an electrode support structure is provided in which the spline leg itself is malleable.

Structures that embody the features of this invention make possible the creation of diverse number of shapes and contact forces to reliably achieve the type and degree of contact desired between electrode elements and targeted tissue areas, despite physiologic differences among patients.

Another aspect of this invention is associated with structures and methods for ablating tissue in a heart. The structures and methods include a probe for deployment within the heart. The probe carries at least one elongated flexible ablation element to which a bendable stylet is attached. The structures and method apply tension to bend the stylet. The bending of the stylet flexes the ablation element into a curvilinear shape along the contacted tissue region. By transmitting ablation energy to the ablation electrode while flexed in the curvilinear shape and in contact with the tissue region, the structures and methods make possible the formation of curvilinear lesion patterns in heart tissue.

In order to accomplish the above-described and other objectives, a surgical device in accordance with one embodiment of another one of the present inventions includes a relatively short shaft, a bendable spline assembly associated with the distal end of the shaft and having a predetermined configuration, the spline assembly being adapted to collapse in response to external forces and expand when the forces are removed, and an operative element associated with the bendable spline. Optionally, a substantially tubular member may be positioned around the shaft. Movement of the substantially tubular member over the spline assembly will cause the spline assembly to collapse, while the spline assembly will expand to the predetermined configuration in response to a retraction of the substantially tubular member.

In order to accomplish above-described and other objectives, an soft tissue coagulation probe in accordance with one embodiment of one of the inventions includes a relatively short shaft defining a distal end and a proximal end, a handle associated with the proximal end of the shaft, and at least one soft tissue coagulation electrode associated with the shaft and located in spaced relation to the handle.

In order to accomplish above-described and other objectives, a surgical device in accordance with another embodiment of this invention includes a relatively stiff shaft, a handle associated with the proximal end of the shaft, and a distal tip assembly associated with the distal end of the shaft, the distal tip assembly including a distal member, which is flexible and/or malleable, and an operative element carried by the distal member.

In order to accomplish this and other objectives, a surgical device in accordance with another embodiment of this invention includes a shaft, a relatively stiff tubular member positioned around a predetermined portion of the shaft and movable relative thereto, a distal tip assembly associated with the distal end of the shaft and including a flexible distal member and an operative element carried by the distal member, and a pivot assembly associated with the distal end of the tubular member and a distal portion of the tip assembly.

There are many advantages associated with these inventions. For example, the above-described embodiments of this invention may be used in a method of treating atrial fibrillation wherein access to the heart is obtained by way of a thoracostomy. Here, the operative element is an ablation electrode. Such a method may also be used to treat atrial fibrillation during mitral valve surgery wherein access to the heart is obtained through a thoracostomy, thoracotomy or median sternotomy.

The relatively short shaft and manner of insertion allows the ablation electrode to be easily inserted into the atrium and visually guided to the desired location. Thus, the ablation electrodes in the present device do not have to be guided by manipulating the relatively long shaft of an endovascular catheter. This makes the positioning of the electrodes within the heart easier and more accurate. Endocardial visualization is also improved because surgical methods employing the present device allow the endocardium to be viewed directly with the naked eye, a fiberoptic camera or other imaging modalities. This eliminates the need for fluoroscopic images and reduces the amount of radiation required, as compared to catheter-based procedures. Moreover, the shaft in the present device can be relatively stiff, as compared to a catheter shaft, because the present shaft does not have to travel through the tortuous vascular path to the heart. Along with the relatively short length of the present shaft, the additional stiffness enhances torque transmission and provides superior and more reliable electrode-endocardium contact force.

Surgical devices in accordance with this invention may also be used during procedures, such as valve replacement where the patient is on cardiopulmonary bypass, to create tissue lesions. During bypass, the electrodes elements will not be in contact with the blood pool and, accordingly, will not be affected by the convective cooling.

Patients can only be on bypass for a period of approximately four hours. Long bypass times are associated with increased morbidity and mortality. Thus, all procedures performed during bypass must be rapidly completed. Surgical devices in accordance with the present invention may include a series of temperature controlled electrodes that allow a long lesion to be created in rapid fashion, i.e. in approximately 30 to 120 seconds. The ability of the present surgical devices and techniques to create lesions rapidly allows procedures to be performed during bypass that, heretofore, could not due to the time constraints. For example, a conventional surgical maze procedure takes approximately 12 hours to complete (note that a portion of the procedure is performed while the patient is not on bypass), while such a procedure may be completed in approximately 5 to 15 minutes with the present devices and methods.

In accordance with another advantageous aspect of this invention, the shaft and/or sheath (if present) may be formed from a malleable material that a physician can bend into a desired configuration and remain in that configuration when released. Although malleable, the stiffness of such material must be at least such that the shaft and/or sheath (if present) will not bend under the forces applied thereto during a surgical procedure. Alternatively, or in addition, the distal end of the device may also be malleable, thereby allowing the physician to bend the distal end of the device into a shape corresponding to the bodily structure to be acted upon. This is particularly important in endocardial applications because the endocardial surface is typically non-uniform with ridges and trabeculae residing in the right and left atria. There are also dramatic differences between endocardial surface morphology from patient to patient and from lesion location to lesion location. To create contiguous lesions with a surgical approach, the device must either distend the atria to flatten out the non-uniformities, or the probe must be configured to conform to the atrial surface. There are, however, some regions where the atria cannot be distended to a flat state because of trabeculae, orifices, and ridges. A surgeon can observe the atrial surface and bend the present malleable device so as to conform thereto. The distal end may, instead, be spring-like or even rigid if the application so requires.

In order to accomplish the above-identified and other objectives, a surgical device in accordance with one embodiment of another one of the present inventions includes a handle having at least one movable handle member, first and second support members operably connected to the handle, at least one of the support members being movable with respect to the other support member in response to movement of the at least one movable handle member, and at least one ablation electrode associated with the first support member.

There are many advantages associated with this invention. By way of example, this invention is especially useful in a method of isolating an atrial appendage. Access to the atrium may be obtained by, for example, a thoracostomy and the appendage may be captured between the support members. RF energy is then applied to the captured portion of the appendage to thermally fuse the walls of the appendage to one another. This method provides better heating and fusing than the lasso catheter-based approach because the tissue is not bunched up when captured between the support members, as it is when the lasso is tightened. Additionally, the disadvantages associated with the use of catheters in general are also avoided.

A surgical clamp in accordance with one embodiment of another of the present inventions includes first and second clamp members, and at least one electrode associated with at least one of the clamp members. The clamp may be used to isolate an atrial appendage in a manner similar to that described in the preceding paragraph with the same advantageous results. Thereafter, the clamp may be either removed or left in place.

A surgical device in accordance one embodiment of another of the present inventions includes an energy source, at least one energy transmission device, and a handle including an energy control device coupled to the energy source and to the at least one energy transmission device. The energy control device is adapted to selectively control the transmission of energy from the energy source to the at least one energy transmission device. Because the energy control device is located on the handle, which is necessarily grasped by the physician during surgical procedures, the present surgical device provides more convenient energy control than that found in conventional devices.

Alternatively, and in accordance with one embodiment of another of the present inventions, energy control may be accomplished through the use of a remote energy control device that is connected to power unit, but located in close proximity to the patient or otherwise within the sterile zone of an operating room. Such an arrangement also provides more convenient energy control than that found in conventional devices.

Additionally, whether the power control interface is located on the handle of a surgical probe or on a remote control device, the power control aspect of the overall electrophysiological system can be more conveniently brought into the sterile zone because both the present surgical probe and remote control device are both readily sterilizable. Conventional power control interfaces, on the other hand, are part of a power control unit that is not readily sterilizable.

To further improve tissue contact, a pressure application probe in accordance with one embodiment of another of the present inventions may be used in conjunction with a probe having an energy transmission device on a support member. The pressure application probe includes an elongate main body portion and an engagement device adapted to releasably engage the support member. The pressure application probe can be used by the physician to insure that sufficient tissue contact is realized prior to energy transmission.

A coupling device in accordance with another of the present inventions can also be used in conjunction with a probe having an energy transmission device on a support member. One embodiment of the coupling device includes a base member adapted to be removably secured to a first portion of the probe's flexible support member and an engagement device connected to the base member and adapted to be removably secured to a second portion of the flexible support member. The coupling device enables a physician to form a distal loop in the support member when desired, thereby increasing the flexibility of the probe.

In order to reduce the blood loss associated certain surgical procedures, a surgical method in accordance with another of the present inventions includes the steps of coagulating soft tissue and then forming an incision is the coagulated tissue. If the incision is no deeper than the coagulation, the incision will not result in significant bleeding. This process can be repeated until an incision of the desired depth is achieved.

The above described and many other features and attendant advantages of the present invention will become apparent as the invention becomes better understood by reference to the following detailed description when considered in conjunction with the accompanying drawings.

BRIEF DESCRIPTION OF THE DRAWINGS

Detailed description of preferred embodiments of the invention will be made with reference to the accompanying drawings.

FIG. 7 is an elevation view of a half-loop structure for supporting multiple electrodes.

FIG. 8 is an elevation view of a composite loop structure for supporting multiple electrodes comprising two circumferentially spaced half-loop structures.

FIG. 9 is an elevation view of a composite loop structure comprising two full-loop structures positioned ninety degrees apart.

FIG. 10 is an elevation view, with parts broken away, of multiple electrode elements comprising segmented rings carried by a loop support structure.

FIG. 11a is an enlarged view, with parts broken away, of multiple electrode elements comprising wrapped coils carried by a loop support structure.

FIG. 11b is an elevation view, with parts broken away, of multiple electrode elements comprising wrapped coils carried by a loop support structure.

FIG. 13 is a plan view of a full-loop structure for supporting multiple electrode elements having an associated center stylet attached to a remote control knob for movement to extend and distend the full-loop structure.

FIG. 14 is a side section view of the remote control knob for the center stylet shown in FIG. 13.

FIG. 15 is a plan view of the full-loop structure shown in FIG. 13, with the control knob moved to extend the full-loop structure.

FIG. 16 is a plan view of a full-loop structure shown in FIG. 13, with the control handle moves to distend the full-loop structure.

FIGS. 23a and 23b are side elevation views showing the operation of the steering mechanism in bending the full-loop structure, respectively, to the left and to the right.

FIG. 24 is a largely diagrammatic, perspective view of the full-loop structure bent to the right, as also shown in side elevation in FIG. 23b.

FIG. 25 is a plan view of the full-loop structure shown in FIG. 20 and the associated remote control knob for extending and distending as well as bending the full-loop structure.

FIG. 26 is a side section view, taken generally along lines 26—26 in FIG. 25, of the control knob for extending and distending as well as bending the full-loop structure.

FIG. 27 is a largely diagrammatic, perspective view of the full-loop structure when distended and bent to the right.

FIG. 28 is a largely diagrammatic, perspective view of a half-loop structure with steerable center stylet bent to the right.

FIG. 29 is a plan, partially diagrammatic, view of a full-loop structure for supporting multiple electrode elements having a movable spline leg attached to a remote control knob for movement to extend and distend the full-loop structure.

FIG. 30a is a section view, taken generally along line 30a–30a in FIG. 29, of the interior of the catheter body lumen, through which the movable spline leg passes.

FIG. 30b is a side section view of an alternative way of securing the full-loop structure shown in FIG. 29 to the distal end of the catheter tube.

FIG. 31 is a plan, partially diagrammatic view of the full-loop structure shown in FIG. 29 being extended by pulling the movable spline leg inward.

FIGS. 32 and 33 are plan, partially diagrammatic views of the full-loop structure shown in FIG. 29 being distended by pushing the movable spline leg outward.

FIGS. 34 and 35 are largely diagrammatic views of the full-loop structure shown in FIG. 29 being distended by pushing the movable spline leg outward while deployed in the atrium of a heart.

FIGS. 36, 37, and 38 are plan, partially diagrammatic views of a full-loop structure for supporting multiple electrode elements having two movable spline legs attached to remote control knobs for coordinated movement to extend and distend the full-loop structure.

FIG. 39a is a plan view of a full-loop structure for support multiple electrode elements having a smaller, secondary loop structure formed in one spline leg.

FIG. 39b is a side view of the full-loop structure shown in FIG. 39a, showing the smaller, secondary loop structure.

FIG. 40b is a top section view of the base of the full-loop structure shown in FIG. 40a.

FIGS. 41, 42, and 43 are plan, partially diagrammatic, views of a bifurcated full-loop-structure for supporting multiple electrode elements having movable half-loop structures to extend and distend the bifurcated full-loop structure.

FIGS. 44 and 45 are plan, partially diagrammatic, views of an alternative form of a bifurcated full-loop structure for supporting multiple electrode elements having movable center ring to extend and distend the bifurcated full-loop structure.

FIG. 46 is a plan, partially diagrammatic, views of an alternative form of a bifurcated full-loop structure for supporting multiple electrode elements having both a movable center ring and movable spline legs to extend and distend the bifurcated full-loop structure.

FIGS. 47, 48, and 49 are plan, partially diagrammatic, views of another alternative form of a bifurcated full-loop structure for supporting multiple electrode elements having movable half-loop structures to extend and distend the bifurcated full-loop structure.

FIG. 50 is a plan view of a full-loop structure for supporting and guiding a movable electrode element.

FIG. 51 is a side elevation view of the full-loop structure and movable electrode element shown in FIG. 50.

FIG. 52 is an enlarged view of the movable electrode supported and guided by the structure shown in FIG. 50, comprising wound coils wrapped about a core body.

FIG. 53 is an enlarged view of another movable electrode that can be supported and guided by the structure shown in FIG. 50, comprising bipolar pairs of electrodes.

FIG. 54 is a largely diagrammatic view of the full-loop structure and movable electrode element shown in FIG. 50 in use within the atrium of a heart.

FIG. 61 is a top section view of the base of the bundled loop structure shown in FIG. 55.

FIG. 62 is a side, partial section view of a surgical device for positioning an operative element within a patient in accordance with a preferred embodiment of one of the present inventions.

FIG. 63 is an end view of the surgical device shown in FIG. 62.

FIG. 64a is a side view of a surgical device for positioning an operative element within a patient in accordance with another preferred embodiment of one of the present inventions.

FIG. 64b is a partial side view of a portion of the surgical device shown in FIG. 64a.

FIG. 65 is a side, partial section view of a portion of the surgical device shown in FIG. 64a.

FIG. 66 is a side view of a surgical device for positioning an operative element within a patient in accordance with still another preferred embodiment of one of the present inventions.

FIG. 67a is a partial side, cutaway view of a surgical device for positioning an operative element within a patient in accordance with yet another preferred embodiment of one of the present inventions.

FIG. 67b is a section view taken along line 67b—67b in FIG. 67a.

FIG. 68 is a section view showing an operative element coated with regenerated cellulose.

FIG. 69a is a section view showing a partially masked operative element.

FIG. 69b is a section view showing an alternative operative element configuration.

FIG. 70e is a section view taken along line 70e—70e in FIG. 70a.

FIG. 71a is a side view of a surgical device for positioning an operative element within a patient in accordance with a preferred embodiment of one of the present inventions.

FIG. 71b is a side, partial section view of an alternate tip that may be used in conjunction with the device shown in FIG. 71a.

FIG. 71c is a side, section view of another alternate tip that may be used in conjunction with the device shown in FIG. 71a.

FIG. 71d is a perspective view of a probe handle in accordance with a present invention.

FIG. 71e is a perspective view of a probe handle in accordance with another embodiment of present invention.

FIG. 71f is an exploded perspective view of a probe in accordance with one embodiment of a present invention.

FIG. 71g is an enlarged view of a portion of the probe shown in FIG. 71f.

FIG. 71h is a plan view of an electrophysiology system in accordance with one embodiment of a present invention.

FIG. 72a is a section view of the distal portion of the device shown in FIG. 71a taken along line 72a—72a in FIG. 71a.

FIG. 72b a section view of an alternate distal portion for the device shown in FIG. 71a.

FIG. 72c is a side, partial section view of another alternative distal portion for the device shown in FIG. 71a.

FIG. 73 is a section view taken along line 73—73 in FIG. 71a.

FIG. 74 is a side view of a surgical device for positioning an operative element within a patient in accordance with another preferred embodiment of one of the present inventions.

FIG. 75 is a side view of a surgical device for positioning an operative element within a patient in accordance with yet another preferred embodiment of one of the present inventions.

FIG. 76 is a perspective view of a portion of the device shown in FIG. 75.

FIG. 77 is a side view of a surgical device for positioning an operative element within a patient in accordance with still another preferred embodiment of one of the present inventions.

FIG. 78 is a side view of a damp in accordance with a preferred embodiment of one of the present inventions.

FIG. 79 is a section view taken along line 79—79 in FIG. 78.

FIG. 80 is a top view of the clamp illustrated in FIG. 78.

FIGS. 89 and 90 are schematic views of a system for controlling the application of ablating energy to multiple electrodes using multiple temperature sensing inputs.

FIG. 95 is a perspective view of a pressure application probe in accordance with a preferred embodiment of a present invention secured to an operative element supporting probe.

FIG. 96 is an enlarged perspective view of the pressure application probe shown in FIG. 95.

FIG. 97 is a partial perspective view of a pressure application probe in accordance with another preferred embodiment of a present invention.

FIG. 98 is a perspective view of a coupling device in accordance with a preferred embodiment of a present invention.

FIG. 99 is a perspective view showing a pressure application probe and the coupling device shown in FIG. 98 being used in combination with the surgical device shown in FIG. 71a.

FIG. 100 is a perspective view showing the coupling device shown in FIG. 98 being used in combination with the surgical device shown in FIG. 71a.

FIG. 101 is a perspective view of a coupling device in accordance with another preferred embodiment of a present invention.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Bi-Directional Flexible Structures
II. Probe-Type Apparatus
III. Operative Elements
IV. Epicardial Applications of Probe-Type Apparatus
V. Endocardial Applications of Probe-Type Apparatus
VI. Other Surgical Applications
VII. Apparatus that Apply a Clamping Force
VIII. Applications of Apparatus that Apply a Clamping Force
IX. Power Control The section titles and overall organization of the present detailed description are for the purpose of convenience only and are not intended to limit the present invention.

This specification discloses a number of electrode structures, mainly in the context of cardiac ablation, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus and other solid organs.

I. Bi-Directional Flexible Structures

The exemplary structures, systems, and techniques illustrated in this Section are discussed in the context of catheter-based cardiac ablation. Nevertheless, it should be appreciated that the structures, systems, and techniques are applicable for use in other tissue ablation applications, including those that are not necessarily catheter-based.

A. Loop Support Structures for Multiple Electrodes

Figure 1:
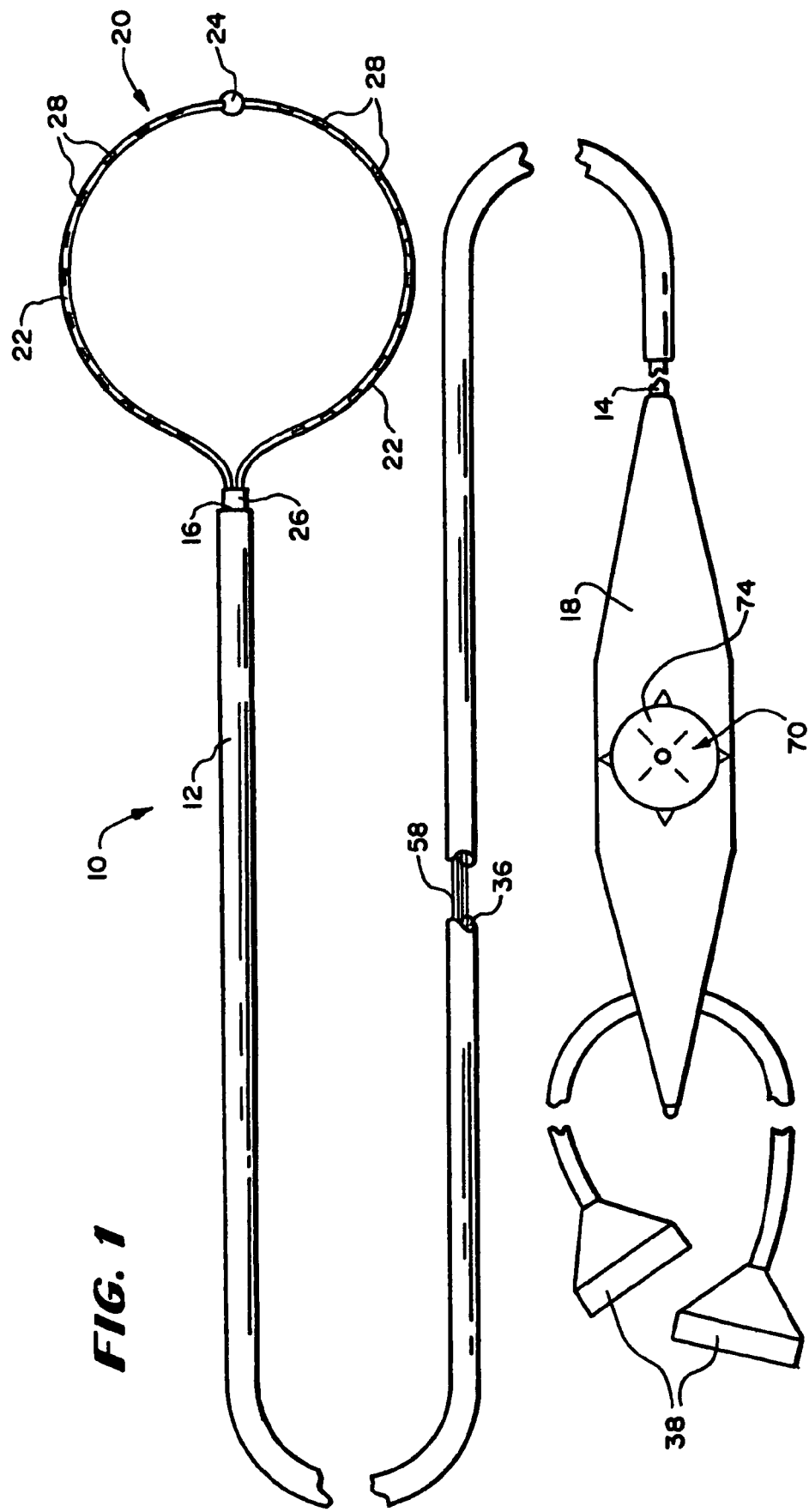
FIG. 1 is a plan view of an ablation probe having a full-loop structure for supporting multiple ablation elements.

FIG. 1 shows a multiple electrode probe 10 that includes a loop structure 20 carrying multiple electrode elements 28. Instead of, or in addition to the electrode elements, the loop structure can carry one or more of the other operative elements discussed in Section III below.

The probe 10 includes a flexible catheter tube 12 with a proximal end 14 and a distal end 16. The proximal end 14 carries an attached handle 18. The distal end 16 carries a loop structure 20 that supports multiple electrodes.

In FIG. 1, the loop support structure 20 comprises two flexible spline legs 22 spaced diametrically opposite each other. The dual leg loop structure 20 shown in FIG. 1 will be called a "full-loop" structure.

The far ends of the spline legs 22 radiate from a distal hub 24. The near ends of the spline legs 22 radiate from a base 26 attached to the distal end 16 of the catheter tube 12. The multiple electrode elements 28 are arranged along each spline leg 22.

Figure 2:
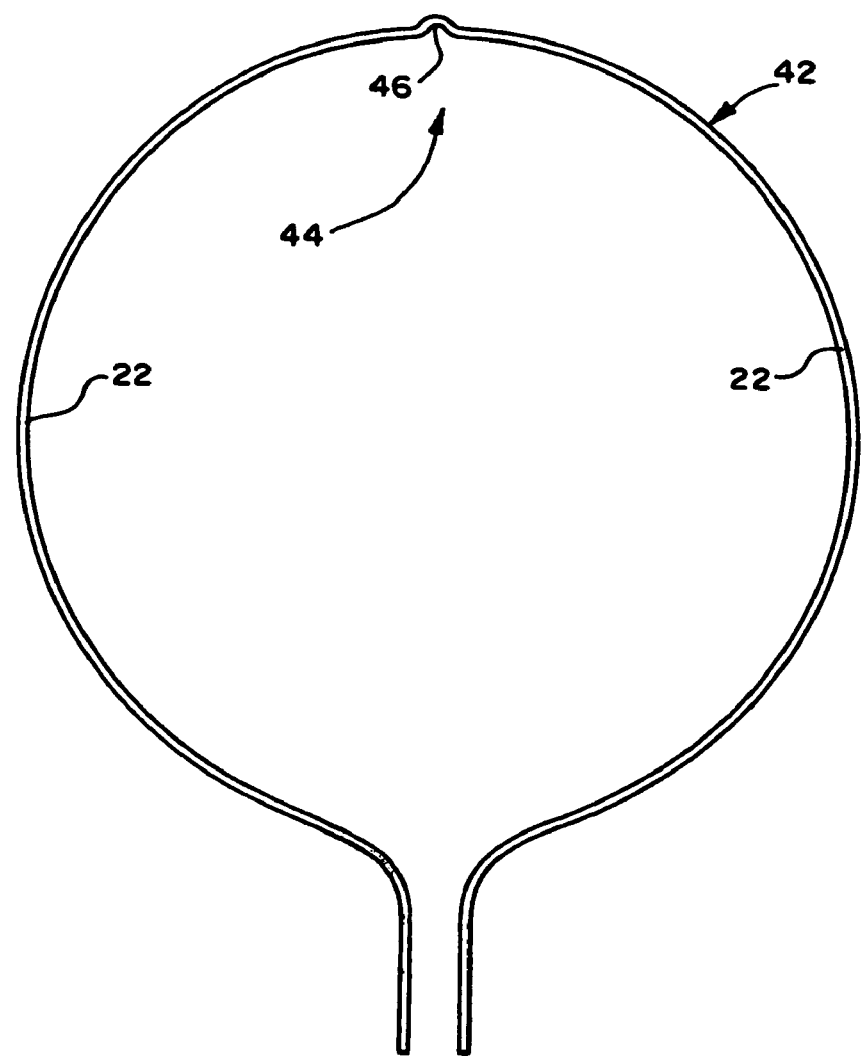
FIG. 2 is an elevation view of a spline used to form the loop structure shown in FIG. 1.

In one implementation, the two spline legs 22 of the structure 20 are paired together in an integral loop body 42 (see FIG. 2). Each body 42 includes a mid-section 44 from which the spline elements 22 extend as an opposed pair of legs. As FIG. 2 shows, the mid-section 44 includes a preformed notch or detent 46, whose function will be described later.

The loop body 42 is preferably made from resilient, inert wire, like Nickel Titanium (commercially available as Nitinol material). However, resilient injection molded inert plastic or stainless steel can also be used. Preferably, the spline legs 22 comprise thin, rectilinear strips of resilient metal or plastic material. Still, other cross sectional configurations can be used.

In this implementation (see FIGS. 3 and 4), the distal hub 24 has a generally cylindrical side wall 50 and a rounded end wall 52. A longitudinal slot 56 extends through the hub 24, diametrically across the center bore 54.

In the illustrated embodiment, the hub 24 is made of an inert, machined metal, like stainless steel. The bore 54 and slot 56 can be formed by conventional EDM techniques. Still, inert molded plastic materials can be used to form the hub 24 and associated openings.

In this implementation, to assemble the structure 20 (see FIGS. 4 and 5), a spline leg 22 of the hoop-like body 42 is inserted through the slot 56 until the mid-body section 44 enters the bore 54. The detent 46 snaps into the bore 54 (see FIG. 4) to lock the body 42 to the hub 24, with the opposed pair of spline legs 22 on the body 42 radiating free of the slot 56 (see FIG. 5).

Figure 5:
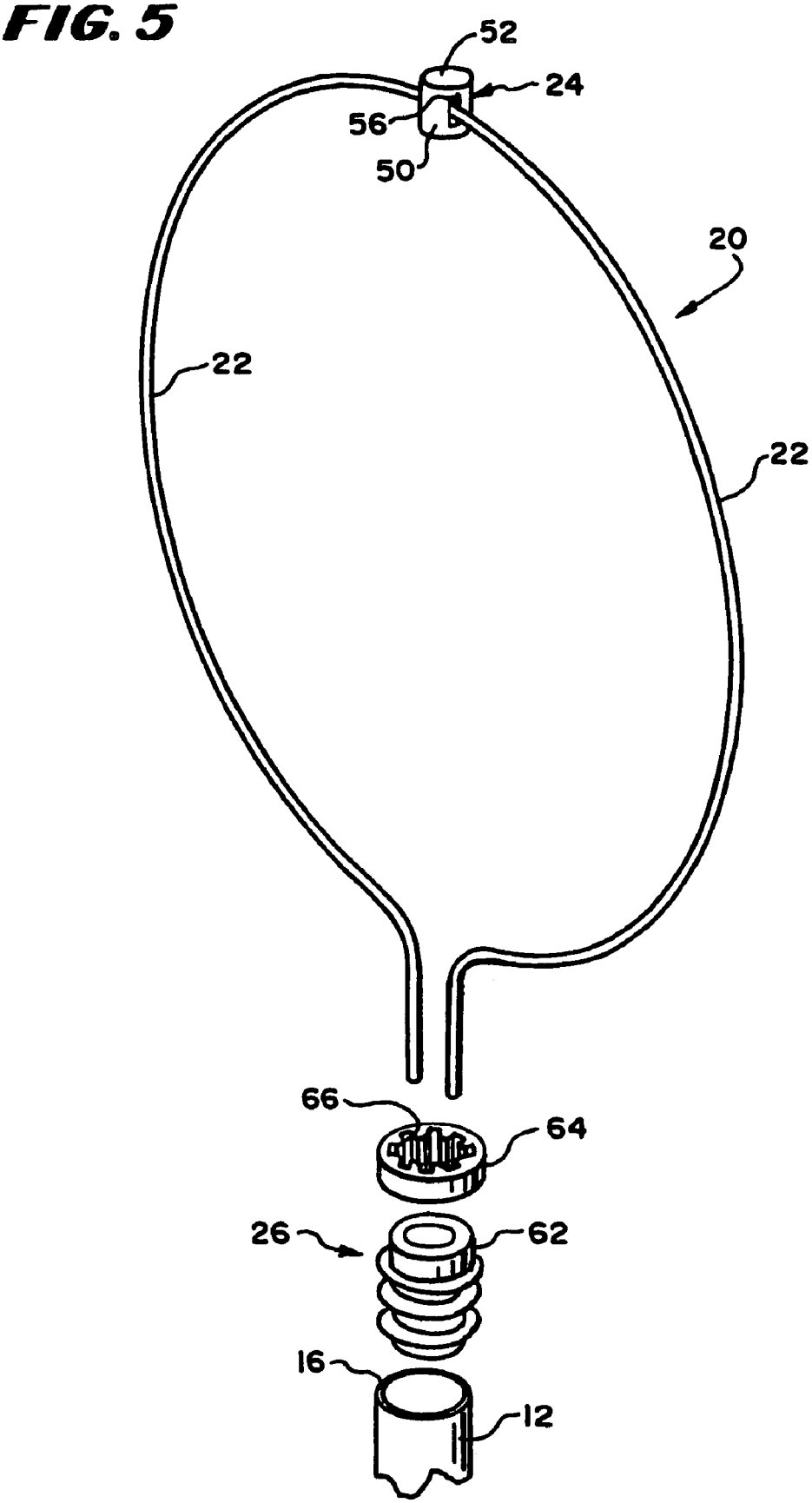
FIG. 5 is a perspective, partially exploded view of the spline, distal hub, and base assembly used to form the loop structure shown in FIG. 1.
Figure 6A:
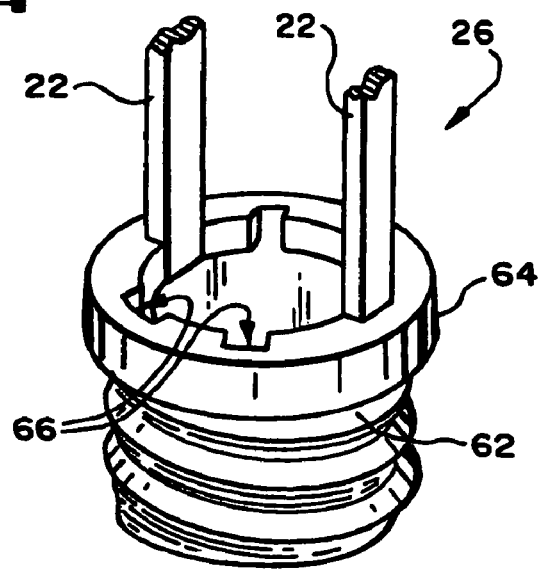
FIG. 6a is an enlarged perspective view of the base assembly shown in FIG. 5.
Figure 6B:
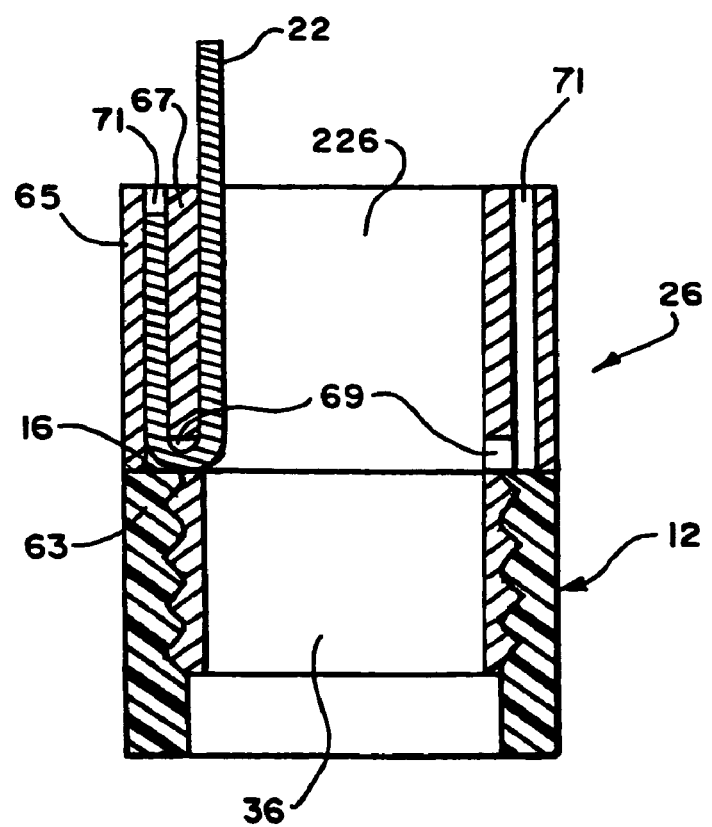
FIG. 6b is a side section view of an alternative base assembly for the loop structure shown in FIG. 1.

In the illustrated embodiment (see FIGS. 5 and 6a), the base 26 includes an anchor member 62 and a mating lock ring 64. The anchor member 62 fits with an interference friction fit into the distal end 16 of the catheter tube 12. The lock ring 64 includes a series of circumferentially spaced grooves 66 into which the free ends of the spline legs 22 fit. The lock ring 64 fits about the anchor member 62 to capture with an interference fit the free ends of the spline legs 22 between the interior surface of the grooves 66 and the outer surface of the anchor member 62 (see FIG. 6). The anchor member 62/lock ring 64 assembly holds the spline elements 22 in a desired flexed condition.

In an alternative construction (see FIG. 6b), the base 26 can comprise a slotted anchor 63 carried by the distal end 16 of the catheter tube 12. The slotted anchor 63 is made of an inert machined metal or molded plastic material. The slotted anchor 63 includes an outer ring 65 and a concentric slotted inner wall 67. The interior of the anchor 63 defines an open lumen 226 to accommodate passage of wires and the like between the catheter tube bore 36 and the support structure 20 (as will be described in greater detail later).

The inner wall 67 includes horizontal and vertical slots 69 and 71 for receiving the free ends of the spline legs 22. The free ends pass through the horizontal slots 69 and are doubled back upon themselves and wedged within the vertical slots 71 between the outer ring 65 and the inner wall 67, thereby securing the spline legs 22 to the anchor 63.

There are other alternative ways of securing the spline legs 22 to the distal end 16 of the catheter tube 12, which will be described later.

Figure 3:
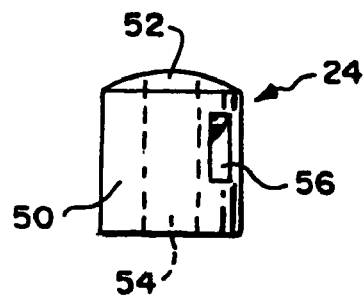
FIG. 3 is an elevation view of the distal hub used to form the loop structure shown in FIG. 1.

Preferably, the full-loop structure 20 shown in FIG. 1 does not include a hub 24 like that shown in FIGS. 1 and 3, and, in addition, does not incorporate a detented integral loop body 42 like that shown in FIG. 2. Any single full-loop structure without a center stiffener or stylet (as will be described later) preferably comprises a single length of resilient inert wire (like Nickel Titanium) bent back upon itself and preformed with resilient memory to form the desired full loop shape. Structure 112 in FIG. 29 (which will be described in greater detail later) exemplifies the use of a preshaped doubled-back wire to form a loop, without the use of a hub 24 or detented loop body 42.

FIG. 7 shows an alternative loop structure 20(1) that includes a single spline leg 22(1) carrying multiple electrode elements 28. This single leg loop structure will be called a "half-loop" structure, in contrast to the dual leg loop structure 20 (i.e., the "full-loop" structure) shown in FIG. 1.

In assembling the half-loop structure 20(1) shown in FIG. 7, the hoop-like body 42 shown in FIG. 2 is cut on one side of the detent 46 to form the single spline leg 22(1). The single spline leg 22(1) is snap-fitted into the hub 24 and captured with an interference fit by the anchor member 62/lock ring 64 assembly of the base 26 in the manner just described (shown in FIGS. 5 and 6a). Alternatively, the single spline leg 22(1) can be wedged within the base anchor ring 63 shown in FIG. 6b. In FIG. 7, the half-loop structure 20(1) also includes a center stiffener 40 passing through the base 26 and to the bore 54 of the hub 24. The stiffener 40 can be made of a flexible plastic like PEEK, or from a hollow tube like hypo-tubing or braid plastic tubing.

It should be appreciated that other loop-type configurations besides the full-loop structure 20 and half-loop structure 20(1) are possible. For example, two half-loop structures 20(1), one or both carrying electrode elements 28, can be situated in circumferentially spaced apart positions with a center stiffener 40, as FIG. 8 shows. As another example, four half-loop structures, or two full-loop structures can be assembled to form a three-dimensional, basket-like structure 60 (without using a center stiffener 40), like that shown in FIG. 9.

Regardless of the configuration, the loop structure provides the resilient support necessary to establish and maintain contact between the electrode elements 28 and tissue within the body.

The electrode elements 28 can serve different purposes. For example, the electrode elements 28 can be used to sense electrical events in heart tissue. In the illustrated and preferred embodiments, the principal use of the electrode elements 28 is to emit electrical energy to ablate tissue. In the preferred embodiments, the electrode elements 28 are conditioned to emit electromagnetic radio frequency energy.

As described in greater detail in Section III below, the electrode elements 28 can be assembled in various ways.

In one preferred embodiment (see FIG. 10), the elements comprise multiple, generally rigid ring electrode elements 30 arranged in a spaced apart, segmented relationship upon a flexible, electrically nonconductive sleeve 32 which surrounds the underlying spline leg 22. The sleeve 32 is made a polymeric, electrically nonconductive material, like polyethylene or polyurethane. The electrode rings 30 are pressure fitted about the sleeve 32. The flexible portions of the sleeve 32 between the rings 30 comprise electrically nonconductive regions. Alternatively, the electrode segments 30 can comprise a conductive material coated upon the sleeve 32. The electrode coating can be applied either as discrete, closely spaced segments or in a single elongated section.

In a more preferred embodiment (see FIGS. 11a and 11b), spaced apart lengths of closely wound, spiral coils are wrapped about the sleeve 32 to form an array of segmented, generally flexible electrodes 34. The inherent flexible nature of a coiled electrode structures 34 also makes possible the construction of a continuous flexible ablating element comprising an elongated, closely wound, spiral coil wrapped about all or a substantial length of the flexible sleeve 32.

The electrode elements 28 can be present on all spline legs 22, as FIG. 1 shows, or merely on a selected number of the spline legs 22, with the remaining spline legs serving to add structural strength and integrity to the structure.

Various access techniques can be used to introduce the probe 10 and its loop support structure 20 into the desired region of the heart. For example, to enter the right atrium, the physician can direct the probe 10 through a conventional vascular introducer through the femoral vein. For entry into the left atrium, the physician can direct the probe 10 through a conventional vascular introducer retrograde through the aortic and mitral valves.

Alternatively, the physician can use the delivery system shown in U.S. Pat. No. 5,636,634 entitled "Systems and Methods Using Guide Sheaths for Introducing, Deploying, and Stabilizing Cardiac Mapping and Ablation Probes."

In the illustrated and preferred embodiments (see FIGS. 10 and 11*a/b*), each flexible ablation element carries at least one and, preferably, at least two, temperature sensing elements 68. The multiple temperature sensing elements 68 measure temperatures along the length of the electrode element 28. The temperature sensing elements 68, which can comprise thermistors or thermocouples, can be located on the ablation elements in the manner shown in FIGS. 10 and 11*a/b*. Preferably, the temperature sensing elements 68 can be located on one or both of the longitudinal end edges of the ablation elements, as shown in U.S. patent application Ser. No. 08/788,782, entitled '"Systems and Methods for Controlling Ablation Using Multiple Temperature Sensing Elements," which is incorporated herein by reference.

An external temperature processing element, such as that discussed below in Section IX, receives and analyses the signals from the multiple temperature sensing elements 68 in prescribed ways to govern the application of ablating energy to the flexible ablation element. The ablating energy is applied to maintain generally uniform temperature conditions along the length of the element. Additionally, further details of the use of multiple temperature sensing elements in tissue ablation can be found in co-pending U.S. application Ser. No. 08/638,989, filed Apr. 24, 1996, which is File Wrapper Continuation of U.S. application Ser. No. 08/286,930, filed Aug. 8, 1994, entitled "Systems and Methods for Controlling Tissue Ablation Using Multiple Temperature Sensing Elements."

To aid in locating the structure 20 within the body, the handle 16 and catheter body 12 preferably carry a steering mechanism 70 (see FIGS. 1 and 12) for selectively bending or flexing the distal end 16 of the catheter body 12.

Figure 12:
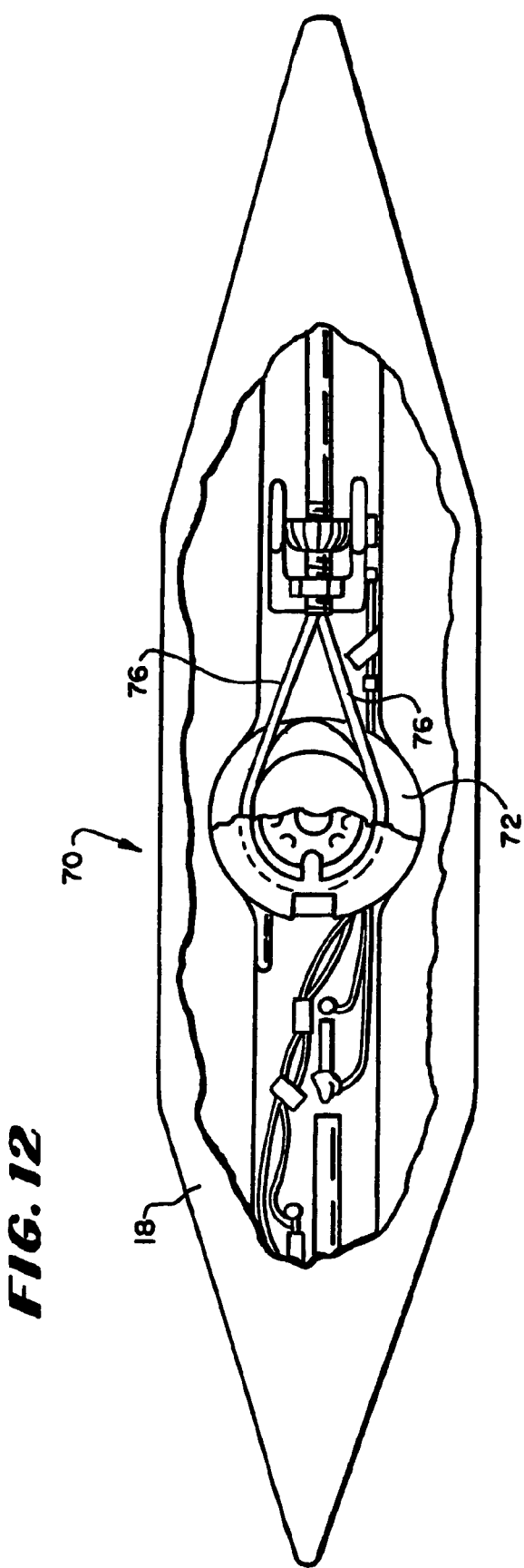
FIG. 12 is a top view of a steering mechanism used to deflect the distal end of the probe shown in FIG. 1.

The steering mechanism 18 can vary. In the illustrated embodiment (see FIG. 12), the steering mechanism 70 includes a rotating cam wheel 72 with an external steering lever 74 (see FIG. 1). As FIG. 12 shows, the cam wheel 72 holds the proximal ends of right and left steering wires 76. The steering wires 76, like the signal wires 58, pass through the catheter body lumen 36. The steering wires 76 connect to the left and right sides of a resilient bendable wire or spring (not shown) enclosed within the distal end 16 of the catheter body 12. Forward movement of the steering lever 74 flexes or curves the distal end 16 down. Rearward movement of the steering lever 74 flexes or curves the distal end 16 up.

Further details of this and other types of steering mechanisms are shown in Lundquist and Thompson U.S. Pat. No. 5,254,088, which is incorporated into this Specification by reference.

B. Variable Shape Loop Support Structures

To uniformly create long, thin lesions having the desired therapeutic effect, the loop support structure 20 or 20(1) must make and maintain intimate contact between the electrode elements 28 and the endocardium. This invention provides loop support structures that the physician can adjust to adapt to differing physiologic environments.

1. Distended Loop Structures

The adjustable loop structure 78 shown in FIG. 13 is in many respects similar to the full-loop structure 20 shown in FIG. 1. The adjustable full-loop structure 78 includes the pair of diametrically opposite spline legs 22 that radiate from the base 26 and hub 24.

In addition, the adjustable full-loop structure 78 includes a flexible stylet 80 attached at its distal end to the hub bore 54. The stylet 80 can be made from a flexible plastic material, like PEEK, or from a hollow tube, like hypo-tubing or braid plastic tubing.

The stylet 80 extends along the axis of the structure 78, through the base 26 and catheter body lumen 36, and into the handle 18. In this arrangement, the stylet 80 is free to slide fore and aft along the axis of the catheter body 12.

The proximal end of the stylet 80 attaches to a control knob 82 in the handle 18 (as FIG. 13 shows). The control knob 82 moves within a groove 84 (see FIGS. 13 and 14) in the handle 18 to impart fore and aft movement to the stylet 80. Stylet movement changes the flexure of the structure 78.

Forward movement of the stylet 80 (i.e., toward the distal end 16) pushes the hub 24 away from the base 26 (see FIG. 15). The loop structure 78 elongates as the spline legs 22 straighten and move radially inward, to the extent permitted by the resilience of the spline legs 22. With the spline legs 22 straightened, the loop structure 78 presents a relatively compact profile to facilitate vascular introduction.

Rearward movement of the stylet 80 (i.e., toward the distal end 16) pulls the hub 24 toward the base 26 (see FIG. 16). The spline legs 22 bend inward in the vicinity of the hub 24, while the remainder of the splines, constrained by the base, distend. The loop structure 78 bows radially out to assume what can be called a "heart" shape.

When the structure 78 is positioned within the atrium 88 of a heart in the condition shown in FIG. 16, the stylet 80 compresses the spline legs 22, making them expand or bow radially. The expansion presses the distended midportion of the spline legs 22 (and the electrode elements 28 they carry) symmetrically against opposite walls 86 of the atrium 88. The symmetric expansion of the outwardly bowed spline legs 22 presses the opposite atrial walls 86 apart (as FIG. 16 shows), as the radial dimension of the loop structure 78 expands to span the atrium 88.

The symmetric expansion presses the electrode elements 28 into intimate surface contact against the endocardium. The symmetric expansion stabilizes the position of the loop structure 78 within the atrium 88. The resilience of the spline legs 22, further compressed by the pulled-back stylet 80, maintains intimate contact between the electrode elements 28 and atrial tissue, without trauma, as the heart expands and contracts.

Figure 19:
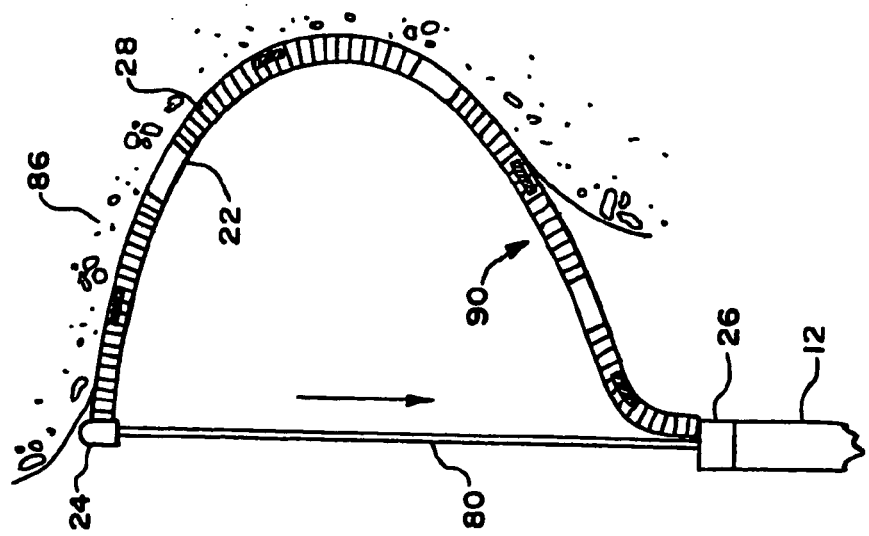
FIG. 19 is a plan view of a half-loop structure shown in FIG. 17, with the control handle moves to distend the half-loop structure.
Figure 18:
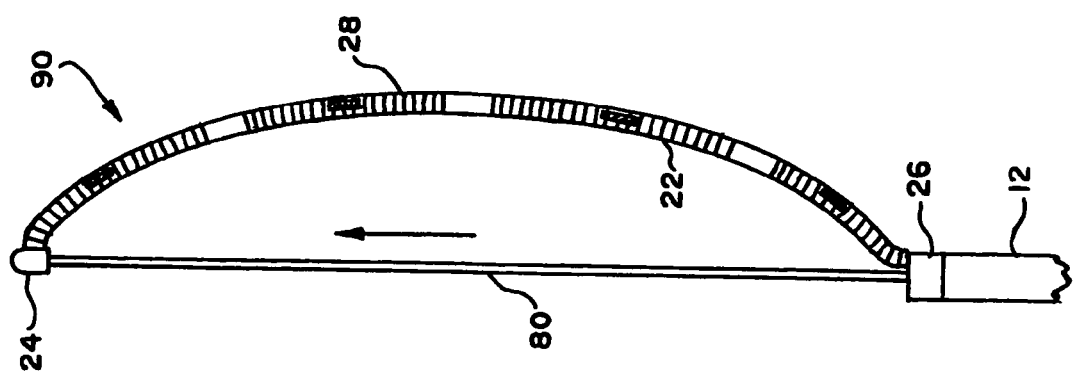
FIG. 18 is a plan view of the half-loop structure shown in FIG. 17, with the control knob moved to extend the half-loop structure.
Figure 17:
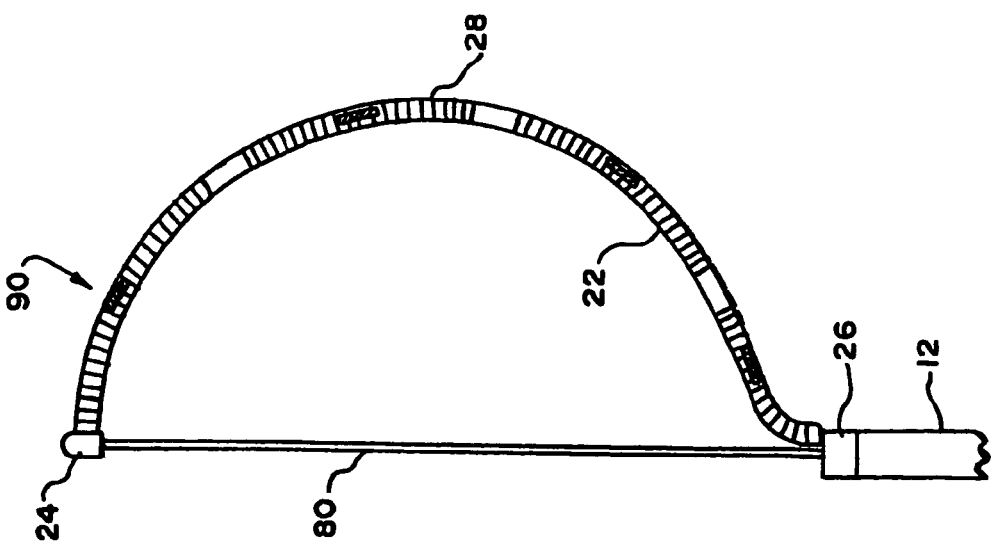
FIG. 17 is a plan view of a half-loop structure for supporting multiple electrode elements having an associated center stylet attached to a remote control knob for movement to extend and distend the half-loop structure.

As FIGS. 17 to 19 show, the push-pull stylet 80 can also be used in association with a half-loop structure 90, like that previously shown and discussed in FIG. 7.

In this arrangement, pushing the stylet 80 forward (as FIG. 18 shows) elongates the half-loop structure 90 for vascular introduction. Pulling the stylet 80 rearward (as FIG. 19 shows) bows the single spline leg 22 of the structure outward, expanding it so that more secure contact can be achieved against the atrial wall 86, or wherever tissue contact is desired.

2. Curvilinear Loop Structures

Figure 21:
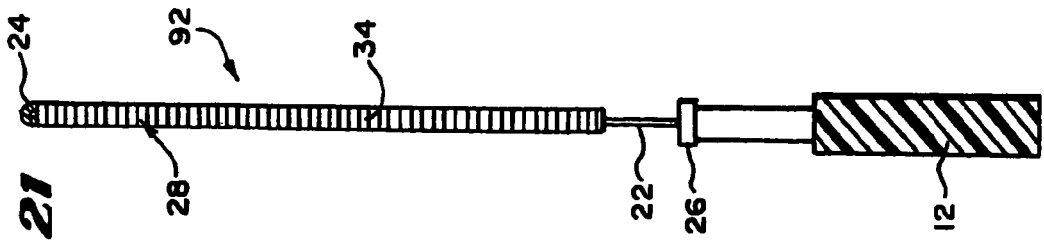
FIG. 21 is a side elevation view of the full-loop structure shown in FIG. 20.
Figure 20:
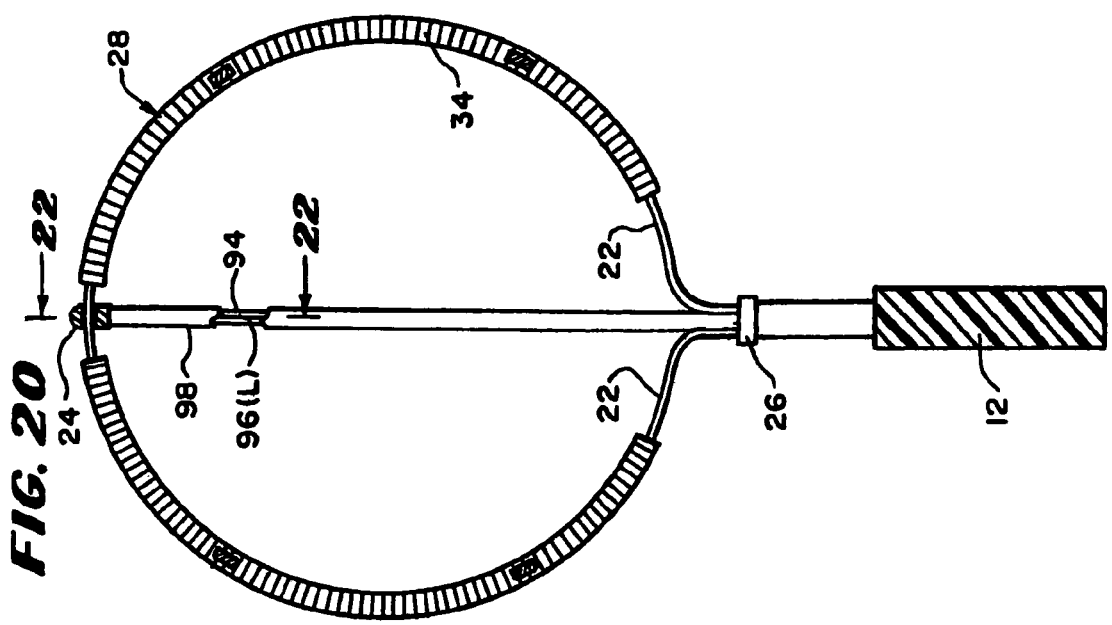
FIG. 20 is a plan view of a full-loop structure for supporting multiple electrode elements having an associated center stylet attached to a remote control knob for movement to extend and distend the full-loop structure, and also having a remotely controlled steering mechanism to flex the center stylet to bend the full-loop structure into a curvilinear shape.

FIGS. 20 and 21 show a full-loop structure 92 that includes a center stylet 94, which can be flexed. The flexing of the center stylet 94 bends the spline legs 22 in a second direction different than the radial direction in which they are normally flexed. In the illustrated embodiment, this second direction is generally perpendicular to the axes of the spline legs 22, as FIGS. 23*a/b* and 24 show, although acute bends that are not generally perpendicular can also be made. The bending of the spline legs 22 in this fashion makes possible the formation of long, thin curvilinear lesions using a full-loop structure 92, or (as will be described later) in a half-loop structure 110, as well.

The stylet 94 itself can be either fixed in position between the hub 24 and the base 26, or movable along the axis of the loop structure 92 to extend and distend the radial dimensions of the spline legs 22 in the manner already described (see FIGS. 15 and 16). In the illustrated and preferred embodiment, the stylet 94 slides to alter the radial dimensions of the structure.

Figure 22:
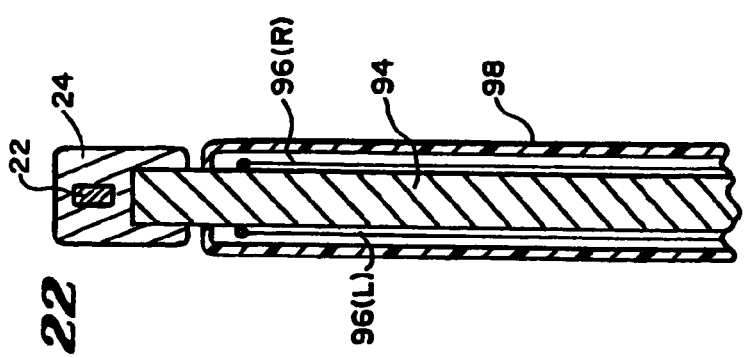
FIG. 22 is an enlarged sectional view, generally taken along line 22—22 in FIG. 20, showing the steering wires attached to the center stylet to flex it.

In one implementation, as FIG. 22 best shows, the stylet 94 is made from a metal material, for example stainless steel 17-7, Elgiloy™ material, or Nickel Titanium material. A pair of left and right steering wires, respectively 96(R) and 96(L) is attached to opposite side surfaces of the stylet 94 near the hub 24, by adhesive, soldering, or by suitable mechanical means. The steering wires 96(R) and 96(L) are attached to the stylet side surfaces in a diametric opposite orientation that is at right angles to the radial orientation of the spline legs 22 relative to the stylet 94.

The steering wires 96(R) and 96(L) extend along the stylet 94, through the base 26 and catheter body lumen 36, and into the handle 18 (see FIG. 25). Preferably, as FIG. 22 best shows, a tube 98 surrounds the stylet 94 and steering wires 96(R) and 96(L), at least along the distal, exposed part of the stylet 94 within the structure 92, keeping them in a close relationship. The tube 98 can be heat shrunk to fit closely about the stylet 94 and steering wires 96(R) and 96(L).

As FIGS. 25 and 26 show, a groove 100 in the handle carries a control assembly 102. The stylet 94 is attached to the control assembly 102, in the manner already described with respect to the control knob 82 in FIGS. 13 and 14. Sliding movement of the control assembly 102 within the groove 100 imparts fore and aft movement to the stylet 94, thereby distending or extending the loop structure 92.

The control assembly 102 further includes a cam wheel 104 (see FIG. 26) rotatable about an axle on the control assembly 102 in response to force applied to an external steering lever 108. The cam wheel 104 holds the proximal ends of the steering wires 96(R) and 96(L), in the manner disclosed in Lundquist and Thompson U.S. Pat. No. 5,254, 088, already discussed, which is incorporated herein by reference.

Twisting the steering lever 108 counterclockwise applies tension to the left steering wire 96(L), bending the loop structure 92 to the left (as FIG. 23*a* shows). The electrode elements 28 (which in FIGS. 20 to 27 comprises a continuous coil electrode 34, described earlier) likewise bend to the left.

Similarly, twisting the steering lever 108 clockwise applies tension to the right steering wire 96(R), bending the loop structure 92 to the right (as FIGS. 23*b* and 24 show). The electrode elements 28 likewise bend to the right.

The bent electrode elements 28, conforming to the bent spline legs 22, assume different curvilinear shapes, depending upon amount of tension applied by the steering wires 96(R) and 96(L). When contacting tissue, the bent electrode elements 28 form long, thin lesions in curvilinear patterns.

In an alternative implementation, the stylet 94 is instead made of a malleable metal material, like annealed stainless steel. In this arrangement, before deployment in the body, the physician applies external pressure to manually bend the stylet 94 into a desired shape, thereby imparting a desired curvilinear shape to the electrode elements of the associated loop structure. The malleable material of the stylet 94 retains the preformed shape, until the associated loop structure is withdrawn from the body and sufficient external pressure is again applied by the physician to alter the stylet shape.

In addition to having a malleable stylet 94, the splines 22 themselves can also be made of a malleable material, like annealed stainless steel, or untreated stainless steel 17-7, or untreated Nickel Titanium. In one implementation, the most distal parts of the malleable splines 22 are heat treated to maintain their shape and not collapse during introduction and deployment in the vascular system. This will also give the overall structure greater stiffness for better contact with the tissue. It also gives the physician the opportunity to bend the structure to form long, thin, lesions in prescribed curvilinear patterns set by the malleable splines.

Whether flexible and remotely flexed during deployment, or malleable and manually flexed before deployment, by further adjusting the fore-and-aft position of the stylet 94, the physician can also control the radial dimensions of the loop structure 94 in concert with controlling the curvilinear shape of the loop structure 92, as FIG. 27 shows. A diverse array of radial sizes and curvilinear shapes is thereby available.

As FIG. 28 shows, a half-loop structure 110 can also include a fixed or movable stylet 94 with steering wires 96(R) and 96(L). The use of the same handle-mounted control assembly 102/rotatable cam 104 assembly shown in FIGS. 25 and 26 in association with the half-loop structure 110 makes possible the creation of diverse curvilinear shapes of variable radii. Alternatively, a malleable stylet 94 and malleable splines can be used.

3. Loop Structures with Movable Spline Legs

FIGS. 29 to 35 show a full-loop structure 112 in which only one spline leg 114 is attached to the base 26. The fixed spline leg 114 is preformed with resilient memory to assume a curve of a selected maximum radius (shown in FIG. 33). The other spline leg 116, located diametrically opposed to the fixed spline leg 114, extends through the base 26 and catheter body lumen 36 (see FIGS. 30*a* and 30*b*) into the handle 18. The spline leg 116 slides fore and aft with respect to the base 26. Movement of the spline leg 116 changes the flexure of the structure 112.

The full-loop structure 112 shown in FIGS. 29 to 35 need not include a hub 24 like that shown in FIGS. 1 and 3 and, in addition, need not incorporate a detented integral loop body 42 like that shown in FIG. 2. Any single full-loop structure without a center stiffener or stylet, like the structure 112 in FIG. 29, can comprise a single length of wire bent back upon itself and preformed with resilient memory to form the desired full loop shape. For the same reason, the single full-loop structure 20 shown in FIG. 1 can, in an alternative construction, be made without a hub 24 and a detented loop body 42, and instead employ a preshaped doubled-back wire to form a loop, like the structure 20.

FIG. 30*b* shows an alternative way of securing the fixed spline leg 114 to the distal end 16 of the catheter tube 12, without using a base 26. In this embodiment, the free end of the fixed spline leg 114 lies against the interior of the tube 12. The leg 114 passes through a slit 115 formed in the catheter tube 12. The leg 114 is bent back upon itself in a u-shape to lie against the exterior of the tube 12, wedging the tube 12 within the u-shape bend 117. A sleeve 119 is heat shrunk about the exterior of the tube 12 over the region where the u-shape bend 117 of the spline leg 114 lies, securing it to the tube 12. Alternatively, a metallic ring (not shown) can be used to secure the spline leg 114 to the tube 12. The movable spline leg 116 and wires 58 pass through the interior bore 36 of the catheter tube 12, as before described.

The proximal end of the spline leg 116 (see FIG. 29) is attached to a movable control knob 82 carried in a groove 84 on the handle 18, like that shown in FIG. 13. Movement of the control knob 82 within the groove 84 thereby imparts fore-and-aft movement to the spline leg 116.

In the illustrated embodiment, the fixed spline leg 114 carries electrode elements 28 in the manner already described. The movable spline leg 116 is free of electrode elements 28. Still, it should be appreciated that the movable spline leg 116 could carry one or more electrode elements 28, too.

As FIGS. 31 to 33 show, moving the control knob 82 forward slides the movable spline leg 116 outward, and vice versa. The movable spline leg 116 applies a counter force against the resilient memory of the fixed spline leg 114, changing the flexure and shape of the loop structure 112 for vascular introduction and deployment in contact with tissue. By pulling the movable spline leg 116 inward (as FIG. 31 shows), the counter force contracts the radius of curvature of the fixed spline leg 114 against its resilient memory. Pushing the movable spline leg 116 outward (as FIGS. 32 and 33 show) allows the resilient memory of the fixed spline leg 114 to expand the radius of curvature until the selected maximum radius is achieved. The counter force applied changes the flexure and shapes the fixed spline leg 114 and the electrode elements 28 it carries to establish and maintain more secure, intimate contact against atrial tissue.

The magnitude (designated V in FIGS. 31 to 33) of the counter force, and the resulting flexure and shape of the loop structure 112, varies according to extent of outward extension of the movable spline leg 116. Pulling the movable spline leg 116 progressively inward (thereby shortening its exposed length) (as FIG. 31 shows) contracts the loop structure 112, lessening its diameter and directing the counter force progressively toward the distal end of the structure. Pushing the movable spline leg 116 progressively outward (thereby lengthening its exposed length) (as FIGS. 32 and 33 show) progressively expands the loop structure 112 in response to the resilient memory of the fixed spline leg 114, increasing its diameter and directing the counter force progressively away from the distal end of the structure.

As FIGS. 34 and 35 show, by manipulating the movable spline leg 116, the physician can adjust the flexure and shape of the loop structure 112 within the atrium 88 from one that fails to make sufficient surface contact between the electrode element 28 and the atrial wall 86 (as FIG. 34 shows) to one that creates an extended region of surface contact with the atrial wall 86 (as FIG. 35 shows).

FIGS. 36 to 38 show a full-loop structure 118 in which each spline leg 120 and 122 is independently movable fore and aft with respect to the base 26. In the illustrated embodiment, both spline legs 120 and 122 carry electrode elements 28 in the manner already described.

In this arrangement, the handle 18 includes two independently operable, sliding control knobs 124 and 126 (shown diagrammatically in FIGS. 36 to 38), each one attached to a movable spline leg 120/122, to impart independent movement to the spline legs 120/122 (as shown by arrows in FIGS. 36 to 38). Each spline leg 120/122 is preformed with resilient memory to achieve a desired radius of curvature, thereby imparting a resilient curvature or shape to the full-loop structure 118 itself. Coordinated opposed movement of both spline legs 120/122 (as FIGS. 37 and 38 show) using the control knobs 124/126 allows the physician to elongate the curvature of the loop structure 118 into more of an oval shape, compared to more circular loop structures 112 formed using a single movable leg 116, as FIGS. 31 to 33 show.

FIGS. 39a and 39b show an alternative full-loop structure 128 having one spline leg 130 that is fixed to the base 26 and another spline leg 132, located diametrically opposed to the fixed spline 130, that is movable fore and aft with respect to the base 26 in the manner already described. The movable spline leg 132 can carry electrode elements 28 (as FIG. 39a shows), or be free of electrode elements, depending upon the preference of the physician.

In the structure shown in FIGS. 39a and 39b, the fixed spline leg 130 branches in its midportion to form a smaller, secondary full-loop structure 134 that carries electrode elements 28. In the embodiment shown in FIGS. 39a and 39b, the secondary loop structure 134 lies in a plane that is generally perpendicular to the plane of the main full-loop structure 128.

The smaller, secondary full-loop structure 134 makes possible the formation of annular or circumferential lesion patterns encircling, for example, accessory pathways, atrial appendages, and the pulmonary vein within the heart. In the illustrated embodiment, the movable spline leg 132 compresses the secondary full-loop structure 134, urging and maintaining it in intimate contact with the targeted tissue area.

FIGS. 39a and 39b therefore show a compound flexible support for electrode elements. While the primary support structure 128 and the secondary support structure 134 are shown as full loops, it should be appreciated that other arcuate or non-arcuate shapes can be incorporated into a compound structure. The compound primary structure 128 integrated with a secondary structure 134 need not include a movable spline leg, or, if desired, both spline legs can be movable. Furthermore, a center stylet to contract and distend the main structure 128 can also be incorporated, with or without a stylet steering mechanism.

Figure 40A:
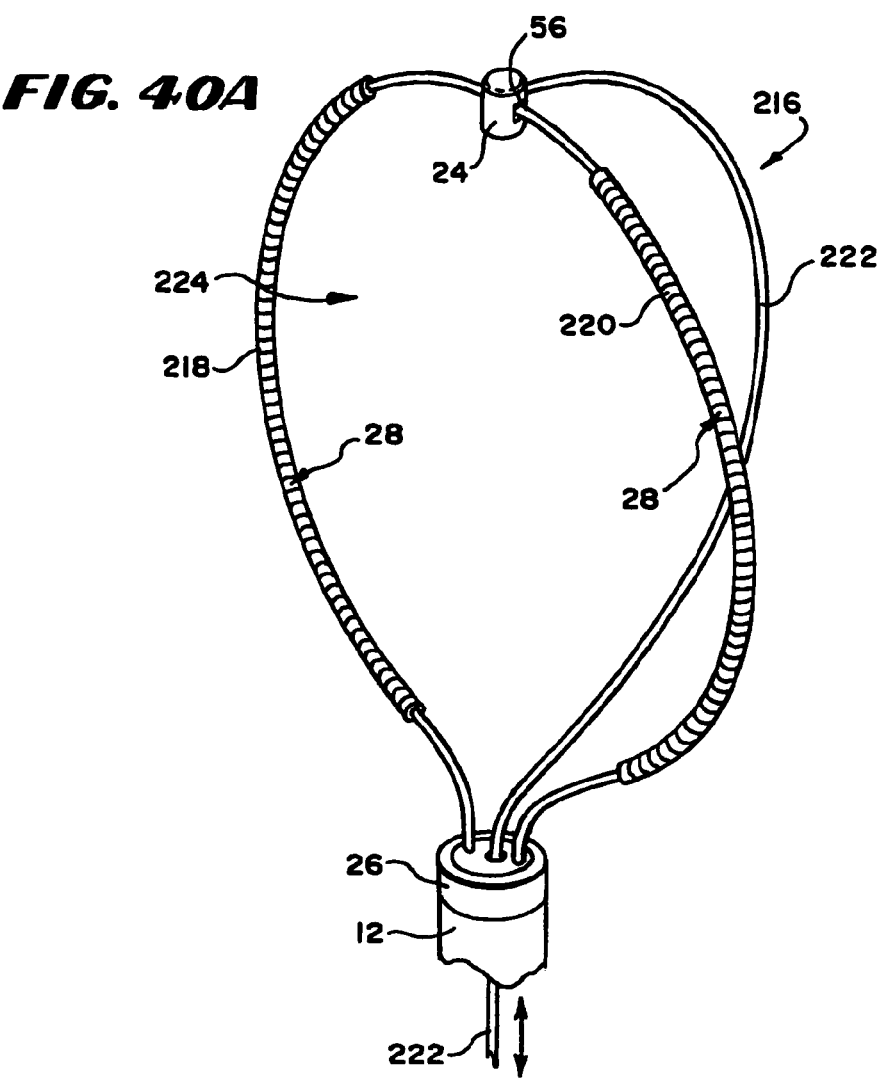
FIG. 40a is a perspective view of a modified full-loop structure for supporting multiple electrode elements having an odd number of three or more spline legs.
Figure 40B:
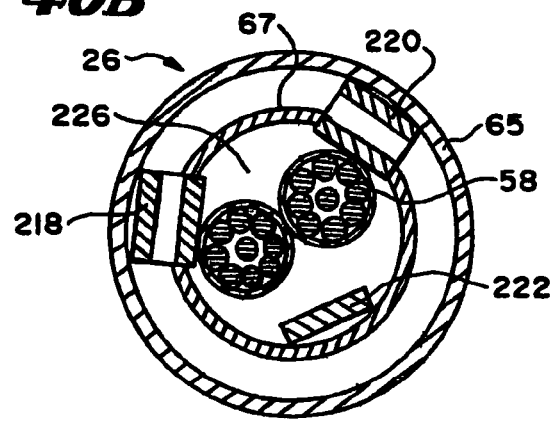

FIGS. 40a and 40b show a modified full-loop structure 216 having an odd number of spline legs 218, 220, and 222. The structure 216 includes two spline legs 218 and 220 that, in the illustrated embodiment, are fixed to the base 26 about 120° apart from each other. As FIG. 40b shows, the base 26 is generally like that shown in FIG. 6b, with the slotted anchor 63 in which the near ends of the legs 218 and 220 are doubled back and wedged. The structure 216 also includes a third spline leg 222 that, in the illustrated embodiment, is spaced about 120° from the fixed spline legs 218/220. As FIG. 40b shows, the near end of the third spline leg 222 is not attached to the base 26, but passes through the inner lumen 226 into the lumen 36 of the catheter tube 12. The third spline leg 222 is thereby movable fore and aft with respect to the base 26 in the manner already described. Alternatively, all spline legs 218, 220, and 222 can be fixed to the base 26, or more than one spline leg can be made moveable.

Figure 4:
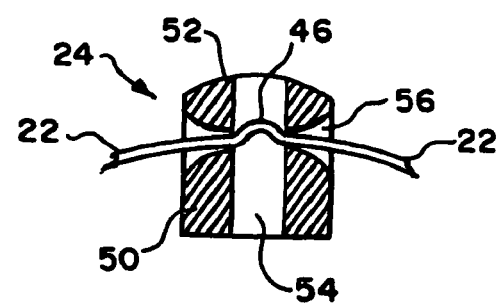
FIG. 4 is a side section view of the hub shown in FIG. 3.

A hub 24 like that shown in FIGS. 3 and 4 includes circumferentially spaced slots 56 to accommodate the attachment of the three splines 218, 220, and 222.

The fixed splines 218 and 220 carry electrode elements 28 (as FIG. 40*a* shows), while the movable spline 22 is free of electrode elements. As FIG. 40*b* show, the wires 58 coupled to the electrode elements 28 pass through the anchor lumen 226 for transit through the catheter tube bore 36. The orientation of the fixed splines 218 and 220 relative to the movable spline 222 thereby presents an ablation loop 224, like the secondary loop structure 134 shown in FIGS. 39*a/b*, that lies in a plane that is generally transverse of the plane of the movable spline 222. Of course, other orientations of an odd number of three or more spline legs can be used.

The movable spline leg 222 extends and compresses the secondary structure 134 to urge and maintain it in intimate contact with the targeted tissue area. Of course, a center stylet to further contract and distend the ablation loop 224 can also be incorporated, with or without a stylet steering mechanism.

4. Bifurcated Loop Structures

FIGS. 41, 42, and 43 show a variation of a loop structure, which will be called a bifurcated full-loop structure 136. The structure 136 (see FIG. 41) includes two oppositely spaced splines legs 138 and 140, each carrying one or more electrode elements 28. The near end of each spline leg 138/140 is attached to the base 26. The far end of each spline leg 138/140 is attached a stylet 142 and 144. Each spline leg 138/140 is preformed with resilient memory to achieve a desired maximum radius of curvature (which FIG. 41 shows).

The spline leg stylets 142/144 are joined through a junction 146 to a common control stylet 148. The common control stylet 148 passes through the catheter body lumen 36 to a suitable slidable control knob 150 in the handle 18, as already described. By sliding, the control knob 150 moves the control stylet 148 to change the flexure of the spline legs 138/140.

When the control stylet 148 is fully withdrawn, as FIG. 41 shows, the junction 146 is located near the base 26 of the structure 136, and the spline legs 138/140 assume their preformed maximum radii of curvatures. The spline legs 138/140 form individual half-loop structures (like shown in FIG. 7) that together emulate a full-loop structure (like that shown in FIG. 1), except for the presence of a connecting, distal hub 24.

Forward movement of the control stylet 148 first moves the junction 146 within the confines of the structure 136, as FIG. 42 shows. The forward movement of the control stylet 148 is translated by the spline leg stylets 142/144 to urge the spline legs 138/140 apart. The distal end of the bifurcated structure 136 opens like a clam shell.

As the spline legs 138/140 separate, they distend. The control stylet 150 thus compresses the splines legs 138/140 to press them into contact with the tissue area along opposite sides of the structure 136. In this way, the bifurcated structure 136 emulates the full-loop structure 78, when distended (as FIG. 16 shows).

Continued forward movement of the control stylet 150 (as FIG. 43 shows) moves the junction 146 and attached spline leg stylets 142/146 out beyond the confines of the structure 136. This continued forward movement extends the spline legs 136/140, while moving them radially inward. This, in effect, collapses the bifurcated structure 136 into a relatively low profile configuration for vascular introduction. In this way, the bifurcated structure 136 emulates the full-loop structure 78, when elongated (as FIG. 15 shows).

FIGS. 44 and 45 show an alternative embodiment of a bifurcated full-loop structure 152. The structure 152 includes two oppositely spaced spline legs 154/156, each carrying one or more electrode elements 28, like the structure 136 shown in FIGS. 41 to 43. Each spline leg 154/156 is preformed with a resilient memory to assume a desired maximum radius of curvature (which FIG. 44 shows).

Unlike the structure 136 shown in FIGS. 41 to 43, the structure 152 shown in FIGS. 44 and 45 fixes both ends of the spline legs 154/156 to the base 26. The spline legs 154/156 thereby form stationary, side-by-side half-loop structures, each with an inner portion 158 and an outer portion 160. Together, the stationary half-loop structures create the bifurcated full-loop structure 152.

In this arrangement, a center stylet 162 is attached to a ring 164 that commonly encircles the inner portions 158 of the spline legs 154/156 along the center of the structure 152. Movement of the stylet 162 slides the ring 164 along the inner leg portions 158. The stylet 162 passes through the catheter body lumen 36 to a suitable control in the handle (not shown), as already described.

Forward movement of the ring 164 (as FIG. 45 shows) jointly extends the spline legs 154/156, creating a low profile for vascular introduction. Rearward movement of the ring 164 (as FIG. 44 shows) allows the resilient memory of the preformed spline legs 154/156 to bow the legs 154/156 outward into the desired loop shape.

FIG. 46 shows another alternative embodiment of a bifurcated full-loop structure 166. This structure 166 has two oppositely spaced spline legs 168 and 170, each carrying one or more electrode elements 28. Each spline leg 168/170 is preformed with a resilient memory to assume a maximum radius of curvature (which FIG. 46 shows).

The near end of each spline leg 168/170 is attached to the base 26. The far end of each spline leg 168/170 is individually attached to its own stylet 172/174. Instead of joining a common junction (as in the structure 136 shown in FIGS. 41 to 43), the spline stylets 172/174 of the structure 166 individually pass through the catheter body lumen 36 to suitable control knobs (not shown) in the handle 18. Like the embodiment shown in FIGS. 44 and 45, a third stylet 176 is attached to a ring 178 that encircles the spline stylets 172 and 174. The third stylet 176 passes through the guide tube lumen 36 to its own suitable control knob (not shown) in the handle 18.

The embodiment shown in FIG. 46 allows the physician to move the ring 178 up and down along the spline stylets 172 and 174 to shape and change the flexure of the structure 166 in the manner shown in FIGS. 44 and 45. Independent of this, the physician can also individually move the spline stylets 172 and 174 to further shape and change the flexure of each spline leg 168 and 170, as in the case of the movable spline legs 120/122 shown in FIGS. 36 to 38. This structure 166 thus gives the physician latitude in shaping the loop structure to achieve the desired contact with the atrial wall.

Another alternative embodiment of a bifurcated full-loop structure 180 is shown in FIGS. 47 to 49. In this embodiment, the structure 180 includes two oppositely spaced spline legs 182 and 184, each carrying one or more electrode elements 28. Each spline leg 182/184 is preformed with a resilient memory to assume a desired maximum radius of curvature (which FIG. 49 shows).

The inner portion 186 of each spline leg 182/184 is attached to the base 26. A stationary ring 190 encircles the inner portions 186 near the distal end of the structure 180, holding them together.

The outer portion 188 of each spline leg 182/184 is free of attachment to the base 26 and is resiliently biased away from the base 26. Each outer portion 188 is individually attached to its own stylet 192 and 194. The spline stylets 192 and 194 individually pass through the catheter body lumen 36 to suitable control knobs (not shown) in the handle 18.

Pulling the spline legs stylets 192/194 rearward pulls the outer portion 188 of the attached spline leg 182/184 radially toward the base 26, against their resilient memories, creating a low profile suitable for vascular access (as FIG. 47 shows). Pushing the spline stylets 192/194 forward pushes the outer portion 188 of the attached spline leg 182/184, aided by the resilient memory of the spline leg 182/184, outward (as FIGS. 48 and 49 show). The spline stylets 192/194 can be manipulated together or individually to achieve the shape and flexure desired.

5. Loop Support Structures for Movable Electrodes

FIGS. 50 and 51 show a full-loop structure 196 which supports a movable ablation element 198. The structure 196 includes a pair of spline legs 200 secured at their distal ends to the hub 24 and at their proximal ends to the base 26, in the manner described in association with the structure shown in FIG. 1. A center stiffener 202 extends between the base 26 and the hub 24 to lend further strength.

The ablation element 198 (see FIG. 52) comprises a core body 204 made of an electrically insulating material. The body 204 includes a central lumen 206, through which one of the spline legs 200 passes. The core body 204 slides along the spline leg 200 (as shown by arrows in FIGS. 50 to 52).

In the illustrated and preferred embodiment (see FIG. 52), a coil electrode element 34 (as already described) is wound about the core body 204. Alternatively, the core body 204 can be coated with an electrically conducting material or have an electrically conducting metal band fastened to ft. As shown in FIG. 53, the ablation element can also comprise a composite structure 198(1) (see FIG. 53) of two bi-polar electrodes 208 separated by an electrically insulating material 210. The core body 204 of the electrode can range in diameter from 3 Fr to 8 Fr and in length from 3 mm to 10 mm.

A guide sire 212 is attached to at least one end of the ablation electrode 198 (see FIGS. 50 and 52). The guide wire 212 extends from the handle 18 through the catheter body lumen 36, along the center stiffener 202 and through the hub 24 for attachment to the ablation element 198. A signal wire 214 also extends in common along the guide wire 212 (see FIG. 52) to supply ablation energy to the electrode 198. The proximal end of the guide wire 212 is attached to a suitable control knob (not shown) in the handle 18. Movement of the guide wire 212 forward pushes the ablation element 198 along the spline leg 200 from the distal end of the structure 196 to the proximal end.

Two guide wires (212 and 213) may be used (as FIG. 52 shows), which are attached to opposite ends of the ablation element 198. Pulling on one guide wire 212 advances the electrode 198 toward the distal end of the structure 196, while pulling on the other guide wire 213 advances the electrode 198 in the opposite direction toward the proximal end of the structure 196. In an alternative implementation (not shown), the distal tip of a second catheter body can be detachably coupled either magnetically or mechanically to the movable electrode 198. In this implementation, the physician manipulates the distal end of the second catheter body into attachment with the electrode 198, and then uses the second catheter body to drag the electrode 198 along the structure 196.

In use (as FIG. 54 shows), once satisfactory contact has been established with the atrial wall 86, sliding the ablation electrode 198 along the spline leg 200 while applying ablation energy creates a long and thin lesion pattern. The ablation can be accomplished by either moving the electrode 198 sequentially to closely spaced locations and making a single lesion at each location, or by making one continuous lesion by dragging the electrode 198 along the tissue while ablating.

One or both spline legs 200 can also be movable with respect to the base, as before described, to assure intimate contact between the ablation element 198 and the endocardium.

6. Bundled Loop Structures

The assembly of bundled, independently adjustable loop structures to form a dynamic three dimensional electrode support structure 228, like that shown in FIGS. 55 to 58, are also possible.

The structure 228 shown in FIGS. 55 to 58 comprises four spline legs (designated L1, L2, L3, and L4) circumferentially spaced ninety degrees apart. Each spline leg L1, L2, L3, and L4 is generally like that shown in FIG. 29. Each leg L1, L2, L3, and L4 is preformed with resilient memory to assume a curve of selected maximum radius. In the illustrated embodiment, each leg L1 to L4 carries at least one electrode element 28, although one or more of the legs L1 to L4 could be free of electrode elements 28.

The outer portions 230 of each spline leg L1 to L4 are attached to the structure base 26. As FIG. 61 shows, the base 26 is similar to that shown in FIG. 30*b*, having an outer ring 236 and a concentric slotted inner element 238, through which the near ends of the outer spline leg portions 230 extend. The near ends are doubled back upon themselves and wedged in the space 240 between the outer ring 236 and inner element 238, as earlier shown in FIG. 6*b*.

The inner portions 232 of each spline leg L1, L2, L3, and L4 are not attached to the base 26. They pass through lumens 242 in the inner element 238 of the base 26 (see FIG. 61) and into catheter body lumen 36 for individual attachment to control knobs 234 on the handle 18 (see FIG. 55). Wires 58 associated with the electrode elements 28 carried by each leg L1 to L4 pass through other lumens 244 in the inner element 238 (see FIG. 61).

Figure 55:
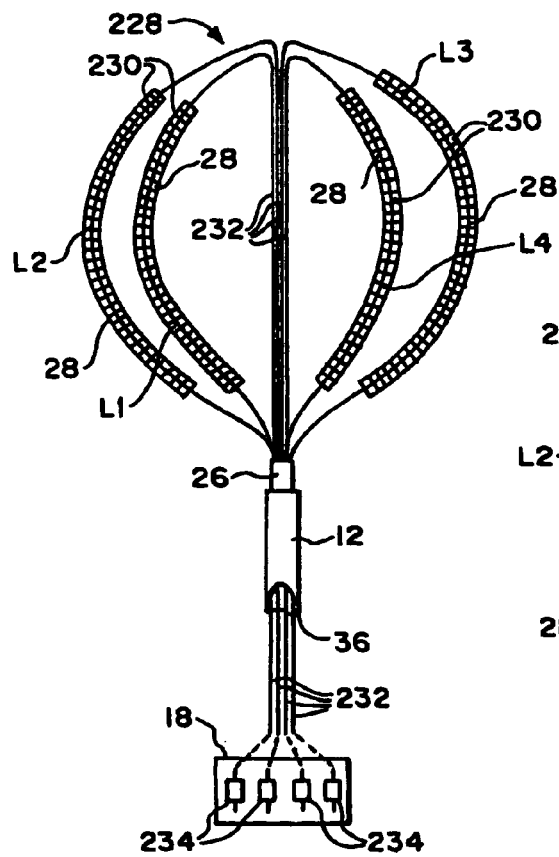
FIG. 55 is a perspective, elevation view of a bundled loop structure for supporting multiple electrode elements, comprising an array of individual spline legs structures, each having a movable portion that independently extends and distends the individual structures to shape and flex the overall bundled loop structure.
Figure 57:
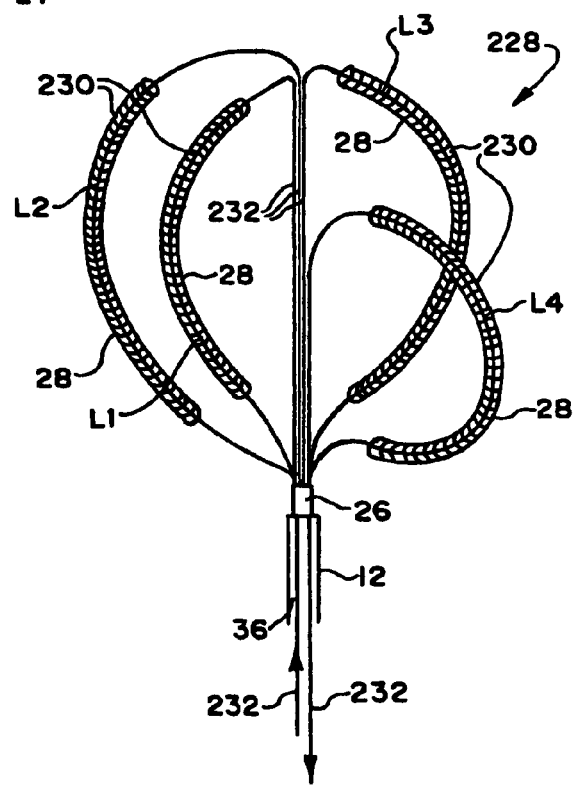
FIG. 57 is a perspective elevation view of the bundled loop structure shown in FIG. 55 with some of the independently movable spline legs extended and distended to change the flexure of the bundled loop structure.
Figure 56:
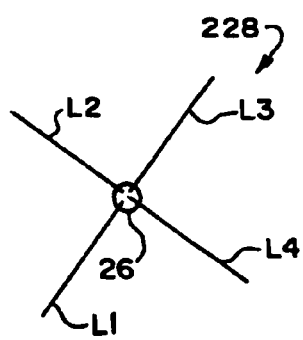
FIG. 56 is a top view of the bundled loop structure shown in FIG. 55.
Figure 58:
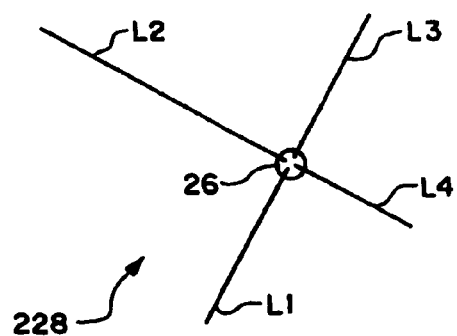
FIG. 58 is a top view of the bundled loop structure shown in FIG. 57.

The inner portion 232 of each spline leg L1 to L4 is independently movable, in the same way as the spline leg shown in FIGS. 31 to 35. By manipulating the control knobs 234, the physician can change the normal flexure of the structure 228 (which FIGS. 55 and 56 show) to a new flexure (which FIGS. 57 and 58 show), by altering the shape each spline leg L1 to L4 independent of each other. As FIGS. 57 and 58 show, the inner portion 232 of leg L4 has been pulled aft, compressing the associated loop. The inner portion 232 of leg L2 has been pushed forward, expanding the associated loop.

Figure 59A:
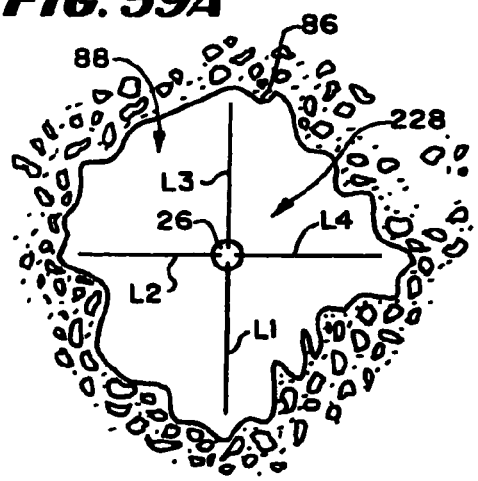
FIGS. 59a and 59b are, respectively, top and side views of a bundled loop structure like that shown in FIG. 55 in position within an atrium, out of contact with the surrounding atrial wall.
Figure 60A:
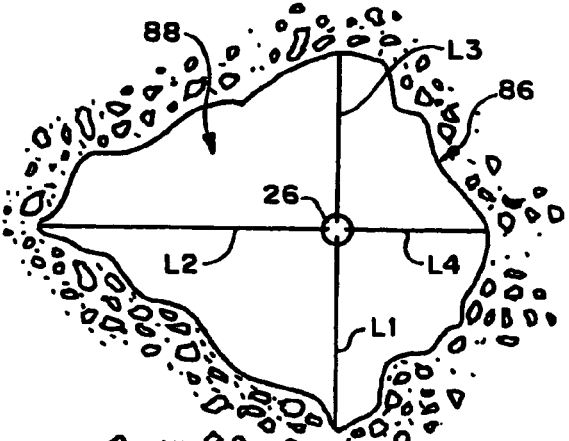
FIGS. 60a and 60b are, respectively, top and side views of a bundled loop structure like that shown in FIG. 57, with some of the independently movable spline legs extended and distended to change the flexure of the bundled loop structure, to bring it into contact with the surrounding atrial wall.
Figure 59B:
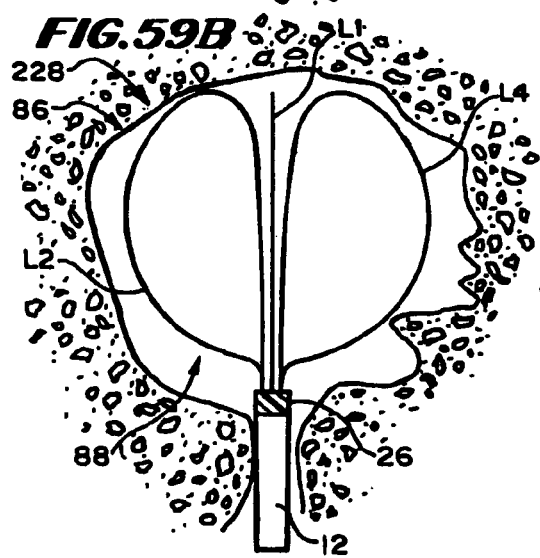
Figure 60B:
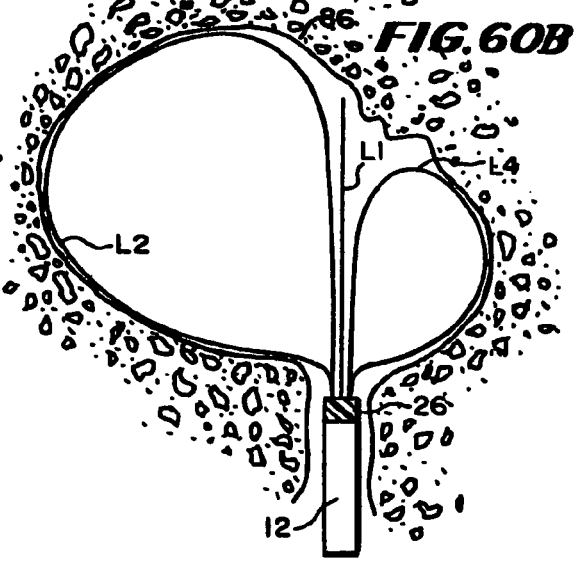

As FIGS. 59*a/b* and 60*a/b* show, by selective manipulation of the movable inner portions 232 of the spline legs L1 to L4, the physician can adjust the shape of the three dimensional loop structure 228 within the atrium 88 from one that fails to make sufficient surface contact between the electrode element 28 and the atrial wall 86 (as FIGS. 59*a/b* show) to one that expands the atrium 88 and creates an extended region of surface contact with the atrial wall 86 (as FIGS. 60*a*/60*b* show). The physician can thereby tailor the shape of the three dimensional structure 228 to the particular physiology of the patient.

In an alternative arrangement, the inner portions 232 of the spline legs L1 to L4 can be fixed to the base 26 and the outer portions 230 made free to move in the manner shown in FIGS. 47 to 49.

C. Conclusion

It should be now be apparent that one or more movable spline legs can be used in association with a movable center stylet to provide control of the shape and flexure of the ablation element. The further inclusion of steering wires on the movable stylet, or the use of a malleable stylet and/or malleable spline legs adds the ability to form curvilinear lesion patterns.

It is thereby possible to combine in a single loop support structure one or more movable spline legs (as FIGS. 31 to 38 show), a movable center stylet (as FIGS. 13 to 19 show), and a stylet steering assembly or malleable stylet/splines (as FIGS. 20 to 28 show). Such a structure is capable of creating a diverse number of shapes and contact forces to reliably achieve the type and degree of contact desired between the ablation elements and the targeted tissue area, despite physiologic differences among patients.

It should also be appreciated that the inventions discussed in this section are applicable for use in tissue ablation applications that are not catheter-based. For example, any of the loop structures like those described herein can be mounted at the end of hand-held probe for direct placement by the physician in contact with a targeted tissue area. For example, a hand held loop structure carrying multiple electrodes can be manipulated by a physician to ablate tissue during open heart surgery for mitral valve replacement.

II. Probe-Type Apparatus

As illustrated for example in FIGS. 62 and 63, a surgical device (or "probe") 250 for positioning an operative element 252 within a patient includes a relatively short shaft 254 and a bendable spline assembly 256, associated with the distal end of the shaft, for supporting the operative element. Here, the operative element 252 is in the form of a plurality of electrode elements 294, as discussed in greater detail in Section III below. Preferably, the relatively short shaft may be between approximately 4 and 18 inches in length, and is preferably 8 inches in long, while the outer diameter of the shaft is preferably between approximately 6 and 24 French. The spline assembly 256 has a predetermined use configuration. In the exemplary embodiment shown in FIGS. 62 and 63, the spline assembly includes a pair of spline legs 258 and 260 and an annular member 262 which supports the operative element 252. The surgical device also includes a tubular member 264 (a cylindrically shaped sheath in the exemplary embodiment) which covers a portion of the shaft 254 and is also slidable relative thereto. The spline assembly 256 is adapted to collapse (the insertion configuration) in response to movement of the substantially tubular member 264 in the distal direction and to expand to the predetermined use configuration when the substantially tubular member is moved in the proximal direction. A handle 266 may be provided on the proximal end of the shaft 254. The tubular member 264 preferably includes a raised gripping surface 268.

Another exemplary surgical device (or "probe") for positioning an operative element within a patient, which is generally represented by reference numeral 270, is illustrated in FIGS. 64a-65. Here, the surgical device includes a substantially triangularly shaped spline assembly 272 that consists of first and second side legs 274 and 276 and a distal leg 278. The distal leg 278, which is preferably non-linear from end to end and approximately 10 to 12 cm in length, includes first and second linear portions 280 and 282 and a bent portion 284 located mid-way between the ends. This spline configuration provides a spring force against the selected bodily surface during use (such as the atrium wall in a cardiac procedure) and the bend in the distal leg 278 optimizes the contact between the operative element 252 and the selected surface. The spline assembly 272 will collapse in the manner shown in FIG. 65 when the tubular member 264 is advanced thereover and will return to the orientation shown in FIG. 64a when the tubular member is retracted. The surgical device 270 also includes a second handle 267.

During use of the exemplary surgical device shown in FIGS. 62–65, the handle 266 (FIG. 62) or 267 (FIG. 64a) is grasped by the physician and force is applied through the shaft 254 and side legs 258 and 260 (FIG. 62) or 274 and 276 (FIG. 64a) to the operative element supporting annular member 262 (FIG. 62) or distal leg 278 (FIG. 64a). Thus, the shaft and side legs (including the area where the side legs meet) should be sufficiently strong to prevent collapse when the force is applied. The fact that the present devices are not passed through a tortured vascular path to the site of interest allows the shaft and spline legs to be stiffer than a conventional catheter shaft. This aspect of the invention is discussed in greater detail below. Alternatively, the shaft 254 and side legs 274 and 276 in the embodiment shown in FIGS. 64a and 65 may be configured such that they collapse and form a semicircle with the distal leg 278 when force is applied to the shaft (note FIG. 64b). Here, the operative element should be appropriately masked in one of the manners described below to limit contact of the operative element to the intended bodily structure.

As shown by way of example in FIG. 66, a guidewire 286 may be used to direct and/or anchor the distal leg 278 of the exemplary spline assembly 272 in an anatomical anchor site (such as one of the pulmonary veins shown in FIG. 66). The guidewire 286 passes through a lumen in the shaft 254. The distal end of the guidewire 286 passes through a lumen 288 formed in one of the spline assembly side legs 274 and 276, while the proximal end is secured to a handle 290. Alternatively, two guide wires (one passing through each of the side legs) may be used to anchor the spline assembly 272 in two anatomical anchor sites. Both wires would extend to the same handle.

The exemplary embodiments illustrated in FIGS. 62–66 may also be provided without the tubular member 264. Such devices are especially useful in surgical procedures associated with a thoracotomy or a median sternotomy, where the spline assemblies can be easily collapsed and advanced to the desired location, or advanced into the desired location without being collapsed. Here, the spline assemblies can be malleable, if desired, as opposed to simply being bendable.

Turning to FIGS. 67a and 67b, an endoscope 292 may be passed through one lumen in a tubular member 264' that has a pair of lumens. Alternatively, the shaft 254 and endoscope 292 can pass through a common lumen.

The spline assemblies illustrated in FIGS. 62–66 are preferably made from resilient, inert wire, like nickel titanium (commercially available as Nitinol material) or 17-7 stainless steel. However, resilient injection molded inert plastic can also be used. The wire or molded plastic is covered by suitable biocompatible thermoplastic or elastomeric material such as PEBAX® or Pellethane®. Preferably, the various portions of the spline assemblies comprises a thin, rectilinear strips of resilient metal or plastic material. Still, other cross-sectional and longitudinal configurations can be used. For example, the spline legs can decrease in cross-sectional area in a distal direction, by varying, e.g., thickness or width or diameter (if round), to provide variable stiffness along its length. Variable stiffness can also be imparted by composition changes in materials or by different material processing techniques. Referring more specifically to the embodiments illustrated in FIGS. 64a–66, the distal leg 278 may be configured such that the leg is flat at the distal end, but becomes more semicircular in cross-section as the leg becomes more proximal in order to taper the stiffness profile and prevent lateral movement of the spline assembly. The curvature of the spline legs may also be varied and the lateral ends of the distal leg may be reinforced in order to provide more lateral stability.

As shown by way of example in FIGS. 70a–70e, the spline assembly of the probe shown in FIGS. 64a and 65 may be replaced by a curved spline assembly 300. Here, the spline assembly includes a flat, inert wire 302 (preferably formed from Nitinol) that acts as a spring and an outer portion 304 (preferably formed from PEBAX® or Pellethane®). Viewed in cross-section, the flat wire 302 has a long side and a short side. The short sides lie in planes that are parallel to the plane shown in FIG. 70d. As such, the spline assembly 300 will deflect in the manner shown in FIGS. 70b and 70c when "in plane" forces F are applied to the spline assembly. Conversely, the assembly will resist bending when "out of plane" forces are applied in the manner shown in FIG. 70d. As such, it may be used to form an arcuate lesion during, for example, a procedure where a lesion is formed around the pulmonary vein.

It should be noted here that the wire 302 does not have to be rectangular in cross-section as shown. Other cross-sectional shapes where the length is greater than the width can also be used. The wire 302 can also be made from a malleable material such as partially or fully annealed stainless steel instead of the spring-like material discussed above. The malleable embodiments will enable the operator to form fit the ablation element support structure to irregular anatomical structures.

Figure 70C:
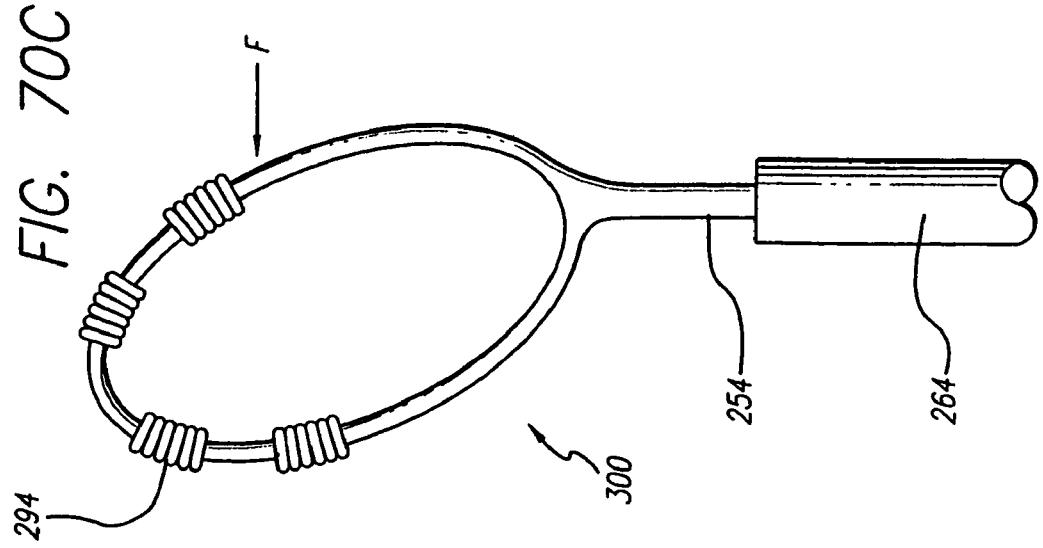
FIGS. 70a–70c are front views of a spline assembly in accordance with an embodiment of one of the present inventions.
Figure 70B:
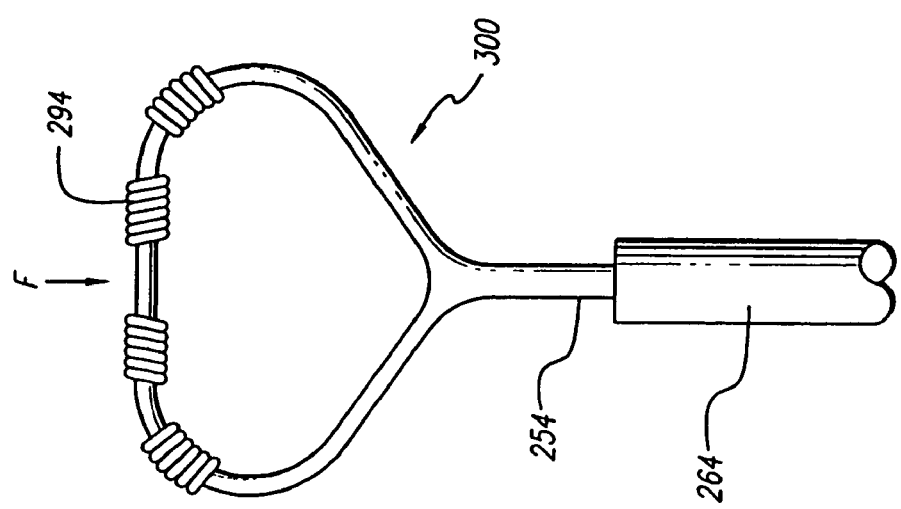
Figure 70A:
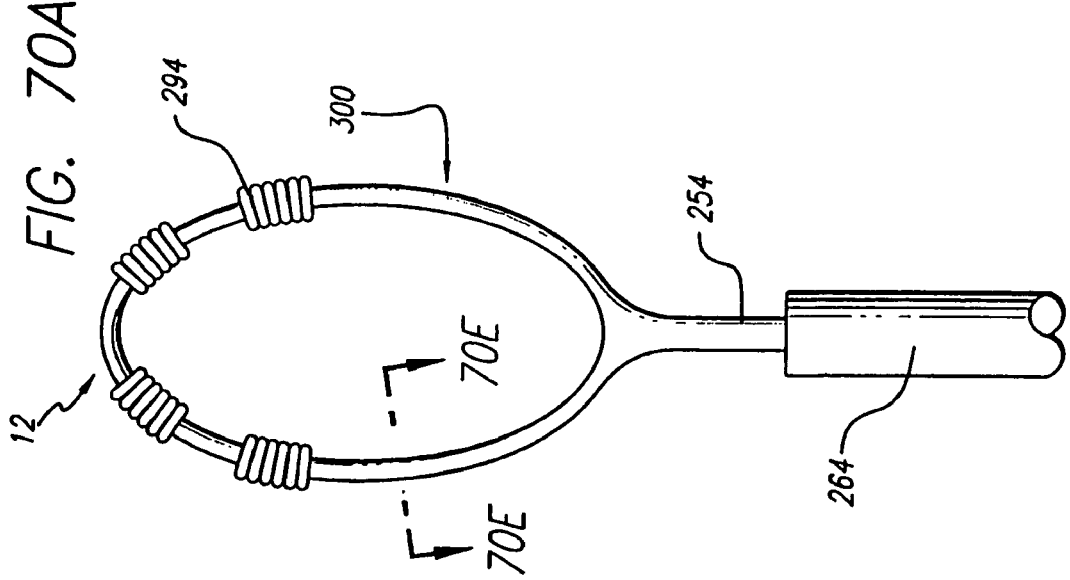
Figure 70D:
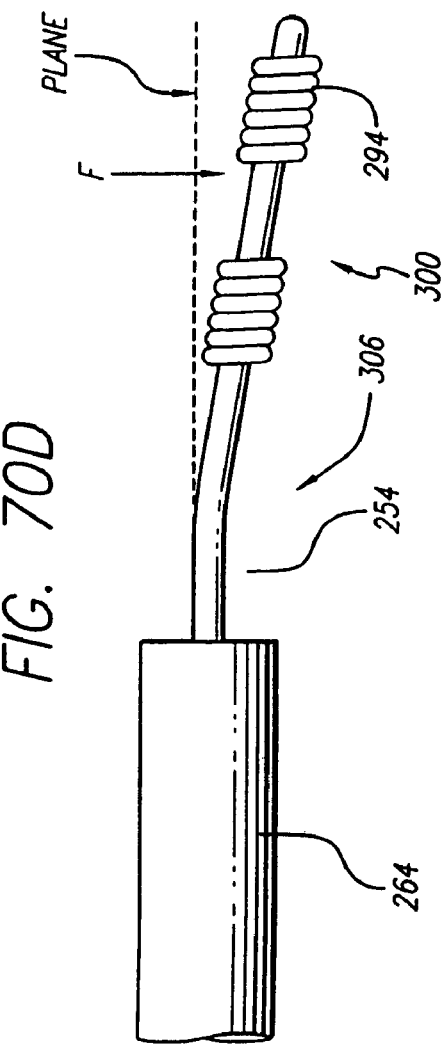
FIG. 70d is a side view of the spline assembly shown in FIGS. 70a–70c.
Figure 70E:
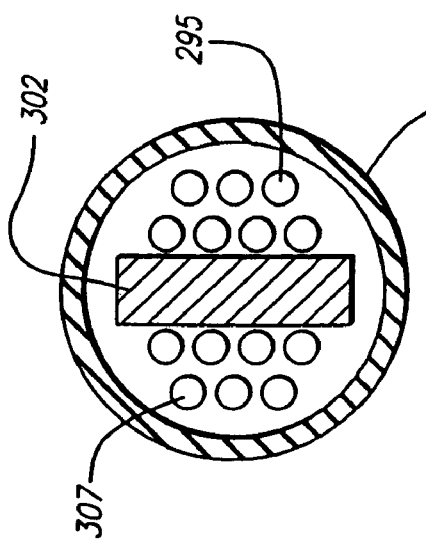
Figure 70F:
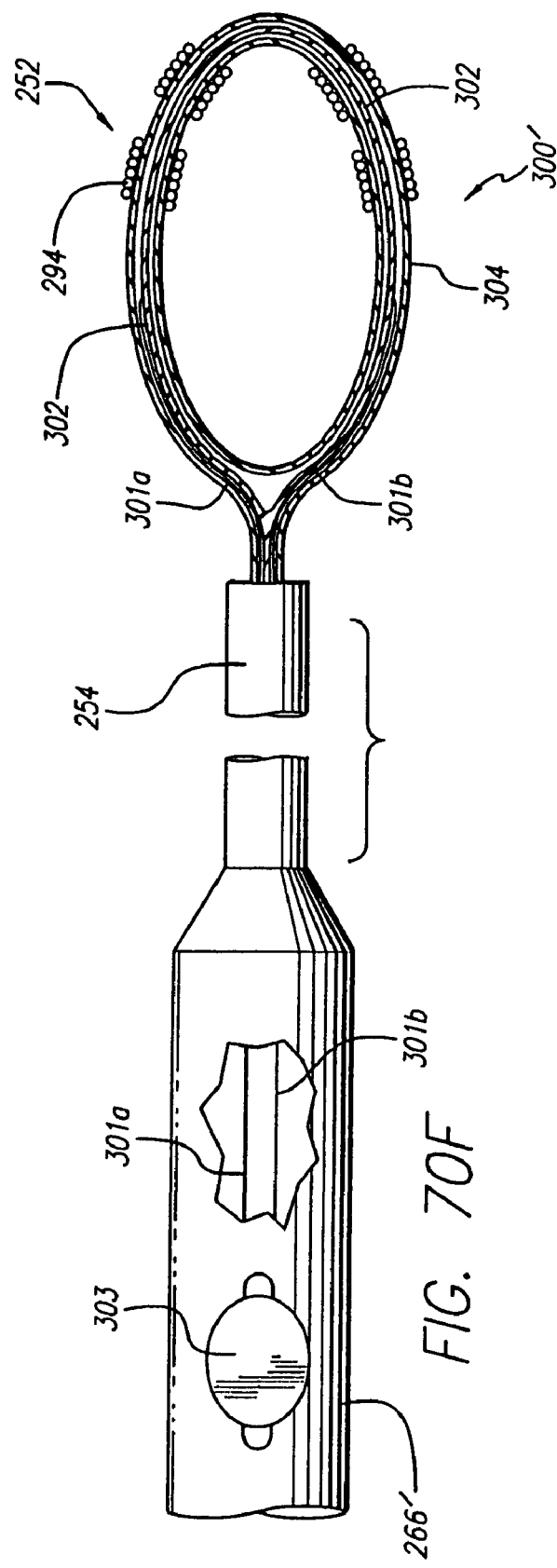
FIG. 70f is a partial front, partial section view of a surgical device for positioning an operative element within a patient in accordance with yet another preferred embodiment of one of the present inventions.

As shown in FIG. 70f, exemplary spline assembly 300' includes first and second steering wires 301a and 301b that are secured to the spring-like flat wire 302 by, for example, welding, mechanical crimping or adhesive bonding. The proximal ends of the steering wires 301a and 301b are operably connected to a knob 303 on a handle 266' by way of a cam (not shown). The handle 266' is substantially similar to the handle 266 shown in FIG. 62, but for the knob 303, cam and provisions for the steering wires 301a and 301b. Rotation of the knob 303 will cause the spline assembly to move side to side in, for example, the manner illustrated in FIG. 70c. Thus, in addition to simply moving the handle, the physician will be able to move the operative element 252 within the patient by rotating the knob 303. Such movement is useful when the physician is attempting to precisely locate the operative element within the patient and/or control the contact force between the operative element and the tissue surface. This is especially true when the handle and or shaft 254 cannot be moved, due to anatomical or surgical constraints.

In the exemplary embodiment, the steering wires 301a and 301b are both secured at about the midpoint of the flat wire loop. Other configurations are possible depending on the configuration of the loop that is desired after the knob 303 is rotated. For example, one wire could be secured closer to the top of the loop than the other. The shape of the cam may also be varied. More detailed discussions of the use of steering wires, albeit in conventional catheter settings, can be found in commonly assigned U.S. Pat. Nos. 5,195,968, 5,257,451, and 5,582,609, which are incorporated herein by reference.

The shaft 254 is preferably relatively stiff. As used herein the phrase "relatively stiff" means that the shaft (or other structural element) is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. Rigid and somewhat flexible shafts are preferably formed from stainless steel, while malleable shafts are formed from annealed stainless steel.

One method of quantifying the flexibility of a shaft, be it shafts in accordance with the present inventions or the shafts of conventional catheters, is to look at the deflection of the shaft when one end is fixed in cantilever fashion and a force normal to the longitudinal axis of the shaft is applied somewhere between the ends. Such deflection ($\sigma$) is expressed as follows:

$$\sigma = WX^2(3L-X)/6EI$$

where:
W is the force applied normal to the longitudinal axis of the shaft,
L is the length of the shaft,
X is the distance between the fixed end of the shaft and the applied force,
E is the modulous of elasticity, and
I is the moment of inertia of the shaft.

When the force is applied to the free end of the shaft, deflection can be expressed as follows:

$$\sigma = WL^3/3EI$$

Assuming that W and L are equal when comparing different shafts, the respective E and I values will determine how much the shafts will bend. In other words, the stiffness of a shaft is a function of the product of E and I. This product is referred to herein as the "bending modulus." E is a property of the material that forms the shaft, while I is a function of shaft geometry, wall thickness, etc. Therefore, a shaft formed from relatively soft material can have the same bending modulus as a shaft formed from relatively hard material, if the moment of inertia of the softer shaft is sufficiently greater than that of the harder shaft.

For example, a relatively stiff 2 inch shaft (either malleable or somewhat flexible) would have a bending modulus of at least approximately 1 lb.-in.$^2$. Preferably, a relatively stiff 2 inch shaft will have a bending modulus of between approximately 3 lb.-in.$^2$ and approximately 50 lb.-in.$^2$. By comparison, 2 inch piece of a conventional catheter shaft, which must be flexible enough to travel through veins, typically has bending modulus between approximately 0.1 lb.-in.$^2$ and approximately 0.3 lb.-in.$^2$. It should be noted that the bending modulus ranges discussed here are primarily associated with initial deflection. In other words, the bending modulus ranges are based on the amount of force, applied at and normal to the free end of the longitudinal axis of the cantilevered shaft, that is needed to produce 1 inch of deflection from an at rest (or no deflection) position.

As noted above, the deflection of a shaft depends on the composition of the shaft as well as its moment of inertia. The shaft could be made of elastic material, plastic material, elasto-plastic material or a combination thereof. By designing the shaft 254 to be relatively stiff (and preferably malleable), the surgical tool is better adapted to the constraints encountered during the surgical procedure. The force required to bend a relatively stiff 2 inch long shaft should be in the range of approximately 1.5 lbs. to approximately 12 lbs. By comparison, the force required to bend a 2 inch piece of conventional catheter shaft should be between approximately 0.2 lb. to 0.25 lb. Again, such force values concern the amount of force, applied at and normal to the free end of the longitudinal axis of the cantilevered shaft, that is needed to produce 1 inch of deflection from an at rest (or no deflection) position.

Ductile materials are preferable in many applications because such materials can deform plastically before failure due to fracturing. Materials are classified as either ductile or brittle, based upon the percentage of elongation when the fracture occurs. A material with more than 5 percent elongation prior to fracture is generally considered ductile, while a material with less than 5 percent elongation prior to fracture is generally considered brittle. Material ductility can be based on a comparison of the cross sectional area at fracture relative to the original cross area. This characteristic is not dependent on the elastic properties of the material.

Alternatively, the shaft could be a mechanical component similar to shielded (metal spiral wind jacket) conduit or flexible Loc-Line®, which is a linear set of interlocking ball and socket linkages that can have a center lumen. These would be hinge-like segmented sections linearly assembled to make the shaft.

The exemplary tubular member 264 illustrated in FIGS. 62–67b is preferably in the form of a relatively thin cylindrical sheath (e.g., with a wall thickness of about 0.005 inch) and has an outer diameter which is preferably less than 0.180 inch. The sheath material is preferably also lubricious, to reduce friction during movement of the sheath relative to the shaft 254 and spline assemblies 256 and 272. For example, materials made from polytetrafluoroethylene (PTFE) can be used for the sheath. The distal end of the sheath should be relatively flexible to prevent injury. If necessary, additional stiffness can be imparted to the remaining portion of the sheath by lining the sheath with a braided material coated with PEBAX® material (comprising polyethel block amide related to nylon). Other compositions made from PTFE braided with a stiff outer layer and other lubricious materials can be used.

Alternatively, the tubular member 264 may be relatively stiff and formed from the materials described above with respect to the shaft 254.

As shown by way of example in FIG. 71a, a surgical probe 308 in accordance with another embodiment of this invention includes a relatively stiff shaft 310, a handle 312 and a distal section 314. The shaft 310 consists of a hypo-tube 316, which is either rigid or relatively stiff, and an outer polymer tubing 318 over the hypo-tube. A relatively stiff tube, either malleable or somewhat flexible, will preferably have a bending modulus of between approximately 3 lb.-in.$^2$ and approximately 50 lb.-in.$^2$. The handle 312 is similar to the handle 266 discussed above in that it includes a PC board 320 for connecting the operative elements on the distal portion of the probe to a power source. The handle 312 preferably consists of two molded handle halves and is also provided with strain relief element 322. An operative element 254 (here, in the form of a plurality of electrode elements 294) is provided on the distal section 314. This embodiment is particularly useful because it can be easily inserted into the patient through an introducing port such as a trocar.

The handle 312 shown in FIG. 71a is intended to be used in a conventional power supply configuration, wherein power transmission from an RF generator (or other energy source) to the electrodes 294 is controlled by a foot switch. As shown by way of example in FIG. 71d, and in accordance with one embodiment of a present invention, a handle 312' is provided with a manually operable on-off switch 313. On-off switch 313 allows the physician to selectively enable and disable the supply of RF ablation energy (and other types of power) to the electrode(s) on the distal portion of the probe.

In addition to the global on-off switch 313, the exemplary handle 312" shown in FIG. 71e also includes a plurality of individual on-off switches 315 for each of the electrodes. The individual on-off switches 315 allow the physician to selectively control the supply of power to individual electrodes. The exemplary handle 312", which has seven individual on-off switches 315, is preferably used in a probe having seven electrodes. If for example, the physician intends to ablate tissue with only three of the electrodes, then the three chosen electrodes may be enabled by way of the corresponding switches 315 prior to placing the global on-off switch 313 in the "on" position.

A plurality of indicator elements 317 are also provided on the exemplary handle 312" shown in FIG. 71e. Preferably, there is one indicator element 317 for each of the on-off switches 315. In the illustrated embodiment, the indicator elements 317 are in the form of buttons that are raised when a corresponding on-off switch 315 is depressed. This provides the physician with a tactile as well as visual indication of the on-off status of the switches 315. The indicator elements 317 may also be in the form of indicator lights. Sound-based indications of the on-off status of the switches 315 may also be used. For example, a speaker on the handle or the power supply device may be employed to periodically indicate which of the switches 315 are in the "on" position.

In accordance with another aspect of the present inventions, a probe may be configured such that the handle is re-usable and the remaining portions of the probe are disposable or separately re-usable. Turning to FIGS. 71f and 71g, exemplary handle 312" includes an edge-type connector having a first portion 319 on the handle and a second portion 321 on the remaining portion of the probe. In the illustrated embodiment, the remaining portion is primarily the shaft 310 which, as described above, supports a plurality of electrode elements (not shown).

The first and second connector portions 319 and 321 have elements that will mechanically couple the handle to the remaining portion of the probe and release the two when desired. The first and second connector portions will also connect signal wires from the electrodes (or other operative elements) and temperature sensors to the energy source. A locking mechanism (not shown) may be used to maintain the integrity of the connection between the two connector portions. A cable 323 may be provided to connect the handle to an energy source.

The handles shown in FIGS. 71e–71g may be used with any of the probes disclosed herein and the features of such handles may be incorporated into any of the other handles disclosed herein.

Figure 71I:
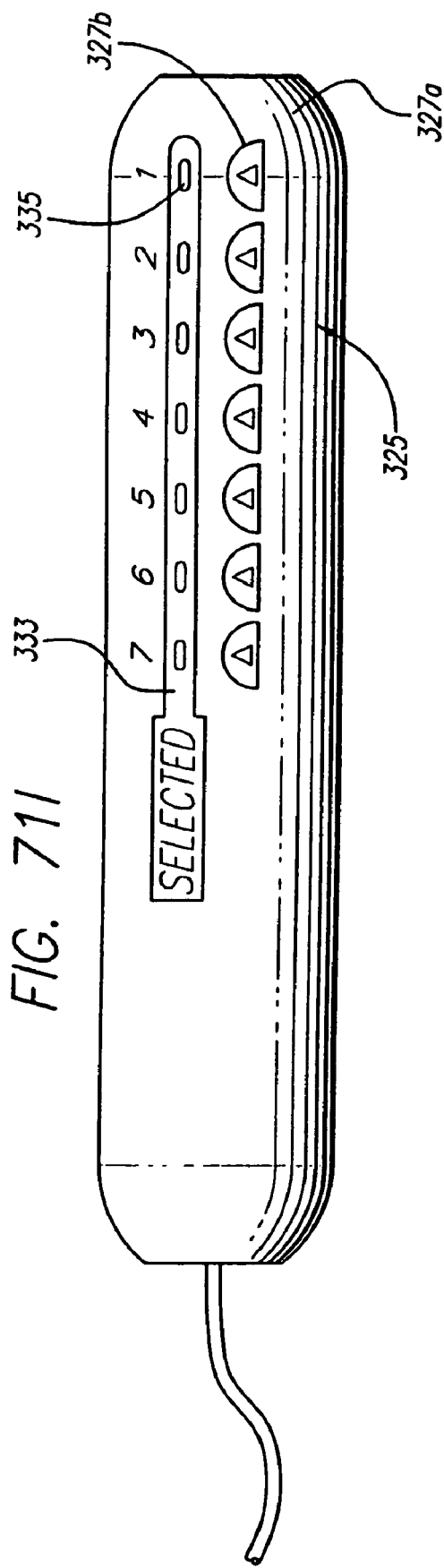
FIG. 71i is an enlarged view of the remote power control unit shown in FIG. 71h.

As shown by way of example in FIGS. 71h and 71i, and in accordance with one embodiment of a present invention, a remote power control unit 325 may be used in conjunction with a surgical probe 308 or a catheter (not shown). The remote power control unit 325 includes a main body 327a and a plurality of on/off switches 327b. Preferably, there is one on/off switch 327b for each electrode and, in the illustrated embodiment, there are seven electrodes and seven on/off switches. The remote power control unit can also include a global power on/off switch (not shown). Alternatively, a foot pedal (not shown) may be provided to perform the same function.

The size and shape of the remote power control unit 325 allow it to be easily grasped in one hand by the physician or other member of the operating room staff. Preferably, the remote power control unit 325 is about 8 inches in length, about 1.5 inches in width and about 0.5 inches in thickness. Of course, the size and shape can be adjusted to suit particular needs.

The remote power control unit 325 may be used in conjunction with conventional electrophysiology power control units, such as that shown in U.S. Pat. No. 5,545,193, that are connected to a source of energy (such as ablation energy) and provide individual electrode control. To facilitate such use, the remote control device includes a connection apparatus which, in the illustrated embodiment, consists of a cable 329a and a connector 329b. The cable 329a should be relatively long, i.e. between about 6 feet and about 15 feet in length and is preferably 10 feet. The connection apparatus can also be in the form of a wireless transmitter/receiver arrangement or any other suitable device. The surgical probe 308 is also connected to the electrophysiology power control unit. When a foot pedal is used, it too is connected to the electrophysiology power control unit.

The exemplary remote power control unit 325 includes indicia 333 in the shape of the distal portion of a surgical probe, indicator lights 335, and numbers corresponding to the respective electrodes on the probe. The combination of indicia, lights and numbers allows the physician to readily determine which electrodes are enabled and which electrodes are disabled.

The surgical probe 308 (as well as the other probes disclosed herein) and the remote power control unit 325 are sterilizable. To that end, these devices are either entirely hermetically sealed or selected portions, such as those enclosing electronic components, are sealed. Those components which are not sealed are penetrable by a gas sterilant, such as ethylene oxide (EtO). The surgical probes and remote power control units should also be splash-proof.

In those instances where a malleable shaft 310 is desired, the hypo-tube 316 may be the heat treated malleable hypotube 316 shown in FIGS. 71a, 73 and 74. By selectively heat treating certain portions of the hypo-tube, one section of the hypo-tube (preferably the distal section) can be made more malleable than the other. This will alleviate any discontinuity between the distal section 314 and the shaft 310 when the distal section is malleable.

A plurality of temperature sensing elements (such as thermocouples which are not shown) may be located on, under, abutting the longitudinal end edger of, or in between, the electrode elements 294 in any of the exemplary devices disclosed herein. Additionally, a reference temperature sensing element may be provided. For example, a reference temperature sensing 324 may be located in the handle so that room temperature will be used as the reference as shown in FIG. 71a. The reference temperature sensor may, alternatively, be provided on or near the distal tip of the device. Another alternative is to use an electronic circuit to function as the reference temperature sensor. A reference temperature sensor can also be placed on the patient or in the operating room and the physician can simply input the reference temperature into the power control device. It should be noted that the accuracy of the reference temperature sensor is less important in applications where the patient is on bypass because the convective cooling effects of blood flowing past the electrodes is substantially reduced. Also, the present surgical devices provide better tissue contact than conventional catheter-based devices, which provides more accurate temperature monitoring.

The distal section 314 can be either somewhat flexible, in that it will conform to a surface against which it is pressed and then spring back to its original shape when removed from the surface or, as noted above, malleable. A bending modulus of between 3 lb.-in.$^2$ and 50 lb.-in.$^2$ is preferred. As shown by way of example in FIG. 72a, a somewhat flexible distal section 314 may include a spring member 330, which is preferably either a solid flat wire spring (as shown), a round wire, or a three leaf flat wire Nitinol spring, that is connected to the distal end of the hypo-tube 316. Other spring members, formed from materials such as 17-7 or carpenter's steel, may also be used. A series of lead wires 332 and 334 connect the electrode elements 294 and temperature sensor elements, respectively, to the PC board 320. The spring member 330 and leads wires 332 and 334 are enclosed in a flexible body 336, preferably formed from PEBAX® material, polyurethane, or other suitable materials. The spring member 330 may also be pre-stressed so that the distal tip is pre-bent in the manner shown in FIG. 71a. Also, an insulating sleeve 331 may be placed between the spring member 330 and the lead wires 332 and 334.

In those instances where a malleable distal portion 314 is desired, the spring member 330 may be replaced by a mandrel 337 made of suitably malleable material such as annealed stainless steel or beryllium copper, as illustrated for example in FIG. 72b. The mandrel will ideally be fixed to the distal tip of the device (by, for example, soldering, spot welding or adhesives) and run through the shaft into the handle where it will also be fixed to insure good torque transmission and stability of the distal tip. Alternatively, the malleable mandrel may be fixed directly within the distal end of the shaft's hypo-tube 316 and secured by, for example, soldering, spot welding or adhesives.

Figure 72C:
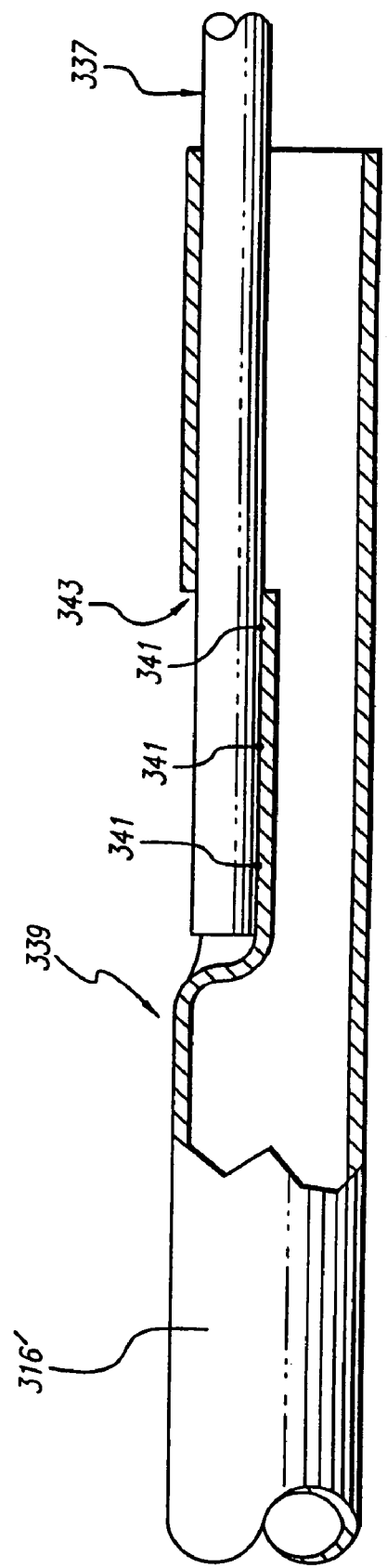

Alternatively, and as shown by way of example in FIG. 72c, a slot 339 may be formed in the hypotube 316'. The malleable mandrel 337 is inserted into the slot 339 and then held in place by spot welds 341 (shown), solder or adhesive. The slot 339 includes an opening 341 at one end thereof through which the mandrel 337 extends. The slot 339 could also include another opening at the other end. The slot 339 is located in spaced relation to the proximal end of the hypotube 316' to create additional support for the mandrel 337 when it is bent and formed into various shapes. By shortening the length of the mandrel 337, the torque of the shaped distal assembly is increased relative to the embodiment described above wherein the mandrel is anchored within the handle.

The distal portion 314 may also be formed by a hypo-tube that is simply a continuation of the shaft hypo-tube 316. However, the distal end hypo-tube can be a separate element connected to the shaft hypo-tube 316, if it is desired that the distal end hypo-tube have different stiffness (or bending) properties than the shaft hypo-tube.

The shaft 310 may be from 4 inches to 18 inches in length and is preferably 6 to 8 inches. The distal portion 314 may be from 1 inch to 10 inches in length and is preferably 2 to 3 inches. To facilitate the formation of long continuous lesions, the distal portion 314 preferably includes six spaced electrode elements 294 that are approximately 12 mm in length. The number and length of the electrode elements 294 can, of course, be varied to suit particular applications.

In accordance with some embodiments of this invention, and as shown by way of example in FIGS. 71*b* and 71*c*, the distal section 314 may be provided with a distal (or tip) electrode. Referring first to FIG. 71*b*, the distal electrode 326 may be a solid electrode with a through hole for one or more temperature sensors. Another exemplary electrode is the shell electrode 328 shown in FIG. 71*c*, which could also have one or more temperature sensors inside. The distal electrodes have a variety of applications. For example, a distal electrode may be dragged along an anatomical surface to create a long lesion. The distal electrode may also be used to touch up lesions (straight or curvilinear) created by electrode elements 294 if, for example, the distal section 314 does not exactly conform to the anatomical surface, and to continue lesions formed by the electrode elements. The distal electrode may also be used to create lesions in anatomical ridges that are shaped such that the integrity of the surgical device would be compromised if the distal section 314 were bent to conform to the ridge.

As shown by way of example in FIG. 74, an exemplary surgical probe 340 is provided with a pull wire 342 that allows the physician to adjust the curvature of the distal portion 314 from no curve, to a slight curve, an extreme curve, or even a loop, as desired. The pull wire distal portion 344 is connected to the distal tip of distal section 314. The distal portion of the pull wire enters the shaft proximal to the ablation electrodes, and the proximal portion 346 exits through an aperture formed in the handle 312. But for the pull wire 342, the probe 340 is substantially the same as the spring tip probe version shown in FIGS. 71*a* and 72*a*. Alternatively, the proximal portion of the pull wire 342 may be associated with a handle/knob arrangement such as that shown in FIG. 70*f*.

In accordance with another embodiment of this invention, and as illustrated for example in FIGS. 75 and 76, a surgical probe 348 is provided with a distal loop structure 350 that includes an operative element 252 in the form of a plurality of electrodes 294. The distal loop structure 350, which extends through an opening 352 in a sheath 354, is connected to a shaft 356. The shaft is, in turn, connected to the handle 312. The proximal portion of the sheath 354 includes a handle 358 that allows the sheath to be moved distally and proximally. The stiffness of the loop structure 350 is less than that of the sheath 354. As such, when the sheath 354 is pulled in the proximal direction, the loop structure 350 will bulge out of the sheath opening 352 in the manner shown in FIG. 75. When the sheath 354 is returned to its distal most position, the loop structure 350 will slide back into the sheath such that the sheath and the loop structure are coaxial.

The exemplary loop structure 350 is similar to the distal portion 314 of the probe shown in FIGS. 71*a* and 72*a* in that it includes a spring member (not shown), such as a leaf spring or a flat wire spring (preferably formed from Nitinol), which is covered by a flexible material such as a PEBAX® tube 359. In addition to allowing the distal portion 350 to bulge outwardly, the spring member can be flat so that it also provides resilience which helps the distal portion conform to the anatomical surface of interest and prevents "out of plane bending."

In the exemplary embodiment illustrated in FIGS. 75 and 76, a pivot assembly 360 is provided on the distal end of the sheath 354. The pivot assembly 360 includes a base member 362 and a pivot member 364 which is secured to the base member by a pivot pin 366. Referring more specifically to FIG. 76, the pivot member 364 pivots within a slot 368 that is formed in the base member 362. The size and shape of the slot 368, and the location of the pivot member 364 therein, may be adjusted to adjust the shape of the loop. For example, the location of the pivot member 364 and the shape and size of the slot 368 may be varied such that the pivot member can only rotate 30, 60, 90 or 180°. However, up to 270° of rotation is possible. The pivot member 364 includes a connector 372 (such as the illustrated threaded or barbed connector) for securing the distal end of the loop structure 350 to the pivot member.

The rigidity, malleability, or flexibility of the probe 348 may be provided in a number of ways. For example, the sheath 354 may be formed from a rigid stainless steel hypo-tube, a relatively stiff somewhat flexible stainless steel hypotube, or a relatively stiff malleable annealed stainless steel hypo-tube. Additionally, or alternatively, the shaft 356 may be a rigid (or somewhat flexible) stainless steel hypo-tube or a malleable annealed stainless steel hypo-tube. In either case, the distal end 374 of the shaft 356 will abut the flexible portion of the loop structure 350. Other materials can, of course, be used in place of stainless steel. A rigid high durometer plastic tube, for example, may be substituted for the stainless steel hypo-tube in the sheath or shaft.

Once the sheath 354 and shaft 356 are positioned relative to one another such that the desired loop is produced, the sheath may be secured to the shaft by a touhy borst connector 376 that is secured to the distal end of the sheath 354 between the handle 358 and the handle 312.

An ablation probe 378 in accordance with another aspect of this invention is illustrated, for example, in FIG. 77. The probe includes a shaft 380 (similar to shafts 254, 310 or 356 described above) on which one or more ablation electrodes 294 are mounted. As described in greater detail in Section III below, masking 296 may be used to control the focus of the ablation energy and/or prevent convective cooling when the probe is in the blood pool. A handle 266 is also provided. The shaft 380 is preferably between approximately 4 and 16 inches in length, between approximately 3 and 8 mm in diameter. Additionally, the shaft may either be rigid or relatively stiff and, if relatively stiff, can be either malleable or somewhat flexible. The ablation probe 378 may be used for a variety of procedures. For example, the shaft may be inserted into the heart to perform ablation procedures.

Turning to FIGS. 95 and 96, a pressure application probe 650 may be used to apply pressure to the distal section of a probe, such as the probe 308 shown in FIG. 71*a*, or any other operative element supporting device. The application of pressure with the probe 650 can improve the level of contact between tissue and, for example, the distal section 314 of the probe 308. The pressure application probe 650 includes an elongate main body portion 652 and at least one engagement device 654. The exemplary pressure application probe shown in FIGS. 95 and 96 also includes a second engagement device 658. As discussed in detail below, the second engagement device 658 has a slightly different shape than the engagement device 654.

The main body portion 652 is preferably either rigid, malleable or somewhat flexible and about 4 inches to about 18 inches in length, although the length may be adjusted to suit particular applications. When a malleable main body portion is desired, the main body portion 652 may be formed in the manner described above with respect to the shaft 254, and preferably consists of a soft metal rod or tube, or a settable plastic rod or tube. For example, the shaft 254 may be formed from a nickel titanium rod or tube, which is ductile at room temperature and which will straighten out at elevated temperatures such as those used during autoclave sterilization. Regardless of stiffness, the outer surface of the main body portion 652 should be covered with insulating material such as PEBAX® or urethane. The engagement device 654 is preferably formed from insulating material such as polycarbonate, urethane, glass filled thermoplastic or ABS.

The engagement device may have any of a variety of configurations. In the exemplary embodiment illustrated in FIGS. 95 and 96, the engagement devices 654 and 658 are generally c-shaped, with engagement device 658 having a more open shape. In use, the c-shape helps maintain the engagement devices at the desired location on the distal portion of the surgical probe 308 so that pressure can be applied to the desired location. The open shape of the engagement device 658 allows the engagement device to be readily repositioned along the distal portion of the surgical probe without disturbing the position of the surgical probe relative to the tissue.

The c-shaped engagement device 654 can be coupled to the distal section 314 of the probe 308 as shown in FIG. 95, or any other probe, by either inserting the distal tip of the probe through the opening 656 or by snap-fitting the engagement device 654 over the distal section. When snap-fitting is desired, the engagement device should be somewhat flexible. This arrangement allows the pressure application probe 650 to be rotated relative to the probe 308 when the two are engaged. As a result, the pressure application probe 650 can be reoriented without moving the probe 308. The pressure application probe 650 may also be used to move the probe 308 within the patient when the two are engaged.

As shown by way of example in FIG. 97, an exemplary pressure application probe 660 is provided with an engagement device 662 having a relatively narrow profile. The narrow profile allows the probe 660 to engage the distal section of an operative element supporting device, such as the distal section 314 of probe 308, even when the two devices are oriented at severe angles relative to one another. Of course, the engagement device is not limited to the shapes shown in FIGS. 95–97. Any shape that is capable of engaging the distal portion of a probe may be used.

Although not limited to such a use, the pressure application probes shown in FIGS. 95–97 are especially useful in thoroscopic procedures. Here, the pressure application probe may be inserted into a patient through one port, while the electrode supporting probe is inserted through another port and connected to the pressure application probe.

Another device which may be used in conjunction with probes such as the probe 308 shown in FIG. 71a is illustrated, for example, in FIG. 98. The exemplary coupling device 664 includes a base member 666, a generally c-shaped engagement device 668 (similar to that described above) and, in the illustrated embodiment, a connecting member 670. The base member 666 and engagement device 668 can also be directly connected to one another.

Figure 99:
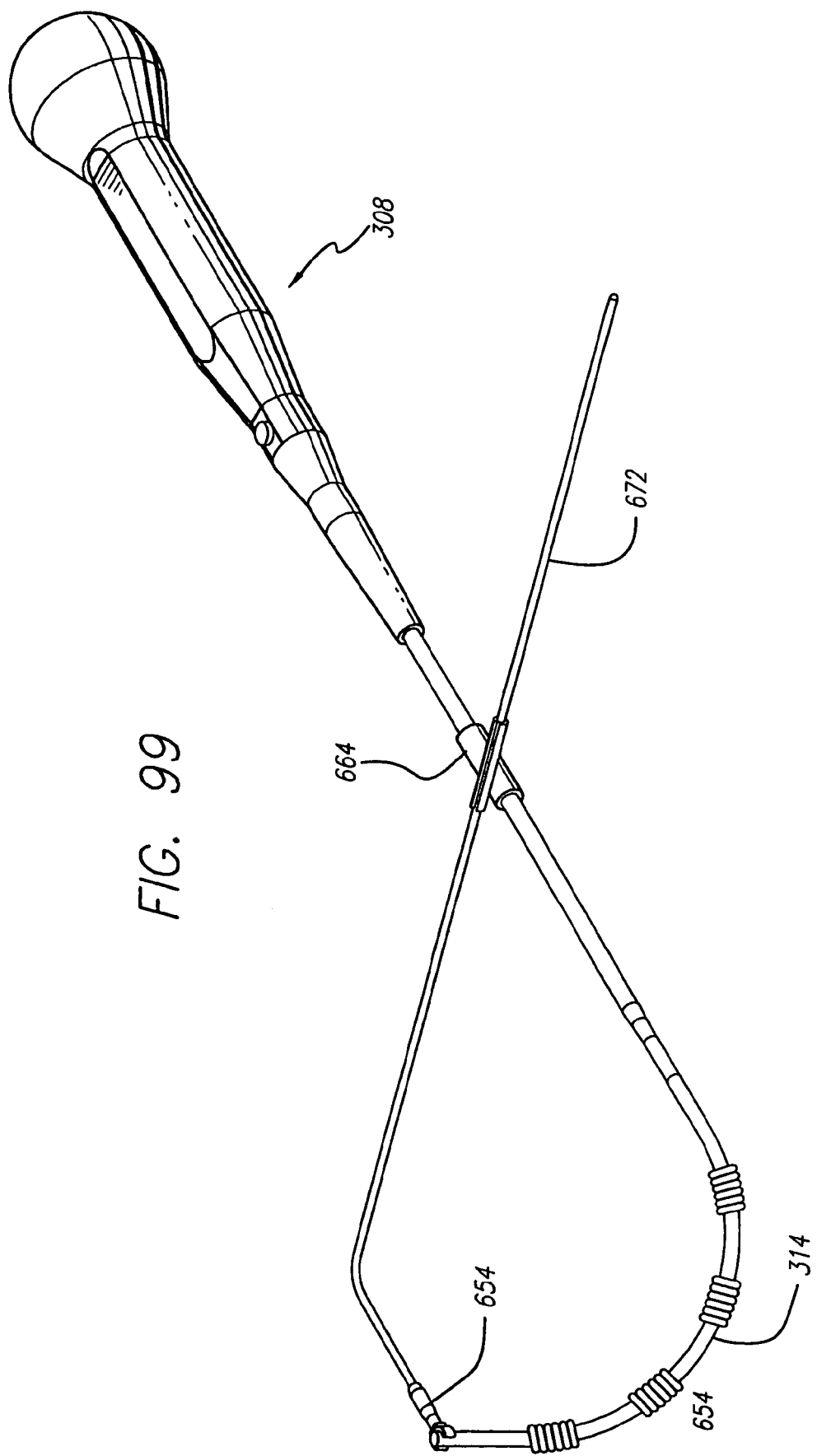

The coupling device 664 has a wide range of uses. For example, the coupling device may part of a pressure application probe 672, as shown in FIG. 99. Another exemplary use of the coupling device 664 is shown in FIG. 100. Here, the coupling device 664 is placed on a probe such as probe 308 and used to create a distal loop. The coupling device can be located at different points along the length of the probe and arranged at different rotational orientations relative to the probe (note arrows 674a and 674b) in order to control the shape of the loop. To that end, the base member 666 and a portion of the distal section 314 can include respective sets of teeth that allow the rotational orientation of the coupling device 664 to be fixed relative to the probe 308. Note teeth 676 in FIG. 101.

In order to increase the number of coupling device applications, the connecting member 670 may be configured in a variety of ways. For example, the connecting member 670 can be rigid, flexible, somewhat flexible, or malleable. The connecting member 670 can also be in the form of a swivel or pivot. The base member 666 and engagement device 668 can also be fixed at various angles relative to one another (note, for example, FIG. 99).

III. The Operative Elements

A. Exemplary Operative Elements

In the exemplary embodiments illustrated in FIGS. 62–77, the operative element 252 is made up of a plurality of electrode elements 294. Electrode elements 294 can serve a variety of different purposes, as can electrode elements 28 and 30 (FIGS. 1–61). The operative elements 252 may also be lumens for chemical ablation, laser arrays, ultrasonic transducers, microwave electrodes, and D.C. hot wires, and such devices may be substituted for the electrode elements 28 and 30.

In the illustrated embodiments, the principal use of the electrode elements is to transmit electrical energy and, more particularly, RF energy, to ablate heart tissue. However, the electrode elements can also be used to sense electrical events in heart tissue. Alternatively, or in addition, the electrode elements can serve to transmit electrical pulses to measure the impedance of heart tissue, to pace heart tissue, or to assess tissue contact using conventional pacing and sensing techniques. Once the physician establishes contact with tissue in the desired heart region, the physician applies ablating energy to the electrode elements.

In the exemplary embodiments shown in FIGS. 1–61, the electrode elements 28 are electrically coupled to individual wires 58 (see FIG. 11a) to conduct ablating energy to them. The wires 58 extend along the associated spline leg 22 (as FIG. 11a shows), through a suitable access opening provided in the base 24 (for example, the anchor lumen 226 shown in FIG. 6b) into and through the catheter body lumen 36 (as generally shown in FIG. 1 and FIGS. 30a/b), and into the handle 18, where they are electrically coupled to external connectors 38 (see FIG. 1). The connectors 38 plug into a source of RF ablation energy (not shown).

Turning to the exemplary embodiments illustrated in FIGS. 62–77, the electrode elements 294 are electrically coupled to individual wires (see reference numeral 295 FIGS. 69b and 70e and reference numeral 332 in FIGS. 72a, 72b and 73) to conduct ablating energy to them. The wires are passed in conventional fashion through a lumen extending through one of the spline legs and the shaft 254 into a PC board in the handle 266, where they are electrically coupled to a connector 296 which is received in a port 298 (see FIG. 62). The connector 296 plugs into a source of RF ablation energy. A plurality of temperature sensing elements (not shown), such as theremocouples or thermistors, may also be provided on the spline assemblies shown herein. Such temperature sensing elements may be located on, under, abutting the longitudinal end edges of, or in between, the electrode elements 294. For temperature control purposes, signals from the temperature sensor elements are transmitted to the source of ablation energy by way of wires (see reference numeral 297 in FIGS. 69b and 70e and reference numeral 334 in FIGS. 72a, 72b and 73) which are also connected to the PC board. Suitable temperature sensor elements and controllers which control power to an electrode based on a sensed temperature are disclosed in U.S. Pat. Nos. 5,456,682 and 5,582,609, which are incorporated herein by reference. The respective numbers of wires will, of course, depend on the numbers of sensors and electrodes used in a particular application. A suitable temperature control system is described below with reference to FIGS. 89–92.

The electrode elements can be assembled in various ways. They can, for example, comprise multiple, generally rigid electrode elements arranged in a spaced apart, segmented relationship. The segmented electrodes can each comprise solid rings of conductive material, like platinum, which makes an interference fit about the annular spline member. Alternatively, the electrode segments can comprise a conductive material, like platinum-iridium or gold, coated upon the device using conventional coating techniques or an ion beam assisted deposition (IBAD) process. For better adherence, an undercoating of nickel or titanium can be applied. The electrodes can also be in the form of helical ribbons.

Alternatively, the electrode elements can comprise spaced apart lengths of closely wound, spiral coils wrapped about the device to form an array of generally flexible electrode elements. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility.

Electrode elements can be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

As illustrated for example in FIG. 68, the electrode elements can also include a porous material coating 299, which transmits ablation energy through an electrified ionic medium. For example, as disclosed in U.S. application Ser. No. 08/879,343, filed Jun. 20, 1997, entitled "Surface Coatings For Catheters, Direct Contacting Diagnostic and Therapeutic Devices," which is incorporated herein by reference, electrode elements and temperature sensor elements may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

For applications in which the ablation electrode is in contact with flowing blood as well as tissue, such as when the patient is not on bypass, coating electrodes with regenerated cellulose decreases the effect of convective cooling on the electrode because regenerated cellulose is a poor thermal conductor as compared to metal. Thus, the effect of convective cooling by blood flowing past the regenerated cellulose coated electrodes is diminished. This provides better control for a lesion-generating process because the hottest tissue temperature is closer to the ablation electrode.

Furthermore, the regenerated cellulose coating decreases the edge effects attributed to delivering RF energy to an electrode having a sharp transition between the conductive electrode and insulating material. The current density along the electrode and power density within tissue are more uniform, which reduces the incidence and severity of char and/or coagulum formation. The more uniform current density along the axis of the device also results in a more uniform temperature distribution at the electrode, which decreases the requirement for precise placements of the temperature sensors at the ablation electrodes. Additionally, by coating a device with regenerated cellulose to create the outer surface, less labor-intensive methods of forming electrodes and bonding wires to electrode surfaces can be used.

During the coating process, a device such as the one of the above-described distal spline assemblies is coated with a viscose solution. The viscose solution is preferably cellulose xanthate, which is a form of solubilized cellulose derivative that is dissolved in a sodium hydroxide solution. The viscose solution is dip-coated onto the distal end assembly, which includes the electrodes, signal wires, temperature sensors, etc. The coated device is then regenerated by contacting it with an acid, such as sulfuric acid, which converts the xanthate back into the cellulose structure. The term regenerated cellulose refers to cellulose which has been converted from a solubilized cellulose derivative back into a pure cellulose structure. This regeneration process creates large enough micro size pores in the coating allowing ionic transport yet small enough to prevent ingress of blood cells, infectious agents, such as viruses and bacteria, and large biological molecules such as proteins.

Once the cellulose is regenerated, it is rinsed with water to remove acid residuals and sulfur compounds. An oxidizing agent (bleach, etc.) may be added to the rinse water to accelerate the removal of sulfur compounds. After the cellulose is regenerated, it is fully cured in an environmental chamber at a low humidity. Thereafter, it is preferable to make the regenerated cellulose flexible when dry, and to do so moisture is reintroduced into the cellulose coating material by setting the environmental chamber to a higher humidity. Alternatively, a small quantity of a material such as glycerol may be applied to the coating, and the hydroscopic nature of the glycerol will hydrate the cellulose coating to create sufficient flexibility. An overall thickness range for operable regenerated cellulose coatings is from 0.001 inches to 0.015 inches, with a preferable thickness range being from 0.001 inches to 0.003 inches; a preferred thickness being approximately 0.002 inches.

Materials other than regenerated cellulose that are mechanically robust and that have suitable characteristics could be used for the coating material. Hydrophilic materials that have effective pore sizes from 500 to 500,000 Daltons with a porosity of 1–10% and which are biocompatible could be effective. Some types of hydrogels, such as those used for disposable contact lenses are good candidate materials. Plastic materials that have additives to make them semiconductive could also be used. The loaded plastic would need to have a resistivity in the range of about 200–2,000 ohm-cm, and would need to be applicable in very thin films to the device.

The thickness of the cellulose coating is controlled by the viscosity of the coating solution and the dipping rate, and a different viscosity of the coating solution can be achieved by diluting it with the sodium hydroxide solution. A variable wall thickness can be achieved by varying the extraction rate during the dipping process. The slower the extraction rate, the thinner the wall thickness, and the faster the extraction rate, the thicker the wall thickness. An increased coating wall thickness can also be obtained by multiple layers of coating. To ensure proper lamination between such layers, each layer is coagulated with a salt solution (sodium sulfate, etc.) before applying another layer. In addition, spraying and co-extruding the viscose solution over the electrodes and the distal section can also be used to achieve a variable wall thickness cellulose coating.

In another method for covering a distal electrode assembly, a tubular casing of regenerated cellulose material is created on a mandrel. The regenerated cellulose casing is then shrunk onto the distal assembly.

The regenerated cellulose coating may also be applied over a "wet" electrode element. The moisture from the wet electrode element prevents the electrode elements from sticking to tissue during an ablation procedure. A wet electrode element is formed by a material that has high absorption capacity for liquids, such as an open cell sponge, hydrogel or cloth. Alternatively, the regenerated cellulose coating may simply be wet prior to the procedure, such as an ablation procedure.

The electrode elements may be operated in a uni-polar mode, in which the ablation energy emitted by the electrode elements is returned through an indifferent patch electrode (not shown) externally attached to the skin of the patient. Alternatively, the elements may be operated in a bi-polar mode, in which ablation energy emitted by one or more electrode elements is returned through other electrode elements. The amount of power required to ablate tissue ranges from 5 to 150 w.

The electrode elements are preferably about 4 mm to about 20 mm in length. For example, the size and spacing of the electrode elements 28 shown in FIGS. 10 and 11 *a/b* are well suited for creating continuous, long and curvilinear lesion patterns in tissue when ablation energy is applied simultaneously to adjacent emitting electrode elements. Continuous lesion patterns uniformly result when adjacent electrode elements are spaced no farther than about 2.5 times the electrode segment diameter apart. Further details of the formation of continuous, long and thin lesion patterns are found in co-pending U.S. application Ser. No. 08/763,169, filed Dec. 10, 1996, which is a File Wrapper Continuation of U.S. application Ser. No. 08/287,192, filed Aug. 8, 1994, entitled "Systems and Methods for Forming Elongated Lesion Patterns in Body Tissue Using Straight or Curvilinear Electrode Elements," which is incorporated herein by reference. Similar sizing and spacing may be used in conjunction with the other embodiments illustrated herein.

Using rigid electrode segments, the length of the each electrode segment can vary from about 2 mm to about 10 mm. Using multiple rigid electrode segments longer than about 10 mm each adversely effects the overall flexibility of the element. Generally speaking, adjacent rigid electrode segments having lengths of less than about 2 mm do not consistently form the desired continuous lesion patterns.

When flexible electrode segments are used, electrode segments longer that about 10 mm in length can be used. Flexible electrode segments can be as long as 50 mm. If desired, the flexible electrode structure can extend uninterrupted along the entire length of a support spline.

The diameter of the electrode segments 30 or 34 (FIGS. 1-61) and underlying spline leg 22 (including the flexible sleeve 32) can vary from about 2 French to about 10 French.

B. Operative Element Considerations in a Non-Convective Cooling Environment

In the exemplary embodiments shown in, for example, FIGS. 15-20, 62-67*a*, 68, 70*a-f*, 71, 74 and 75, the electrode elements are not masked. Such embodiments are particularly useful when little to no fluid flow will be present, such as when the heart is on bypass and there is no blood flow within the heart. Here, air acts as an insulator and produces only modest convective cooling effects, as compared to a flowing blood pool that has a higher convection coefficient than virtually static air. Energy transmission is, therefore, essentially limited to the RF energy that is transmitted from the portion of the electrode surface that is in contact with the tissue to either a ground electrode, or another electrode within the group of electrode elements. The overall impedance of the system will increase (as compared to a situation where blood is present) due to the smaller effective surface area between the electrode and tissue.

Both of these conditions, focused RF energy and low heat dissipation into the air, will impact the ablation because they result in a high current density with high local desposition of heat without the heat sinking that convective cooling provides. When creating long lesions with a conventional catheter, char can be created as the tip is dragged because of the high current density and the difficulty in monitoring tissue temperature and controlling power that is inherent in the dragging process. The present invention, however, can take advantage of the high current density because the electrodes are not being dragged. For example, a number of electrodes can be used to ablate simultaneously because the effective (tissue contacting) surface area between all of the ablating electrodes is smaller and the convective cooling effects are reduced, as compared to situations where blood is present. This reduces the power requirements of the system. In addition, by using electrodes with lower thermal mass (as compared to a conventional solid tip electrode), less heat will be retained by the electrode and better temperature sensing can be made at the tissue surface. This will speed up the creation of the lesions and enable better lesion creation control.

It is also noteworthy that the masking described in the following section can be useful during bypass because tissue can partially wrap around the electrodes when the distal end of the device is pressed against the tissue. Such masking can also be used to control lesion thickness.

C. Operative Element Considerations in a Convective Cooling Environment

In instances where the patient will not be on bypass and blood will be flowing past the electrodes, or in other situations when fluid flow is present, the portion of the electrode elements (or other operative elements) not intended to contact tissue may be masked through a variety of techniques with a material that is preferably electrically and thermally insulating. For example, a layer of UV adhesive (or another adhesive) may be painted on preselected portions of the electrode elements to insulate the portions of the elements not intended to contact tissue. Alternatively, a slotted sheath may be positioned over the portion of the electrode elements not intended to contact tissue. Deposition techniques may also be implemented to position a conductive surface only on those portions of the spline assembly intended to contact tissue. A coating may be formed by dipping the electrode elements in polytetrafluoroethylene (PTFE) material.

For example, as FIGS. 10 and 11*b* show, the side of the ablation elements 28 that, in use, is exposed to the blood pool may be covered with a coating 48 of an electrically and thermally insulating material. The coating 48 prevents the transmission of ablating energy directly into the blood pool.

Instead, the coating 48 directs the applied ablating energy directly toward and into the tissue.

As shown by way of example in FIG. 69a, a polymer layer 296 may be thermally fused over the electrodes 294 to mask desired portions of the electrodes. An exemplary process for applying the polymer layer is as follows. A segment of shaft tubing is cut long enough to cover the desired electrodes, and is then split in half (or other desired angle) along the axis. One half is placed over the assembled distal section so that it covers the side of the electrodes that are to be masked. A piece of polymeric shrink tubing, preferably RNF-100 or irradiated LDPE, is then carefully slid over the catheter distal end, so that the mask tubing is not moved from its placement over the electrodes and so that it stops approximately 2 cm beyond the end of the tubing half. The distal end is then heated in a controlled heat source at approximately 400° F. so that the mask tubing fuses into the distal shaft tubing along its length, and so that all of its edges are well fused into the shaft tubing, but not fused so much that the covered electrodes begin to poke through. Finally, the polymeric shrink tubing is split on one end and the assembly is heated at approximately 225° F. while the polymeric shrink tubing is slowly peeled off of the fused catheter shaft.

Additionally, as illustrated in FIG. 69b, the shape of an electrode 294' may be such that the metallic material in the region not intended to contact tissue is eliminated.

The masking techniques described in the preceding paragraphs improve the efficiency of, for example, an ablation procedure by decreasing the surface area of the electrodes and, therefore, the energy required to heat tissue. The masking can be used to form a narrow electrode which is sometimes desirable, even when the patient will be on bypass. The convective cooling effects of blood flowing by the electrode are also reduced. In addition, the transmission of RF energy to unintended anatomic structures is prevented. This is especially important in epicardial applications when the ablation electrode elements may be sandwiched between multiple anatomic structures including, for example, the aorta and pulmonary artery. The masking techniques also focus the application of ablating energy to helps to control the characteristics of the lesion.

IV. Epicardial Applications of Probe-Type Apparatus

The inventions described above (primarily those discussed above with reference to FIGS. 71a–75) may be used in a variety of epicardial procedures. One such procedure is a maze-like ablation procedure to prevent atrial fibrillation. A thoracostomy, which is a surgical procedure that is less invasive than a thoracotomy or median sternotomy, may be used to gain access to the atrium. Here, relatively small incisions are created in the intercostal space. At each of the incisions, a trocar may be used to provide a port to access the thoracic cavity. These ports may be used for visualization with fiberoptic cameras, ultrasound, or other visualization devices, as well as for the surgical devices that ablate tissue. The surgical devices may be, for example, inserted through the ports located on the left side of the patient which provide direct access to the left atrium. The devices may then be used to create long, thin, curvilinear lesions or annular lesions on the epicardial surface. If necessary, lung lobes may be deflated during the procedure by inserting an endotracheal tube that inflates the right lung only. The left lung will collapse when the chest is opened.

There is also a high prevalence of atrial fibrillation substrates proximate to the pulmonary veins. Lesions may be created on the epicardial surface around pulmonary veins or between pulmonary veins. There is, however, some difficulty associated with epicardial access due to the presence of fatty deposits in the pulmonary vein region. The devices described above can create lesions on the epicardial surface proximate to the pulmonary veins because they can penetrate through fatty deposits and exert enough force against the epicardial surface to compress the remaining fat to such an extent that the ablation electrodes contact the epicardium. It is, however, very difficult to achieve suitable contact between the tissue and the electrodes. Thus, it is preferable to perform endocardial ablation around or between pulmonary veins in the manner described below.

V. Endocardial Applications of Probe-Type Apparatus

Figure 94:
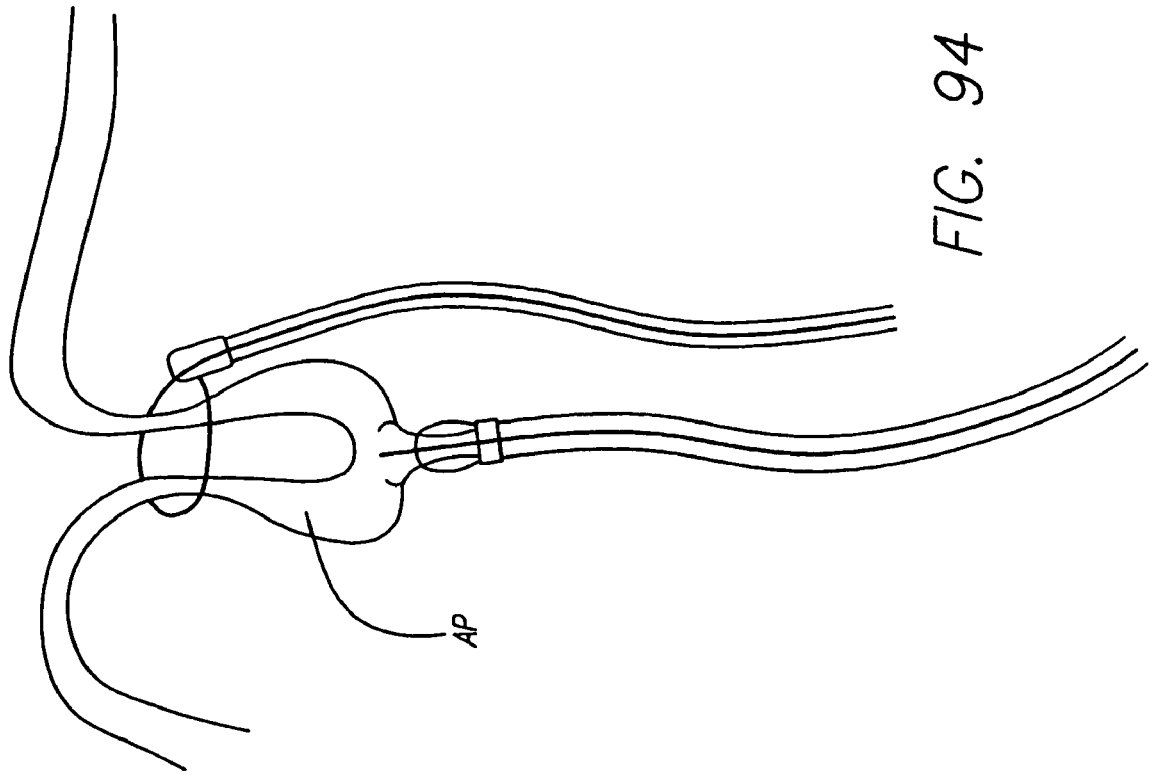
FIG. 94 is a fragmentary view of the combination shown in FIG. 93 illustrating further steps of tying an appendage in an inverted orientation.
Figure 93:
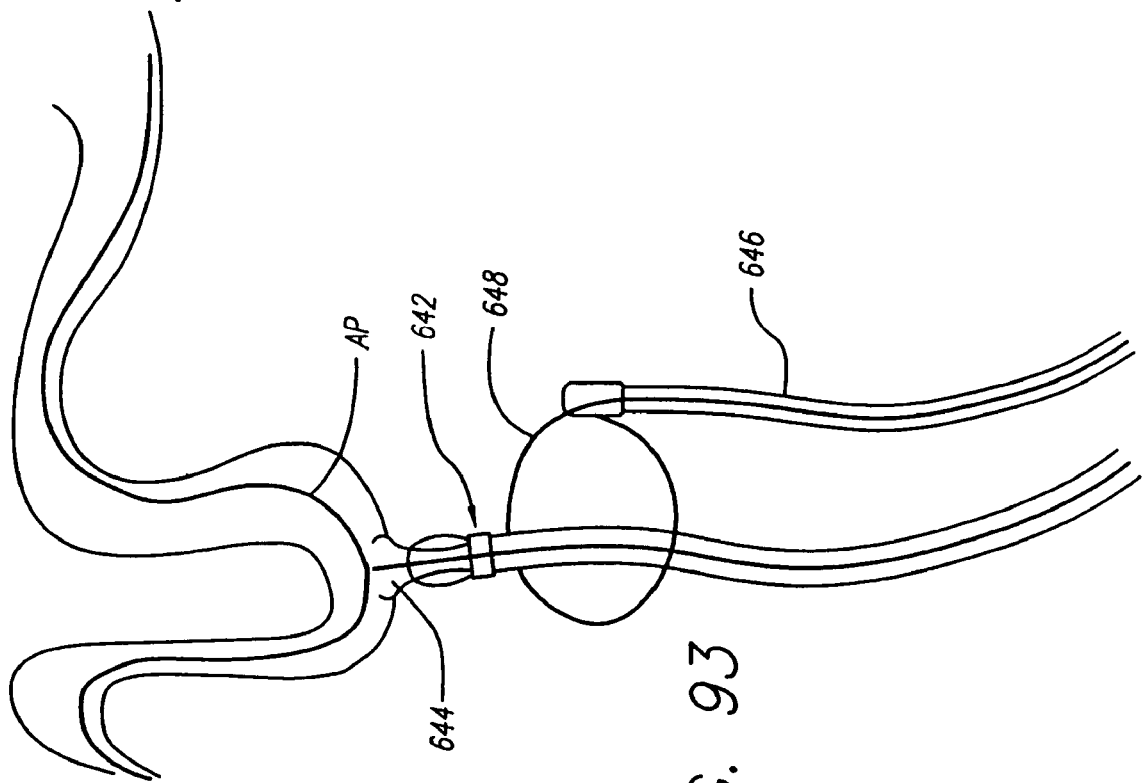
FIG. 93 is a fragmentary side view showing the use of a grabbing catheter in conjunction with a lasso catheter for maintaining the walls of the inverted appendage together.

The inventions described above may be used in a variety of endocardial procedures. To create lesions on the endocardial surface, access to the interior of the left atrium must also be obtained. To obtain thoracoscopic access to the left atrium via a thoracostomy, a cannula may be inserted through the left atrial appendage or the left atrial free wall. The preferred access point is the left atrial appendage, especially if the physician intends to isolate the left atrial appendage at the end of the procedure. More specifically, and as shown by way of example in FIGS. 93 and 94, a grabbing catheter 642 having movable grasping prongs 644, which is described in U.S. application Ser. No. 08/880,711, filed Jun. 23, 1995, entitled "Atrial Appendage Stasis Reduction Procedures and Devices" may be used to capture, pull and stretch the appendage AP. Next, a lasso catheter 646 having a lasso 648, which is also described in U.S. application Ser. No. 08/880,711, may be used to encircle the left atrial appendage near the base of the appendage. The grabbing catheter facilitates the positioning of the lasso at the base of the appendage by pulling the appendage through the lasso. A needle is then used to puncture the appendage wall and gain access to the left atrium. A guidewire is advanced through the needle into the left atrium. The needle is then removed, leaving the guidewire in place. An introducer/dilator combination is then advanced over the guidewire into the left atrium. Next, the lasso is then tightened around the introducer to prevent blood flow past the introducer into the distal region of the atrial appendage. The dilator is then removed, leaving the introducer as the access to the interior of the left atrium.

Instead of the lasso technique, a purse string technique may be employed wherein sutures are used to tighten the atrial appendage around the introducer.

One of the exemplary devices described above, such as those described with reference to FIGS. 1–70f, may then be inserted into the atrium with its spline collapsed. Once inside, the sheath is retracted such that the spline returns to its predetermined configuration and the ablation procedure is performed. The sheath is pushed over the spline when the ablation procedure is complete and the device is removed from the atrium. Similarly, the devices described above with reference to FIGS. 75–76 may be inserted with the loop in its retracted state, while the device shown in FIG. 74 may be inserted prior to pulling the wire attached to the distal tip. These devices may then be manipulated to cause the loops to form. The ablation procedure can then be performed. The devices described above with reference to FIGS. 71a–c, 73 and 77 need only be inserted to perform the procedure. The same is also true for malleable versions of the exemplary devices shown in FIGS. 62–70e.

Upon completion, the introducer is removed and the lasso tightened to isolate the left atrial appendage. The lasso may be detached from the probe and left in place to keep the appendage isolated. Where the aforementioned purse string technique is employed, the sutures may be tightened isolate the appendage. Alternatively, the appendage may be isolated in the manner described below with reference to FIG. 87.

In addition to thoracoscopic procedures, another area of cardiac treatment which will benefit from the present invention is the repair and replacement of mitral valves (which typically involves a thoracotomy, median sternotomy, or thoracostomy) because atrial fibrillation can be a complication of mitral disease which occurs prior to or subsequent to mitral valve surgery. More specifically, incisional reentry can develop subsequent to surgical procedures (such as mitral valve and thoracoscopic procedures) where an incision is made in the atrial wall that is subsequently closed by either sutures, mechanical closures, or other similar devices. Creating a lesion from the incision to the mitral valve annulus (or other anatomic barrier) will reduce the potential for reentrant propagation around the incision and, therefore, will terminate atrial fibrillation and/or prevent atrial fibrillation from developing. For example, if the left atrial appendage is used to access the interior of the left atrium for devices that create lesions on the endocardial surface, an additional lesion should be created from this access site to the mitral valve annulus so that incisional reentry will not develop when the incision is closed. This additional procedure is also applicable for right atrial procedures using incisions to access the interior of the atrium.

There is also a high prevalence of atrial fibrillation substrates proximate to the pulmonary veins. The creation of long, curvilinear lesions between pulmonary veins, around single pulmonary veins, and/or from pulmonary veins to the mitral valve annulus will prevent atrial fibrillation. The exemplary device illustrated FIGS. 62 and 63, which has an annular electrode assembly, is especially well suited for positioning ablation electrodes around the inside of a pulmonary vein. Alternatively, lesions may be created on the epicardial surface around pulmonary veins or between pulmonary veins. There is, however, some difficulty associated with epicardial access due to the presence of fatty deposits in the pulmonary vein region.

VI. Other Surgical Applications

A surgical method in accordance with a present invention may be used to reduce the level of bleeding during surgical procedures. The method generally comprises the steps of coagulating (or ablating) tissue to a predetermined depth and then forming an incision in the coagulated tissue. The coagulation can be accomplished by applying RF energy with, for example, the probe shown in FIG. 71a. Because the tissue is coagulated, the incision will not result in bleeding.

One exemplary procedure employing the present method is the removal of a diseased liver lobe. This a relatively time consuming procedure and, using conventional surgical techniques, there is a significant risk of serious bleeding. In accordance with one embodiment of the present invention, tissue in the lobe is coagulated to a depth of approximately 3 mm to 7 mm using RF energy. The coagulated tissue is then cut and separated with a scalpel, electro-surgical device, or other suitable instrument. To avoid bleeding, the depth of the cut should not exceed the depth of the coagulated tissue. The process of coagulating tissue and then forming an incision in the coagulated tissue can be repeated until the incision reaches the desired depth. Here, each coagulation and incision cycle will take approximately 90 seconds, 60 seconds to perform the coagulation and 30 seconds to perform the incision.

The present surgical technique is, of course, applicable to surgical procedures in addition to the removal of a liver lobe. Such procedures may, for example, involve the spleen, the kidneys, other areas of the liver, the heart, skeletal muscle, the lungs (such as a pulmonary lobotomy) and the brain. The present technique is also useful in oncological surgical procedures because cancerous tumors tend to be highly vascularized. One exemplary oncological procedure is the de-bulking of a cancerous tumor.

A surgical tool set in accordance with a present invention includes, among the other tools needed for a particular procedure, a device for coagulating soft tissue and a cutting the tissue. Suitable devices for coagulating soft tissue are illustrated for example, in FIGS. 62–88 and 95–101 with respect to the probe shown in FIGS. 71f and 71g, the portion of the probe which includes the second connector portion 321, the shaft 310 and a plurality of electrode elements can be included in the tool set with or without the handle 312". As noted above, scalpels, electro-surgical devices and other suitable instruments may be used to cut tissue. Preferably, the tool set is housed in a sterile package that has a flat rigid bottom portion and a top transparent top cover that provides recesses for the tools, thereby providing a ready to use surgical kit. The bottom portion may be formed from Tyvek® spun bonded plastic fibers, or other suitable materials, which allow the contents of the package to be sterilized after the tools are sealed within the package.

VII. Apparatus that Apply a Clamping Force

In accordance with another of the present inventions, and as shown by way of example in FIGS. 78–80, a clamp 382 includes a pair of clamp members 384 and 386, which are pivotably secured to one another by a pin 388, and an operative element 252 that may be of the type discussed above in Section III. Here, the operative element consists of a plurality of ablation electrodes 294. The clamp 382 also includes a pair of locking members 390 and 392 and an electrical connector 394 that may be used to, for example, connect the electrodes 294 to a source RF energy. Referring more specifically to FIG. 80, the clamp 382 may also, if desired, be curved over its length. Of course, the overall shape of the clamp will depend upon the procedure for which it is intended.

Certain procedures require the application of a clamping force to the bodily structure of interest in addition to the operation performed by the operative element. One such procedure is the isolation of an atrial appendage, which is discussed in greater detail below with reference to FIG. 87. As illustrated for example in FIG. 81, a suitable surgical device 396 for use in such a procedure includes a handle 398 having a pair of handle members 400 and 402 which are movable relative to one another. In the exemplary embodiment, the handle members are pivotably secured to one another by a pin 404 and include respective openings 406 and 408. The handle 398, which is actuated in a manner similar to scissors, is operably connected to a pair of support members 410 and 412 by, for example, a suitable mechanical linkage located within a housing 414. Actuation of the handle 398 causes the support members 410 and 412 to move relative to one another to create a clamping force. Of course, other types of handles that can cause movement of the support members may also be used.

An operative element 252, is associated with one or both (as shown) of the support members 410 and 412. Preferably, the operative element consists of one or more electrode elements 294 suitable for ablation (such as those discussed in detail in Section III above and operable in either the uni-polar or bi-polar mode) on each of the support members 410 and 412. Of course, the operative element 252 may also consist in whole or in part of other types of electrodes, such as a hot tip to cauterize appendage walls. The electrode elements 294 (or other operative element) may be connected to a control/power source surgical device by way of a connector 416. Wires extend from the electrode elements 294 through lumens in the support members 410 and 412 and handle 398 to the connector 416.

Figure 81:
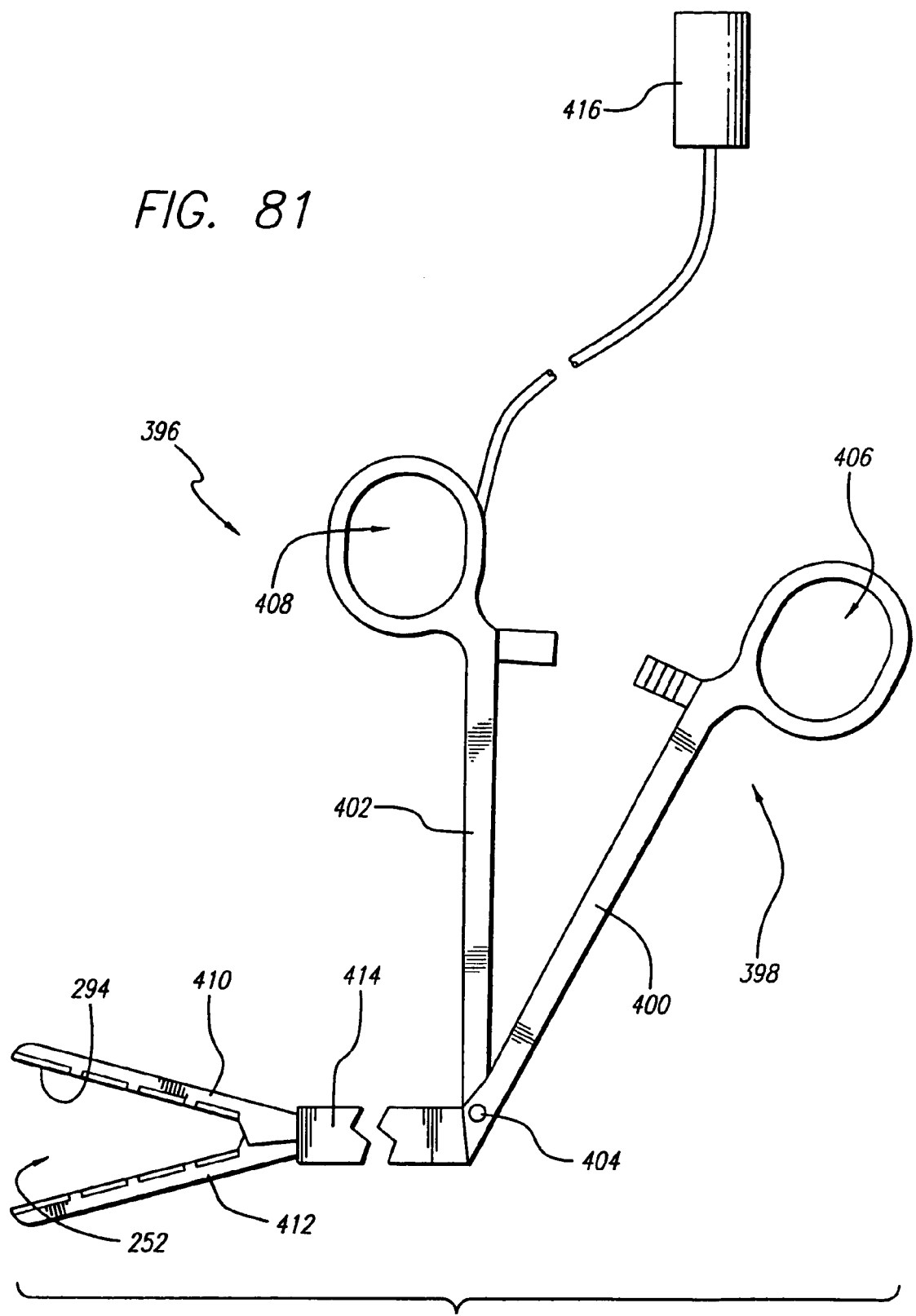
FIG. 81 is a side view of a surgical device for positioning an operative element within a patient and applying a clamping force to a bodily structure in accordance with a preferred embodiment of one of the present inventions.
Figure 82:
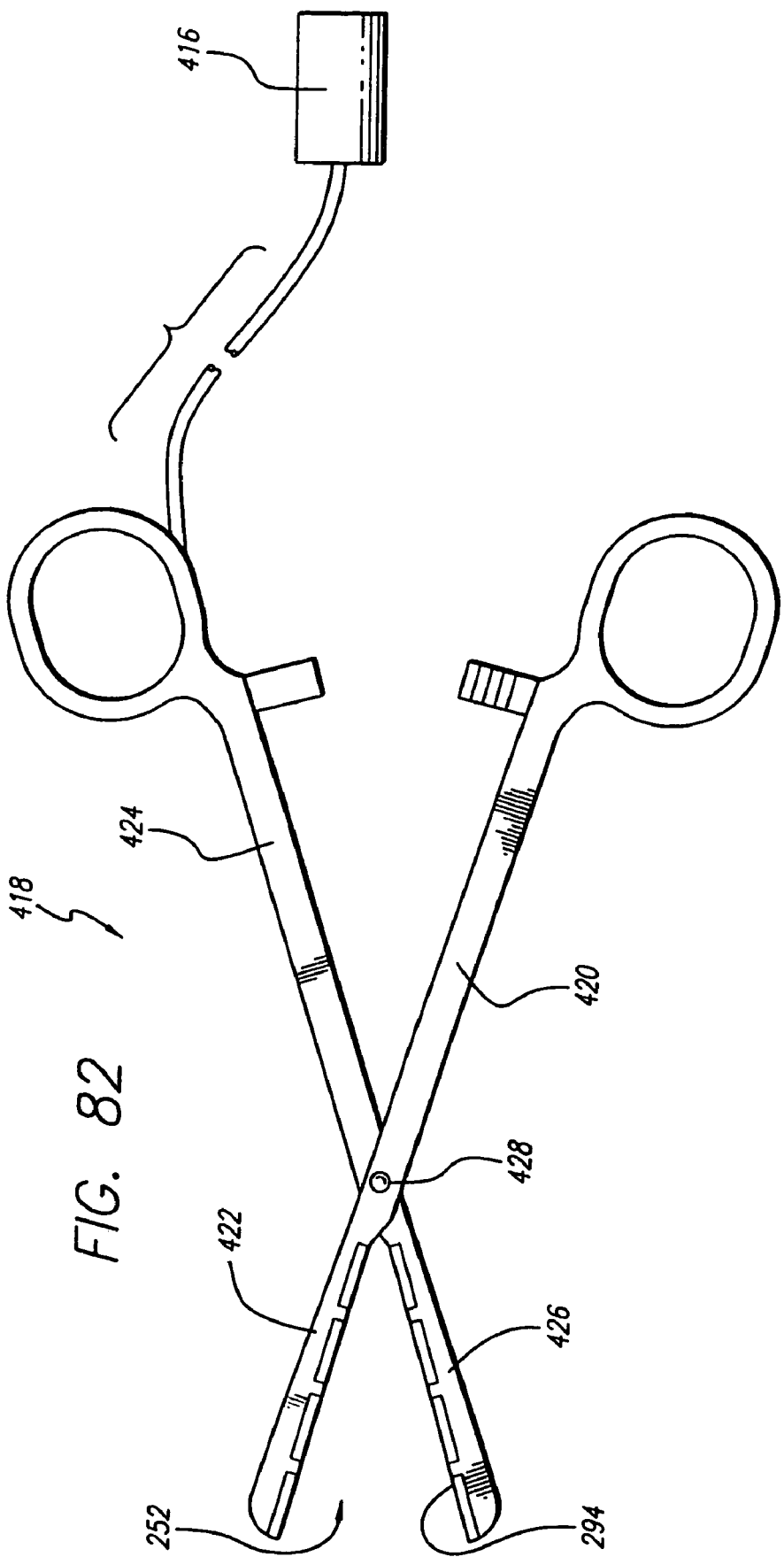
FIG. 82 is a side view of a surgical device for positioning an operative element within a patient and applying a clamping force to a bodily structure in accordance with another preferred embodiment of one of the present inventions.

Turning to FIG. 82, surgical device 418 is similar to that shown in FIG. 81 except that handle 398 is not connected to the operative element support members 410 and 412 by a mechanical linkage. Instead, the handle member 420 and support member 422 form an integral unit as do the handle member 424 and support member 426. The integral units are pivotably secured to one another by a pin 428. Thus, while the embodiment shown in FIG. 81 is especially useful in situations where thoracostomy is used, the embodiment shown in FIG. 82 is especially useful for thoracotomy or median sternotomy access. In either case, the atrial appendage (or other bodily structure) is captured (or clamped) such that it is perpendicular to the surgical device.

Figure 83:
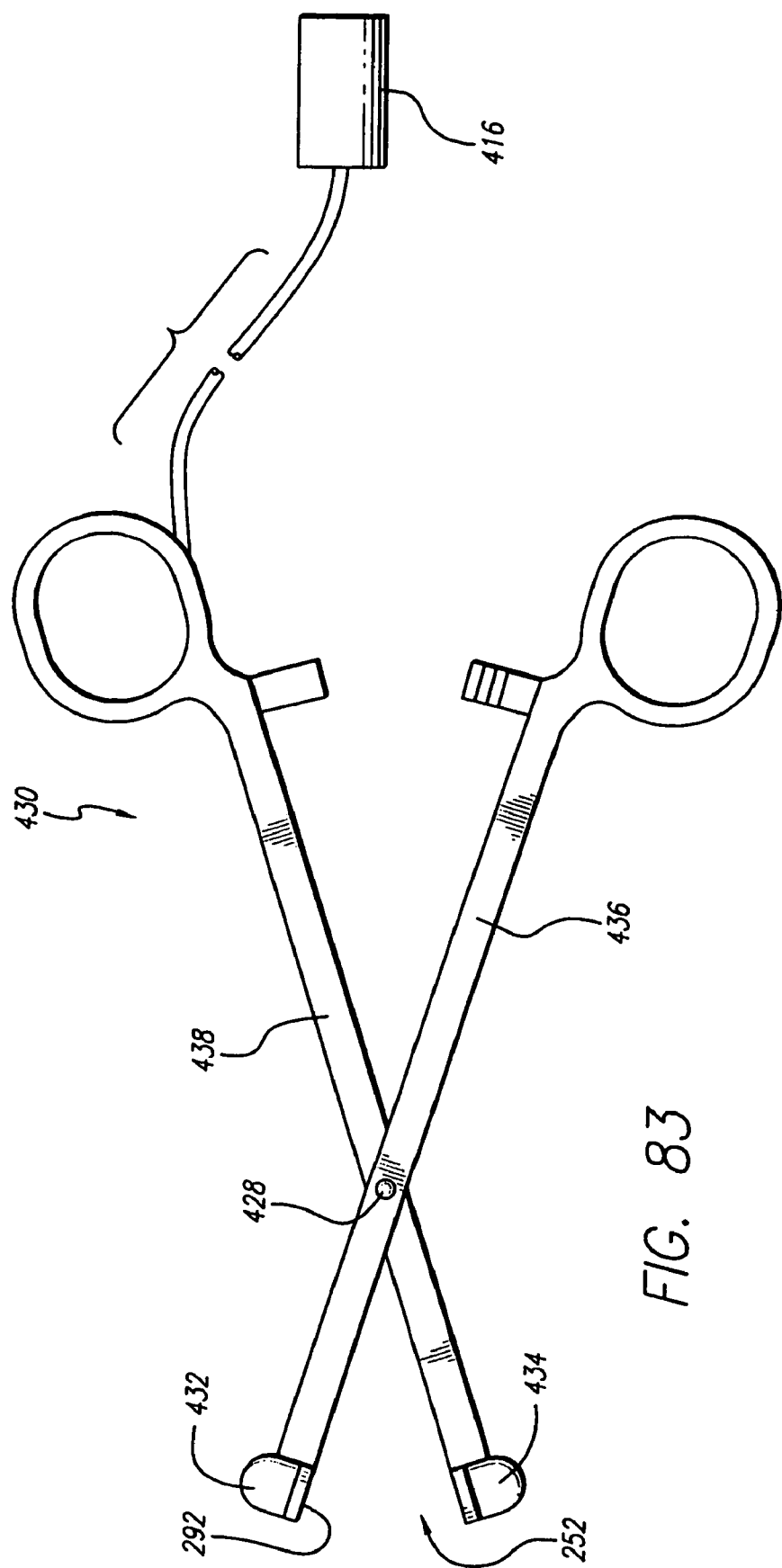
FIG. 83 is a side view of a surgical device for positioning an operative element within a patient and applying a clamping force to a bodily structure in accordance with still another preferred embodiment of one of the present inventions.
Figure 85B:
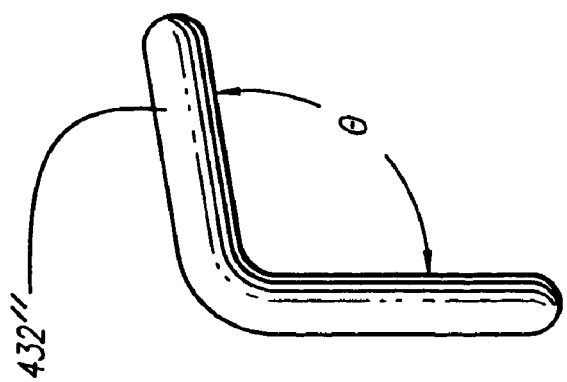
FIG. 85b is a top view of still another operative element supporting member.
Figure 85A:
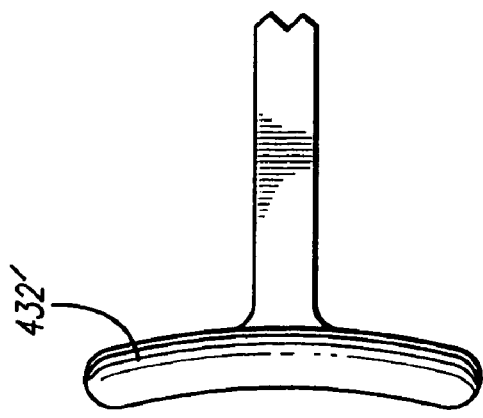
FIG. 85a is a top view of another operative element supporting member.
Figure 84:
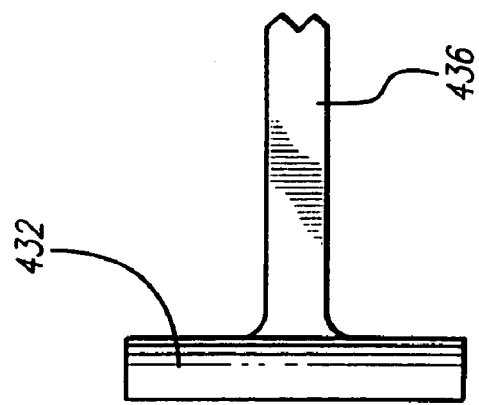
FIG. 84 is a top view of the operative element supporting member of the surgical device shown in FIG. 83.
Figure 86:
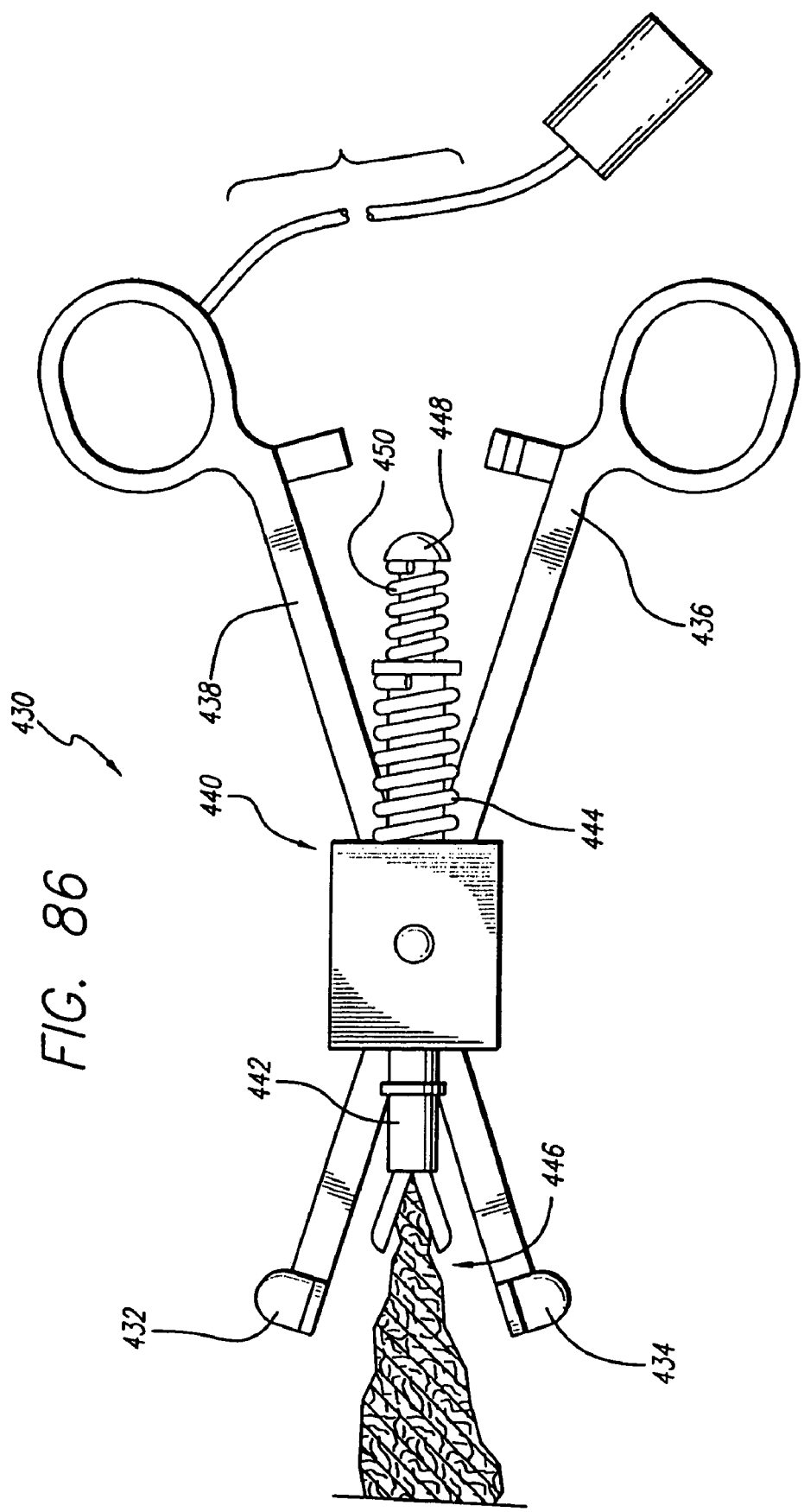
FIG. 86 is a side view of a surgical device for positioning an operative element within a patient and applying a clamping force to a bodily structure in accordance with yet another preferred embodiment of one of the present invention.

As shown by way of example in FIGS. 83 and 84, the operative element support members 432 and 434 in exemplary surgical device 430 are secured to the distal ends of the handle members 436 and 438, respectively, such that the support members are perpendicular to the handle members. Although the handle members 436 and 438 are respectively secured to the middle portion of the support members 432 and 434 (viewed longitudinally as shown in FIG. 84), the support members may be offset in one direction or the other to suit particular needs (note FIG. 84*a*). Additionally, as illustrated for example in FIGS. 85*a* and 85*b*, the support members (432' and 432") may also be curved, or L-shaped with the angle θ between about 90° and about 180°. The preferred embodiments shown in FIGS. 83–85*b* hold the bodily structure such that it is parallel to the surgical device.

The exemplary embodiments shown in FIGS. 83–85*b* may be provided with a holding device that is used to grasp a bodily structure and pull the structure in the proximal direction. As illustrated for example in FIG. 86, the holding device 440 includes a cylindrical member 442 that is biased in the proximal direction by a spring 444. A pair of clamping jaws 446 extend outwardly from the distal end of the cylindrical member 442. The clamping jaws 446, which pivot relative to one another, are connected to a rod 448 which passes through the cylindrical member 442 and slides relative thereto. The rod 448 is biased in the proximal direction by a spring 450 which, in turn, biases the clamping jaws 446 in the proximal direction against the distal end of the cylindrical member 442. As such, the clamping jaws 446 are biased to their closed position and the jaws may be loosened by pushing the rod 448 in the distal direction.

VII. Applications of Apparatus that Apply a Clamping Force

The exemplary clamp 382 shown in FIGS. 78–80 can both isolate a bodily structure and deliver the therapeutic and/or diagnostic effects of the operative element 252. In an atrial appendage isolation procedure, for example, the clamp 382 may be used to capture the atrial appendage and isolate it from the interior of the atrium. RF energy may then be delivered via the electrodes 294 (in either the uni-polar mode or the bi-polar mode) to fuse the walls of the atrial appendage to one another. Thereafter, the clamp may either be removed, or disconnected from the RF energy source and left in place.

Figure 87:
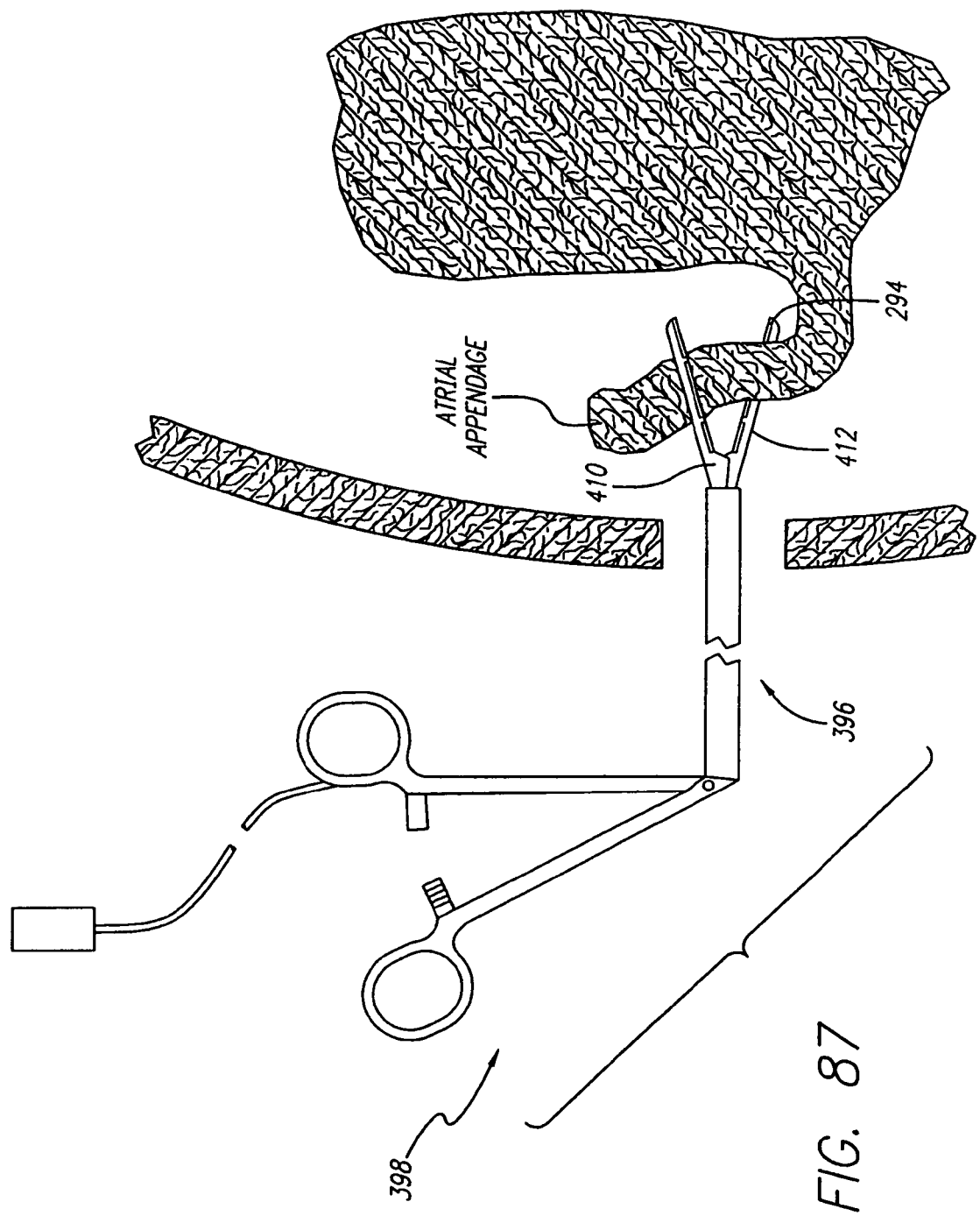
FIG. 87 is a side, partial section view of an exemplary procedure involving the surgical device shown in FIG. 81.

Turning to FIG. 87, one exemplary use of the surgical device 396 shown in FIG. 81 is the isolation of an atrial appendage. Here, the device is inserted into an opening of the chest wall. The atrial appendage is captured between the support members 410 and 412 by actuating the handle 398. RF energy is then transmitted, either from the electrodes 294 on one support member to the electrodes on the other (bi-polar mode) or from the electrodes to an indifferent reference electrode on, for example, a patch (uni-polar mode) to thermally fuse the walls of the atrial appendage together and isolate the atrial appendage. The surgical device shown in FIGS. 82–87 may be used in similar fashion.

Figure 88:
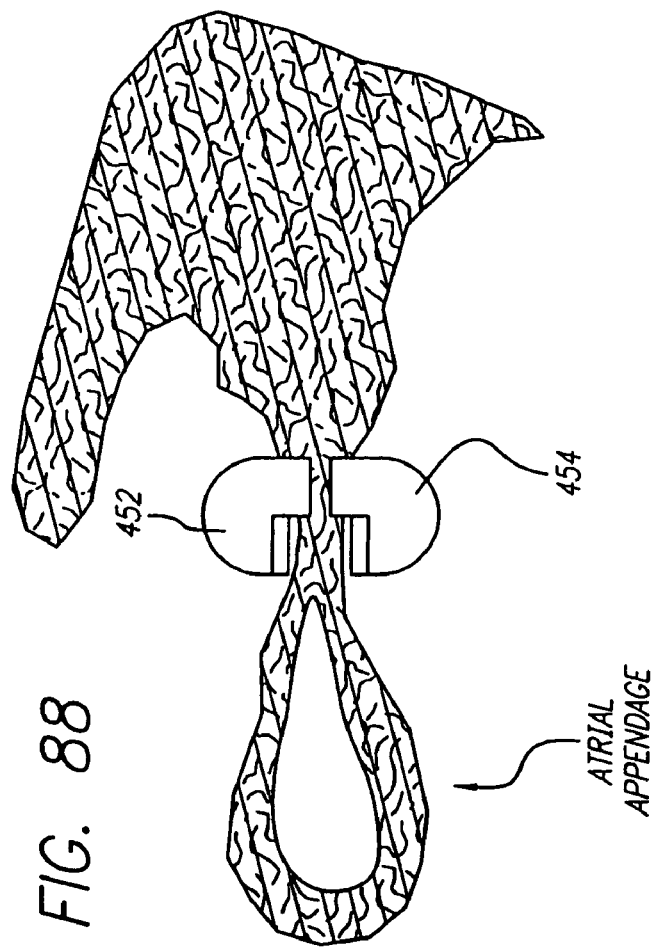
FIG. 88 is a side, partial section view of an exemplary procedure involving a surgical device having an alternate support member configuration.

As shown by way of example in FIG. 88, the operative element (such as, for example, electrodes 294) may be offset from one side or the other of the support members 452 and 454. This offset configuration, which may be used in conjunction with any of the exemplary devices shown in FIGS. 81–86, is especially useful in an atrial appendage isolation procedure. Here, the electrodes 294 are offset from the side of the support members 452 and 454 that is proximate to the interior of the left atrium. By making the portions of the support members that do not support the electrodes insulative, and by directing the RF energy towards the side of the appendage (or other structure) isolated by the clamping force, coagulum or thrombus due to heating static blood will develop in the portion of the appendage that will be isolated from the blood pool when the side walls fuse to one another. Of course, when the patient is in bypass, such masking is unnecessary unless it is being used to create lesions of a certain shape.

IX. Power Control

A. General

Figure 89:
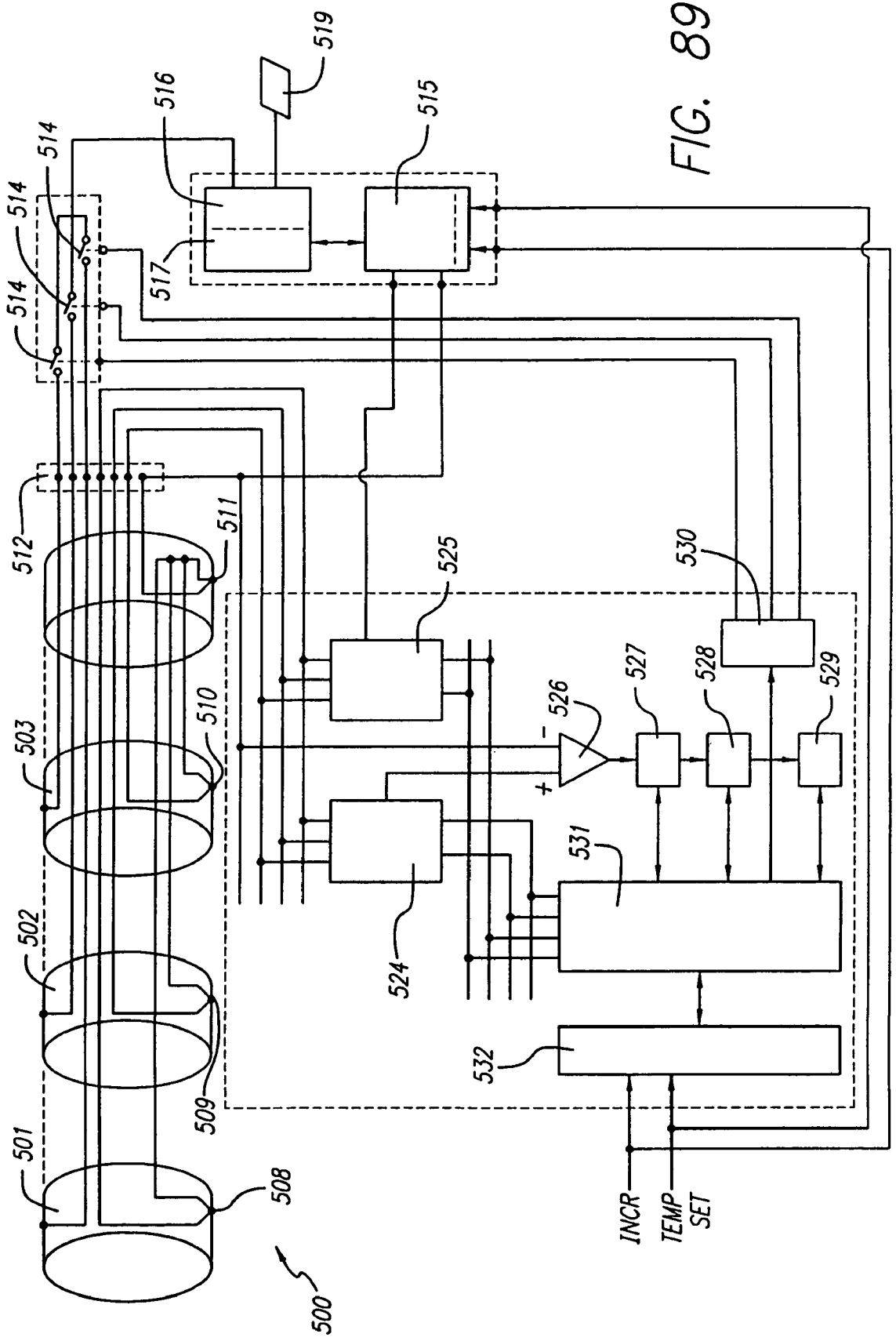

FIG. 89 shows, in schematic form, a representative system 500 for applying ablating energy by multiple emitters based, at least in part, upon local temperature conditions sensed by multiple sensing elements.

In FIG. 89, the multiple sensing elements comprise thermocouples 508, 509, and 510 individually associated with the multiple emitters of ablating energy, which comprise electrode regions 501, 502, and 503. The system 500 also includes a common reference thermocouple 511 carried within the coupler element for exposure to the blood pool. Alternatively, other kinds of temperature sensing elements can be used, like, for example, thermistors, fluoroptic sensors, and resistive temperature sensors, in which case the reference thermocouple 511 would typically not be required.

The system 500 further includes an indifferent electrode 519 for operation in a uni-polar mode.

The ablating energy emitters 501, 502, 503 can comprise the rigid electrode segments previously described. Alternatively, the electrode regions 501, 502, 503 can comprise a continuous or segmented flexible electrode of wrapped wire or ribbon. It should be appreciated that the system 500 can be used in association with any ablating element that employs multiple, independently actuated ablating elements.

The system 500 includes a source 517 of ablating energy. In FIG. 89, the source 517 generates radio frequency (RF) energy. The source 517 is connected (through a conventional isolated output stage 516) to an array of power switches 514, one for each electrode region 501, 502, and 503. A connector 512 (carried by the probe handle) electrically couples each electrode region 501, 503, 503 to its own power switch 514 and to other parts of the system 500.

The system 500 also includes a microcontroller 531 coupled via an interface 530 to each power switch 514. The microcontroller 531 turns a given power switch 514 on or off to deliver RF power from the source 517 individually to the electrode regions 501, 502, and 503. The delivered RF energy flows from the respective electrode region 501, 502, and 503, through tissue, to the indifferent electrode 519, which is connected to the return path of the isolated output stage 516.

The power switch 514 and interface 530 configuration can vary according to the type of ablating energy being applied. FIG. 90 shows a representative implementation for applying RF ablating energy.

In this implementation, each power switch 514 includes an N-MOS power transistor 535 and a P-MOS power transistor 536 coupled in between the respective electrode region 501, 502, and 503 and the isolated output stage 516 of the power source 517.

A diode 533 conveys the positive phase of RF ablating energy to the electrode region. A diode 534 conveys the negative phase of the RF ablating energy to the electrode region. Resistors 537 and 538 bias the N-MOS and P-MOS power transistors 535 and 536 in conventional fashion.

The interface 530 for each power switch 514 includes two NPN transistors 539 and 540. The emitter of the NPN transistor 539 is coupled to the gate of the N-MOS power transistor 535. The collector of the NPN transistor 540 is coupled to the gate of the P-MOS power transistor 534.

The interface for each power switch 514 also includes a control bus 543 coupled to the microcontroller 531. The control bus 543 connects each power switch 514 to digital ground (DGND) of the microcontroller 531. The control bus 543 also includes a (+) power line (+5V) connected to the collector of the NPN transistor 539 and a (−) power line (−5V) connected to the emitter of the NPN interface transistor 540.

The control bus 543 for each power switch 514 further includes an $E_{SEL}$ line. The base of the NPN transistor 539 is coupled to the $E_{SEL}$ line of the control bus 543. The base of the NPN transistor 540 is also coupled to the $E_{SEL}$ line of the control bus 543 via the Zener diode 541 and a resistor 532. The $E_{SEL}$ line connects to the cathode of the Zener diode 541 through the resistor 532. The Zener diode 541 is selected so that the NPN transistor 540 turns on when $E_{SEL}$ exceeds about 3 volts (which, for the particular embodiment shown, is logic 1).

It should be appreciated that the interface 530 can be designed to handle other logic level standards. In the particular embodiment, it is designed to handle conventional UTL (transistor transfer logic) levels.

The microcontroller 531 sets $E_{SEL}$ of the control bus 543 either at logic 1 or at logic 0. At logic 1 the gate of the N-MOS transistor 535 is connected to (+) 5 volt line through the NPN transistors 539. Similarly, the gate of the P-MOS transistor 536 is connected to the (−) 5 volt line through the NPN transistor 540. This conditions the power transistors 535 and 536 to conduct RF voltage from the source 517 to the associated electrode region. The power switch 514 is "on."

When the microcontroller 531 sets $E_{SEL}$ at logic 0, no current flows through the NPN transistors 539 and 540. This conditions the power transistors 535 and 536 to block the conduction of RF voltage to the associated electrode region. The power switch 514 is "off."

The system 500 (see FIG. 89) further includes two analog multiplexers (MUX) 524 and 525. The multiplexers 524 and 525 receive voltage input from each thermocouple 508, 509, 510, and 511. The microcontroller 531 controls both multiplexers 524 and 525 to select voltage inputs from the multiple temperature sensing thermocouples 508, 509, 510, and 511.

The voltage inputs from the thermocouples 508, 509, 510, and 511 are sent to front end signal conditioning electronics. The inputs are amplified by differential amplifier 526, which reads the voltage differences between the copper wires of the thermocouples 508/509/510 and the reference thermocouple 511. The voltage differences are conditioned by element 527 and converted to digital codes by the analog-to-digital converter 528. The look-up table 529 converts the digital codes to temperature codes. The temperature codes are read by the microcontroller 531.

The microcontroller 531 compares the temperature codes for each thermocouple 508, 509, and 510 to preselected criteria to generate feedback signals. The preselected criteria are inputted through a user interface 532. These feedback signals control the interface power switches 514 via the interface 530, turning the electrodes 501, 502, and 503 off and on.

The other multiplexer 525 connects the thermocouples 508, 509, 510, and 511 selected by the microcontroller 531 to a temperature controller 515. The temperature controller 515 also includes front end signal conditioning electronics, as already described with reference to elements 526, 527, 528, and 529. These electronics convert the voltage differences between the copper wires of the thermocouples 508/509/510 and the reference thermocouple 511 to temperature codes. The temperature codes are read by the controller and compared to preselected criteria to generate feedback signals. These feedback signals control the amplitude of the voltage (or current) generated by the source 517 for delivery to the electrodes 501, 502, and 503.

Based upon the feedback signals of the microcontroller 531 and the temperature controller 515, the system 500 distributes power to the multiple electrode regions 501, 502, and 503 to establish and maintain a uniform distribution of temperatures along the ablating element. In this way, the system 500 obtains safe and efficacious lesion formation using multiple emitters of ablating energy.

The system 500 can control the delivery of ablating energy in different ways. Representative modes will now be described.

B. Individual Amplitudes/Collective Duty Cycle

The electrode regions 501, 502, and 503 will be symbolically designated E(J), where J represents a given electrode region (J=1 to N).

As before described, each electrode region E(J) has at least one temperature sensing element 508, 509, and 510, which will be designated S(J,K), where J represents the electrode region and K represents the number of temperature sensing elements on each electrode region (K=1 to M).

In this mode (see FIG. 91), the microcontroller 516 operates the power switch interface 530 to deliver RF power from the source 517 in multiple pulses of duty cycle 1/N.

With pulsed power delivery, the amount of power ($P_{E(J)}$) conveyed to each individual electrode is as follows:

$$P_{E(J)} \sim AMP_{E(J)}^2 \times DUTYCYCLE_{E(J)}$$

where:

$AMP_{E(J)}$ is the amplitude of the RF voltage conveyed to the electrode region E(J), and $DUTYCYCLE_{E(J)}$ is the duty cycle of the pulse, expressed as follows:

$$DUTYCYCLE_{E(J)} = TON_{E(J)}/[TON_{E(J)} + TOFF_{E(J)}]$$

where:

$TON_{E(J)}$ is the time that the electrode region E(J) emits energy during each pulse period, $TOFF_{E(J)}$ is the time that the electrode region E(J) does not emit energy during each pulse period.

The expression $TON_{E(J)}+TOFF_{E(J)}$ represents the period of the pulse for each electrode region E(J).

In this mode, the microcontroller 531 collectively establishes duty cycle ($DUTYCYCLE_{E(J)}$) of 1/N for each electrode region (N being equal to the number of electrode regions).

The microcontroller 531 may sequence successive power pulses to adjacent electrode regions so that the end of the duty cycle for the preceding pulse overlaps slightly with the beginning of the duty cycle for the next pulse. This overlap in pulse duty cycles assures that the source 517 applies power continuously, with no periods of interruption caused by open circuits during pulse switching between successive electrode regions.

In this mode, the temperature controller 515 makes individual adjustments to the amplitude of the RF voltage for each electrode region ($AMP_{E(J)}$), thereby individually changing the power $P_{E(J)}$ of ablating energy conveyed during the duty cycle to each electrode region, as controlled by the microcontroller 531.

In this mode, the microcontroller 531 cycles in successive data acquisition sample periods. During each sample period, the microcontroller 531 selects individual sensors S(J,K), and voltage differences are read by the controller 515 (through MUX 525) and converted to temperature codes TEMP(J).

When there is more than one sensing element associated with a given electrode region, the controller 515 registers all sensed temperatures for the given electrode region and selects among these the highest sensed temperature, which constitutes TEMP(J).

In this mode, the controller 515 compares the temperature TEMP(J) locally sensed at each electrode E(J) during each data acquisition period to a set point temperature $TEMP_{SET}$ established by the physician. Based upon this comparison, the controller 515 varies the amplitude $AMP_{E(J)}$ of the RF voltage delivered to the electrode region E(J), while the microcontroller 531 maintains the $DUTYCYCLE_{E(J)}$ for that electrode region and all other electrode regions, to establish and maintain TEMP(J) at the set point temperature $TEMP_{SET}$.

The set point temperature $TEMP_{SET}$ can vary according to the judgment of the physician and empirical data. A representative set point temperature for cardiac ablation is believed to lie in the range of 40° C. to 95° C., with 70° C. being a representative preferred value.

The manner in which the controller 515 governs $AMP_{E(J)}$ can incorporate proportional control methods, proportional integral derivative (PID) control methods, or fuzzy logic control methods.

For example, using proportional control methods, if the temperature sensed by the first sensing element TEMP(1) >$TEMP_{SET}$, the control signal generated by the controller 515 individually reduces the amplitude $AMP_{E(1)}$ of the RF voltage applied to the first electrode region E(1), while the microcontroller 531 keeps the collective duty cycle $DUTYCYCLE_{E(1)}$ for the first electrode region E(1) the same. If the temperature sensed by the second sensing element TEMP(2)<$TEMP_{SET}$, the control signal of the controller 515 increases the amplitude $AMP_{E(2)}$ of the pulse applied to the second electrode region E(2), while the microcontroller 531 keeps the collective duty cycle $DUTYCYCLE_{E(2)}$ for the second electrode region E(2) the same as $DUTYCYCLE_{E(1)}$, and so on. If the temperature sensed by a given sensing element is at the set point temperature $TEMP_{SET}$, no change in RF voltage amplitude is made for the associated electrode region.

The controller 515 continuously processes voltage difference inputs during successive data acquisition periods to individually adjust $AMP_{E(J)}$ at each electrode region E(J), while the microcontroller 531 keeps the collective duty cycle the same for all electrode regions E(J). In this way, the mode maintains a desired uniformity of temperature along the length of the ablating element.

Using a proportional integral differential (PID) control technique, the controller 515 takes into account not only instantaneous changes that occur in a given sample period, but also changes that have occurred in previous sample periods and the rate at which these changes are varying over time. Thus, using a PID control technique, the controller 515 will respond differently to a given proportionally large instantaneous difference between TEMP (J) and $TEMP_{SET}$, depending upon whether the difference is getting larger or smaller, compared to previous instantaneous differences, and whether the rate at which the difference is changing since previous sample periods is increasing or decreasing.

C. Deriving Predicted Hottest Temperature

Because of the heat exchange between the tissue and the electrode region, the temperature sensing elements may not measure exactly the maximum temperature at the region. This is because the region of hottest temperature occurs beneath the surface of the tissue at a depth of about 0.5 to 2.0 mm from where the energy emitting electrode region (and the associated sensing element) contacts the tissue. If the power is applied to heat the tissue too quickly, the actual maximum tissue temperature in this subsurface region may exceed 100° C. and lead to tissue desiccation and/or micro-explosion.

Figure 92:
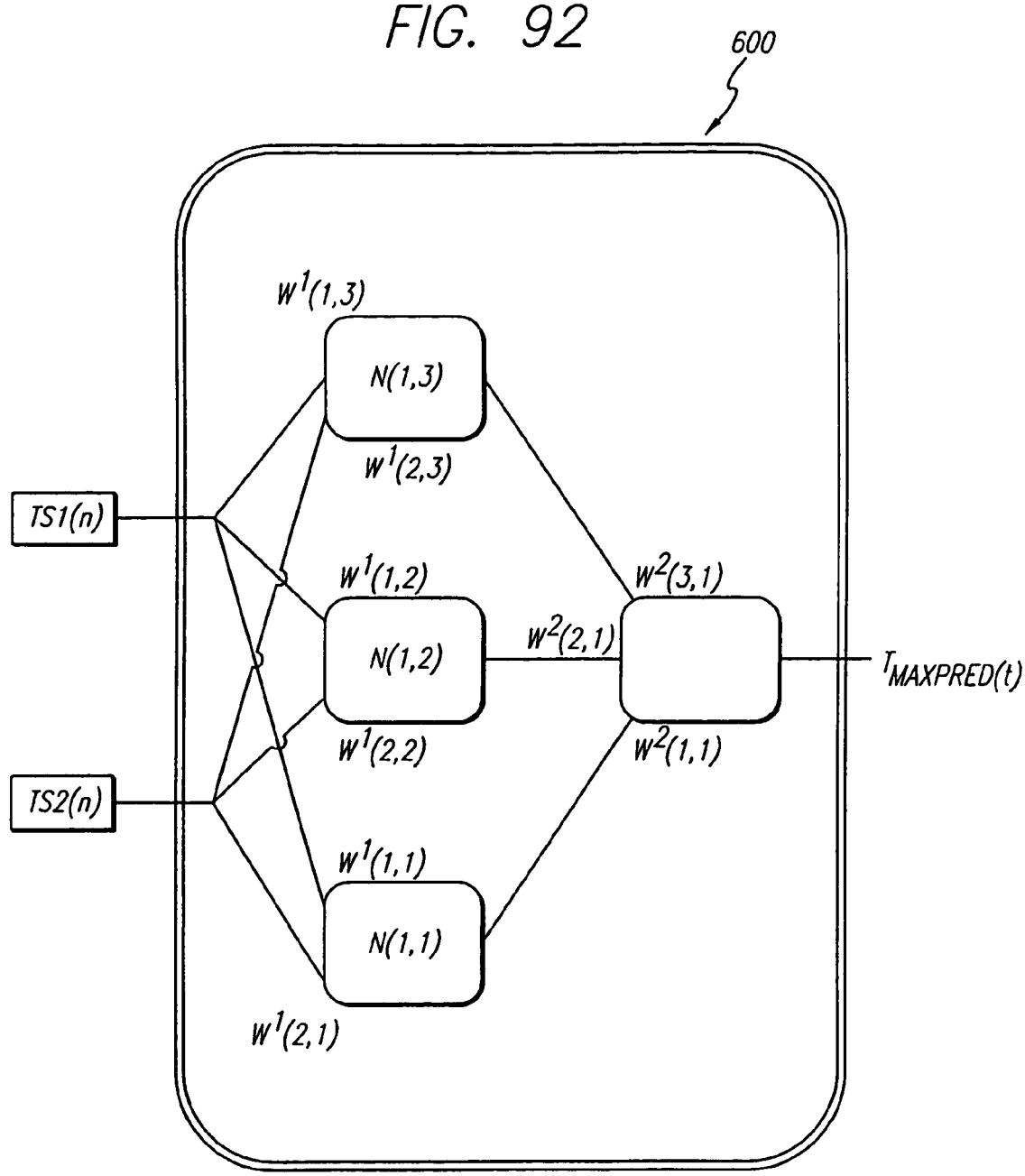
FIG. 92 is a schematic view of a neural network predictor, which receives as input the temperatures sensed by multiple sensing elements at a given electrode region and outputs a predicted temperature of the hottest tissue region.

FIG. 92 shows an implementation of a neural network predictor 600, which receives as input the temperatures sensed by multiple sensing elements S(J,K) at each electrode region, where J represents a given electrode region (J=1 to N) and K represents the number of temperature sensing elements on each electrode region (K=1 to M). The predictor 600 outputs a predicted temperature of the hottest tissue region $T_{MAXPRED}(t)$. The controller 515 and microcontroller 531 derive the amplitude and duty cycle control signals based upon $T_{MAXPRED}(t)$, in the same manners already described using TEMP(J).

Figure 91:
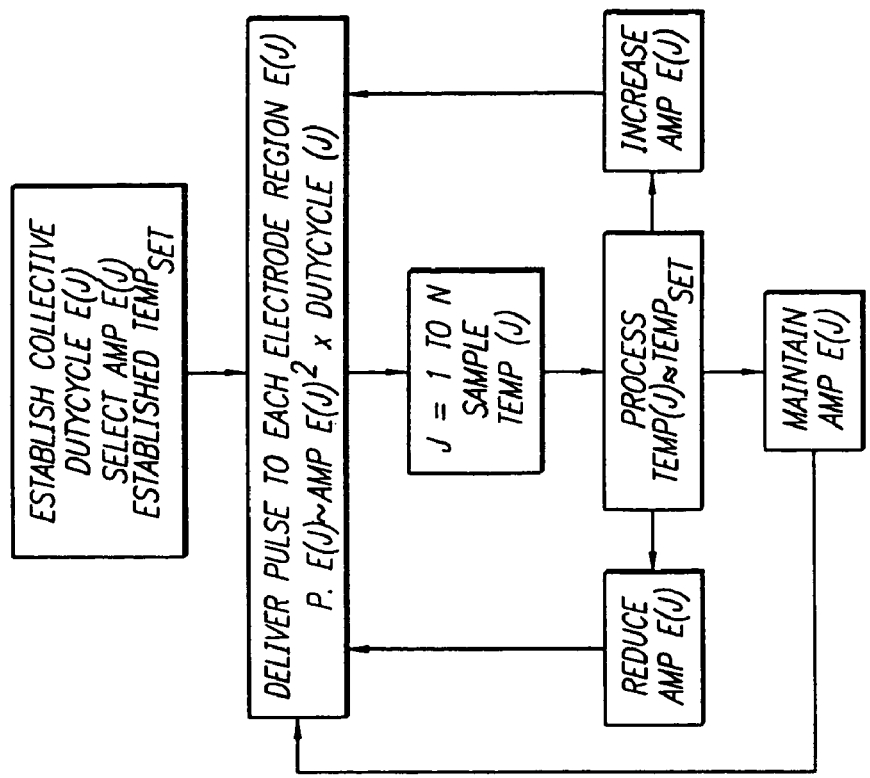
FIG. 91 is a schematic flow chart showing an implementation of the temperature feedback controller shown in FIGS. 89 and 90, using individual amplitude control with collective duty cycle control.

The predictor 600 uses a two-layer neural network, although more hidden layers could be used. As shown in FIG. 91, the predictor 600 includes first and second hidden layers and four neurons, designated $N_{(L,X)}$, where L identifies the layer 1 or 2 and X identifies a neuron on that layer. The first layer (L=1) has three neurons (X=1 to 3), as follows $N_{(1,1)}$; $N_{(1,2)}$; and $N_{(1,3)}$. The second layer (L=2) comprising one output neuron (X=1), designated $N_{(2,1)}$.

Temperature readings from the multiple sensing elements, only two of which—TS1(n) and TS2(n)—are shown for purposes of illustration, are weighed and inputted to each neuron $N_{(1,1)}$; $N_{(1,2)}$; and $N_{(1,3)}$ of the first layer. FIG. 31 represents the weights as $W^L_{(k,N)}$, where L=1; k is the input sensor order; and N is the input neuron number 1, 2, or 3 of the first layer.

The output neuron $N_{(2,1)}$ of the second layer receives as inputs the weighted outputs of the neurons $N_{(1,1)}$; $N_{(1,2)}$; and $N_{(1,3)}$. FIG. 91 represents the output weights as $W^L_{(O,X)}$, where L=2; O is the output neuron 1, 2, or 3 of the first layer; and X is the input neuron number of the second layer. Based upon these weighted inputs, the output neuron $N_{(2,1)}$ predicts $T_{MAXPRED}(t)$. Alternatively, a sequence of past reading samples from each sensor could be used as input. By doing this, a history term would contribute to the prediction of the hottest tissue temperature.

The predictor 600 must be trained on a known set of data containing the temperature of the sensing elements TS1 and TS2 and the temperature of the hottest region, which have been previously acquired experimentally. For example, using a back-propagation model, the predictor 600 can be trained to predict the known hottest temperature of the data set with the least mean square error. Once the training phase is completed the predictor 600 can be used to predict $T_{MAXPRED}(t)$.

Other types of data processing techniques can be used to derive $T_{MAXPRED}(t)$. See, e.g., co-pending U.S. application Ser. No. 08/801,484, filed Feb. 18, 1997, which is a File Wrapper Continuation of U.S. application Ser. No. 08/503,736, filed Jul. 18, 1995, which is a File Wrapper Continuation of U.S. application Ser. No. 08/266,934, filed Jun. 27, 1994, and entitled "Tissue Heating and Ablation Systems and Methods Using Predicted Temperature for Monitoring and Control."

It should be noted that there are certain considerations which should be taken into account when ablation/coagulation procedures are performed with little or no fluid present. Such procedures include, for example, procedures performed during cardiac bypass. These considerations stem from the fact that the convective cooling effects associated with air are far less than that associated with blood and other fluids. In addition, the intimate physical (and thermal) contact between the electrodes and tissue will allow heat to be exchanged relatively freely therebetween.

Because the electrodes which transmit RF energy have high conductivity, they will be subjected to much less ohmic heating. However, heat will be drawn from the tissue to the electrode as RF power is applied to the tissue, which results in a time lag between hottest tissue temperature and the temperature of the electrode as well as a temperature gradient within the tissue near the tissue surface. The electrode temperature will eventually approach the tissue temperature. At this point, there will be a relatively small temperature gradient between the hottest tissue temperature and the electrode temperature, as well as relatively little heat transfer between the tissue and the electrode. Accordingly, the temperature control algorithm should take into account the time lag between the sub-surface tissue temperature and the temperature sensed at the electrode. However, the difference between the plateau tissue temperatures and the sensed temperatures can typically be disregarded.

In addition to the control considerations, the user interface should also allow the physician to indicated whether convective cooling is going to be present, thereby allowing the physician to select the proper temperature control algorithm.

The illustrated and preferred embodiments used digital processing controlled by a computer to analyze information and generate feedback signals. It should be appreciated that other logic control circuits using micro-switches, AND/OR gates, invertors, analog circuits, and the like are equivalent to the micro-processor controlled techniques shown in the preferred embodiment.

Although the present inventions have been described in terms of the preferred embodiments above, numerous modifications and/or additions to the above-described preferred embodiments would be readily apparent to one skilled in the art. It is intended that the scope of the present invention extends to all such modifications and/or additions.

We claim:

1. A method of treating an atrium having an endocardial surface and an epicardial surface, comprising the steps of:
    engaging the atrial appendage from the epicardial surface;
    positioning a lasso around the epicardial surface side of the atrial appendage;
    forming an aperture in an atrial appendage;
    inserting a surgical probe through the aperture in the atrial appendage; and
    forming a lesion in the endocardial surface with the surgical probe.

2. A method as claimed in claim 1, further comprising the steps of:
    inserting an introducer into the atrium through the aperture; and
    tightening the lasso around the introducer.

3. A method as claimed in claim 2, further comprising the steps of:
    withdrawing the introducer after the lesion has been formed in the endocardial surface; and
    tightening the lasso to isolate the atrial appendage.

4. A method as claimed in claim 1, wherein the step of inserting a surgical probe comprises inserting a surgical probe with a collapsible portion in a collapsed state through the aperture in the atrial appendage and then expanding the collapsible portion within the atrium.

5. A method as claimed in claim 1, wherein the step of inserting a surgical probe comprises inserting a surgical probe with a loop portion in a retracted state through the aperture in the atrial appendage and then forming a loop within the atrium.

6. A method as claimed in claim 1, wherein the step of inserting a surgical probe comprises inserting a surgical probe including a malleable shaft through the aperture in the atrial appendage.

7. A method as claimed in claim 1, wherein the step of forming a lesion comprises forming a lesion in the endocardial surface by transmitting electrical energy through atrial tissue with the surgical probe.

8. A method as claimed in claim 1, further comprising the step of:
    creating a lesion from the atrial appendage to an anatomic barrier.

9. A method of treating an atrium having an endocardial surface and an epicardial surface, comprising the step of:
    forming an aperture in an atrial appendage;
    inserting a surgical probe through the aperture in the atrial appendage;
    forming a lesion in the endocardial surface with the surgical probe; and
    creating a lesion from the atrial appendage to the mitral valve annulus.

10. A method as claimed in claim 9, wherein the step of forming an aperture comprises forming an aperture in an atrial appendage from the epicardial surface.

11. A method as claimed in claim 9, further comprising the steps of:
    inserting an introducer into the atrium through the aperture; and
    tightening sutures around the introducer.

12. A method as claimed in claim 11, further comprising the steps of:
    withdrawing the introducer after the lesion has been formed in the endocardial surface; and
    tightening the sutures to isolate the atrial appendage.

13. A method as claimed in claim 9, wherein the step of inserting a surgical probe comprises inserting a surgical probe with a collapsible portion in a collapsed state through the aperture in the atrial appendage and then expanding the collapsible portion within the atrium.

14. A method as claimed in claim 11, wherein the step of inserting a surgical probe comprises inserting a surgical probe with a loop portion in a retracted state through the aperture in the atrial appendage and then forming a loop within the atrium.

15. A method as claimed in claim 9, wherein the step of inserting a surgical probe comprises inserting a surgical probe including a malleable shaft through the aperture in the atrial appendage.

16. A method as claimed in claim 9, wherein the step of forming a lesion comprises forming a lesion in the endocardial surface by transmitting electrical energy through atrial tissue with the surgical probe.

* * * * *